United States Patent [19]

Ferrari et al.

[11] Patent Number: 5,641,648
[45] Date of Patent: Jun. 24, 1997

[54] METHODS FOR PREPARING SYNTHETIC REPETITIVE DNA

[75] Inventors: Franco A. Ferrari, La Jolla; Joseph Cappello, San Diego, both of Calif.; Charles Richardson, Florence, Mont.

[73] Assignee: Protein Polymer Technologies, Inc., San Diego, Calif.

[21] Appl. No.: 175,155

[22] Filed: Dec. 29, 1993

Related U.S. Application Data

[63] Continuation-in-part of Ser. No. 53,049, Apr. 22, 1993, abandoned, which is a continuation of Ser. No. 114,618, Oct. 29, 1987, Pat. No. 5,243,038, and a continuation-in-part of Ser. No. 609,716, Nov. 6, 1990, Pat. No. 5,514,581, which is a continuation-in-part of Ser. No. 269,429, Nov. 9, 1988, abandoned, which is a continuation-in-part of Ser. No. 114,618, Oct. 29, 1987, Pat. No. 5,243,038, which is a continuation-in-part of Ser. No. 927,258, Nov. 4, 1986, abandoned.

[51] Int. Cl.⁶ .................... C12P 21/02; C12N 15/11; C07H 21/00; C07H 21/04
[52] U.S. Cl. .................... 435/69.1; 435/71.2; 435/172.1; 435/252.8; 435/320.1; 536/23.1; 536/24.1; 536/25.3
[58] Field of Search .................... 435/69.1, 71.2, 435/172.1, 320.1, 252.8; 536/23.1, 24.1, 25.3

[56] References Cited

U.S. PATENT DOCUMENTS 5,089,406  2/1992  Williams et al. .................... 435/172.3

OTHER PUBLICATIONS

White et al. (1989), Trends in Genetics 5(6): 185–189.
Doel et al, Nucleic Acids Research 8(1980) 4575–4592.
Hein et al, Nucleosides & Nucleotides 7(1988) 497–510.
Cserpan et al, Acta Chemica Scandinavica 45(1991) 265–272.
McClain et al, Nucleic Acids Research 14(1986) 6770.
Kempe et al., Gene 39(1985) 239–245.

*Primary Examiner*—Mindy Fleisher
*Assistant Examiner*—Nancy J. Degen
*Attorney, Agent, or Firm*—Flehr Hohbach Test Albritton & Herbert LLP

[57] ABSTRACT

Methods are provided for the production of large polypeptides containing repeating sequences of amino acids utilizing biochemical techniques, specifically DNA sequences coding for the expression of the large polypeptides. Systems utilizing exogenous transcriptional and translational regions to control the production of the large polypeptides are also provided.

20 Claims, 10 Drawing Sheets

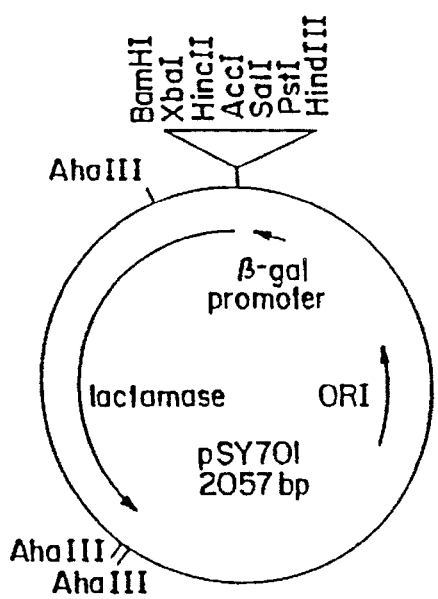
FIG._1

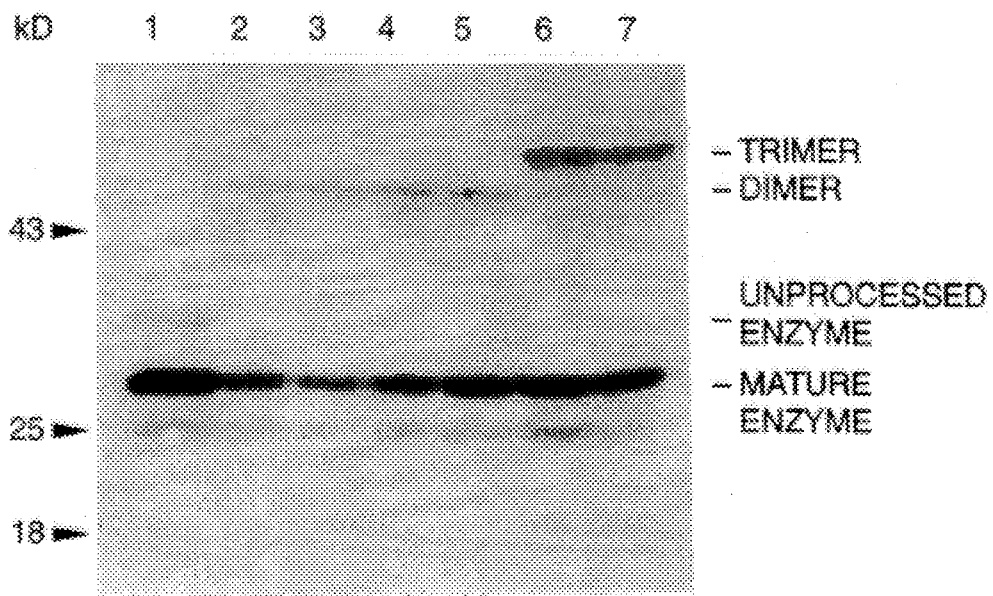
FIG._2A
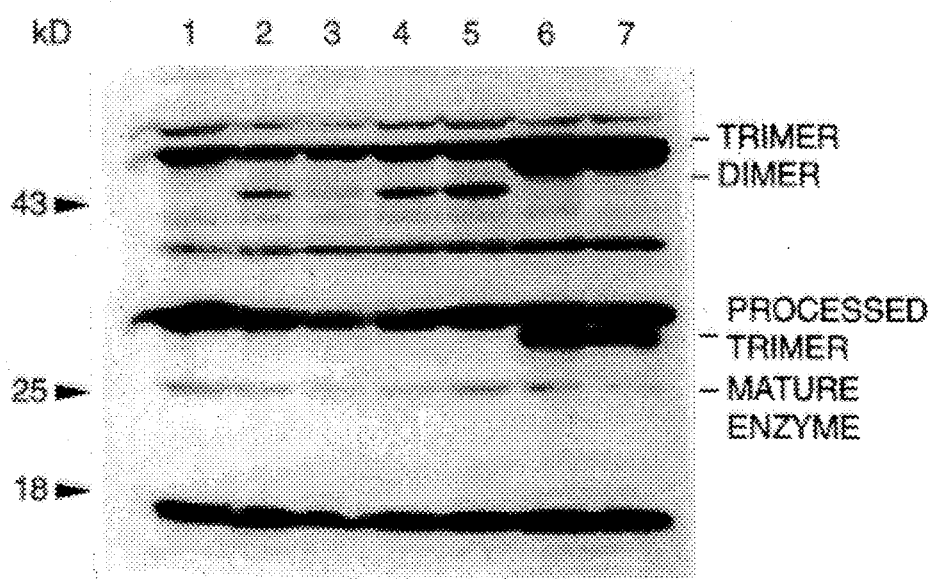
FIG._2B

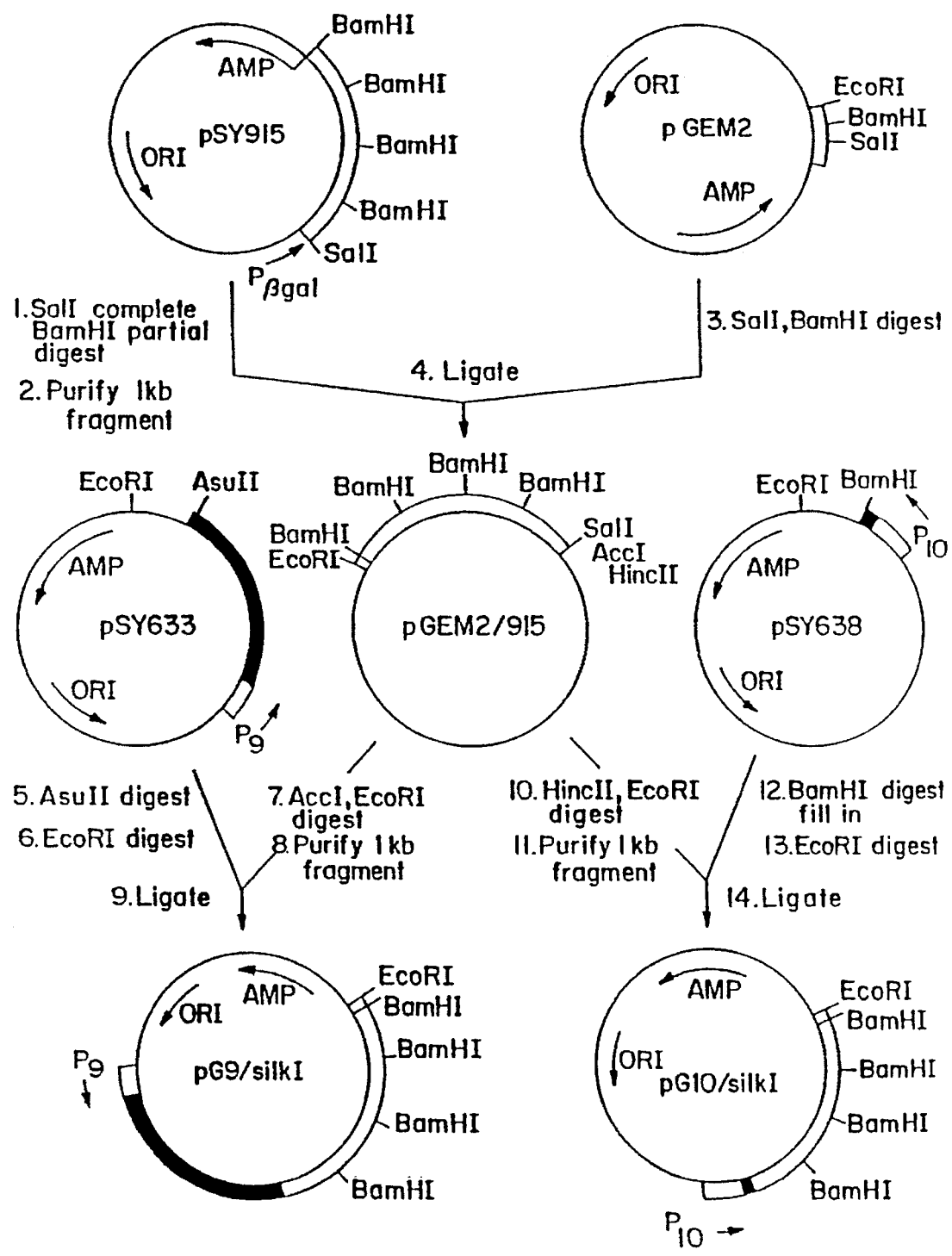
FIG._3

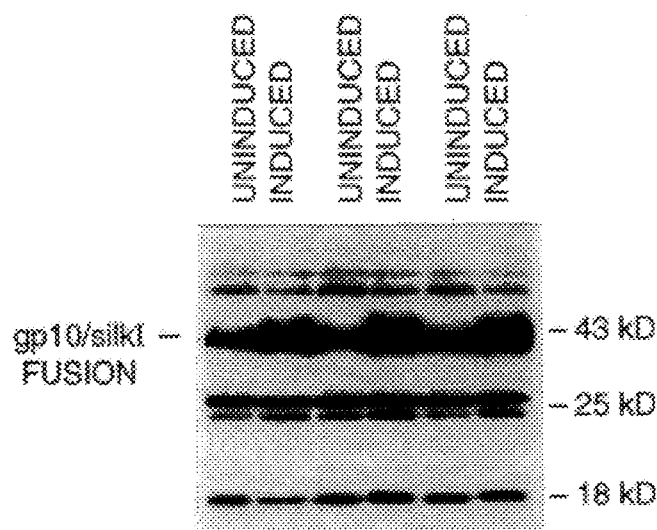
FIG._4A
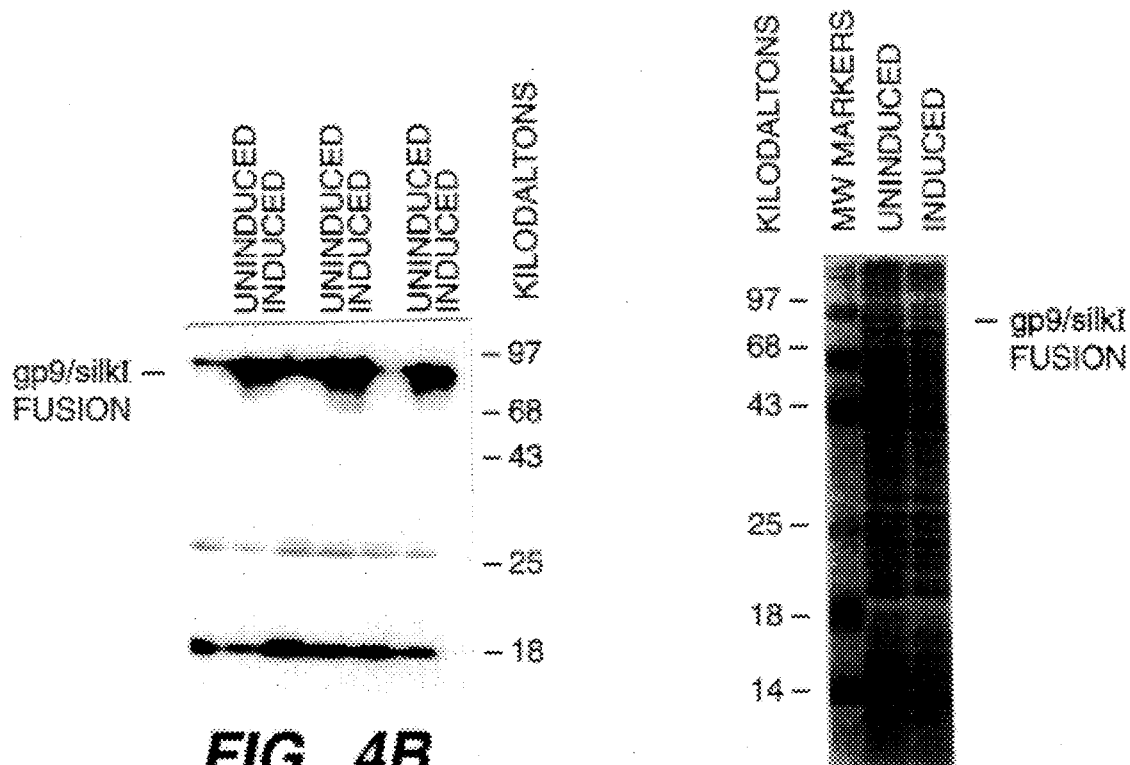
FIG._4B
FIG._4C

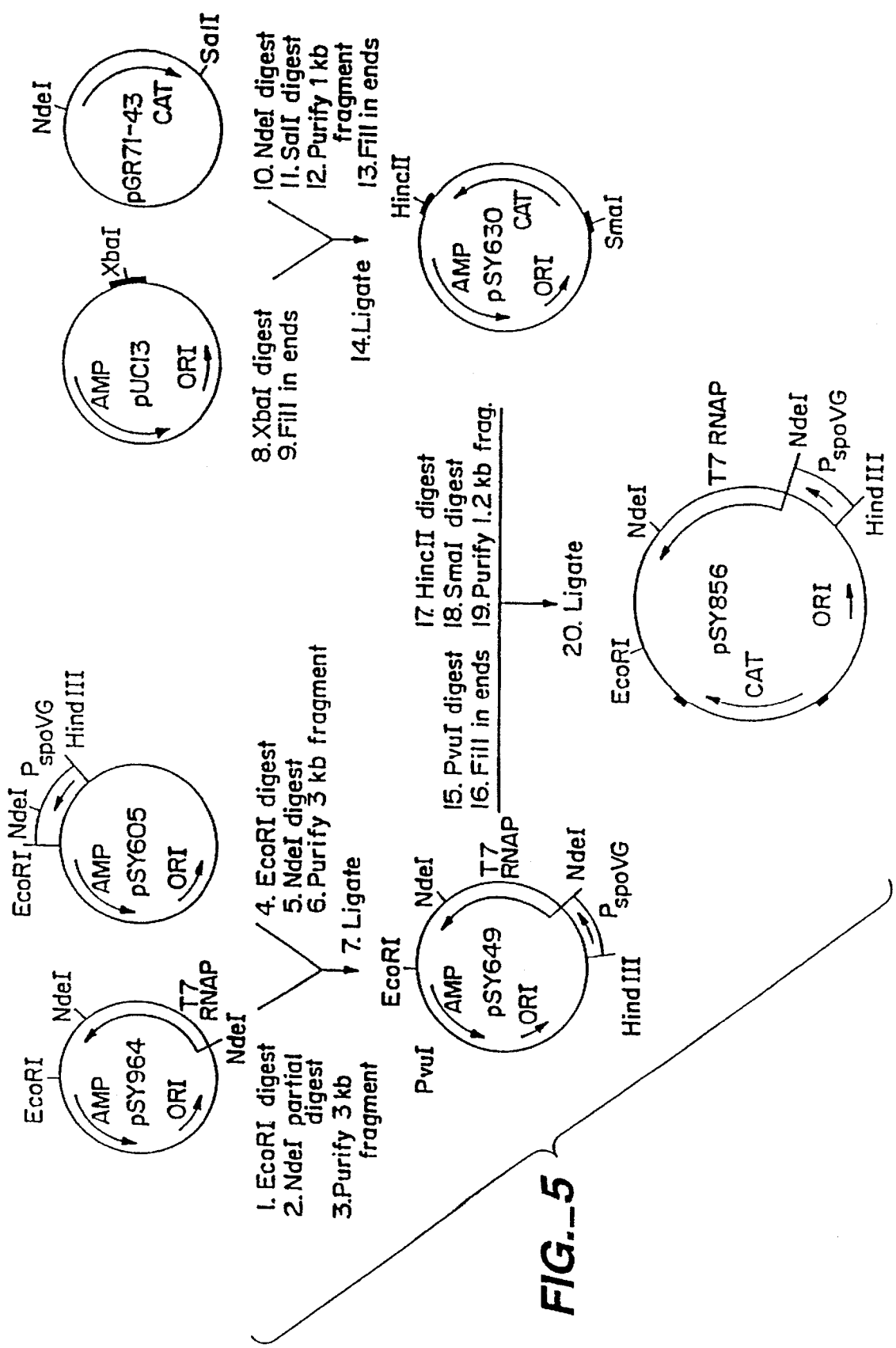
FIG._5

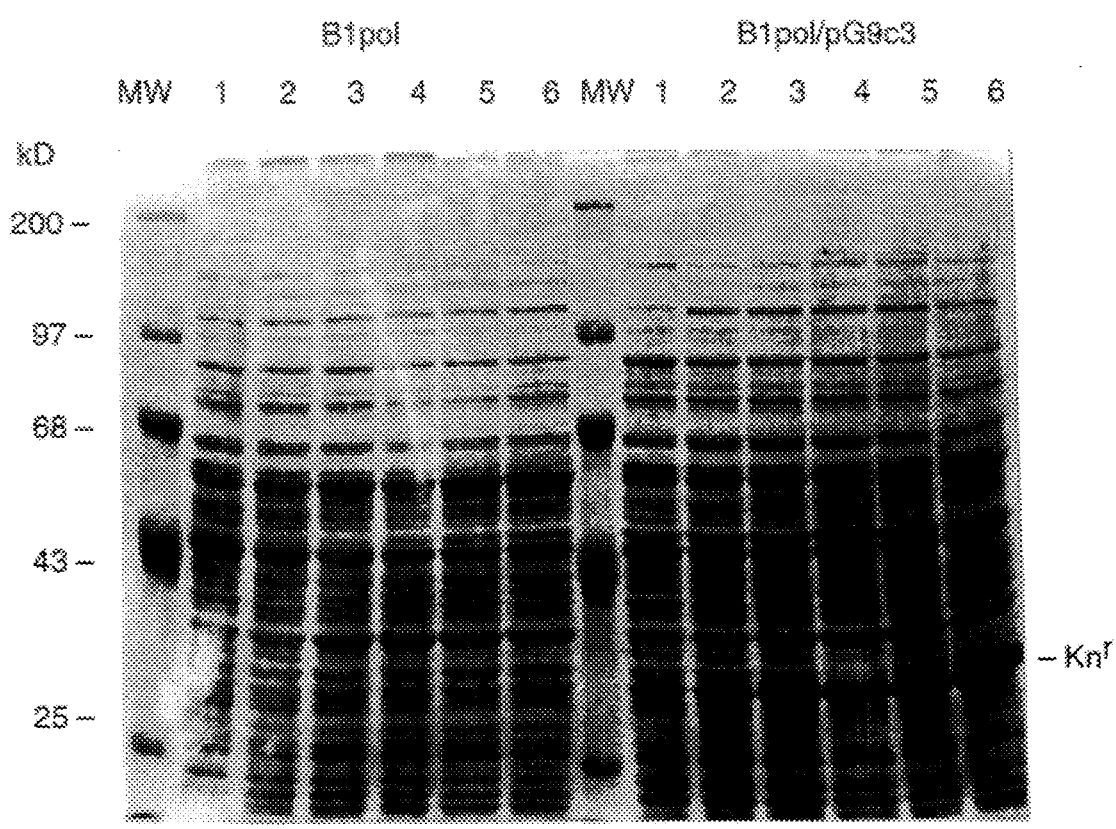
FIG._6

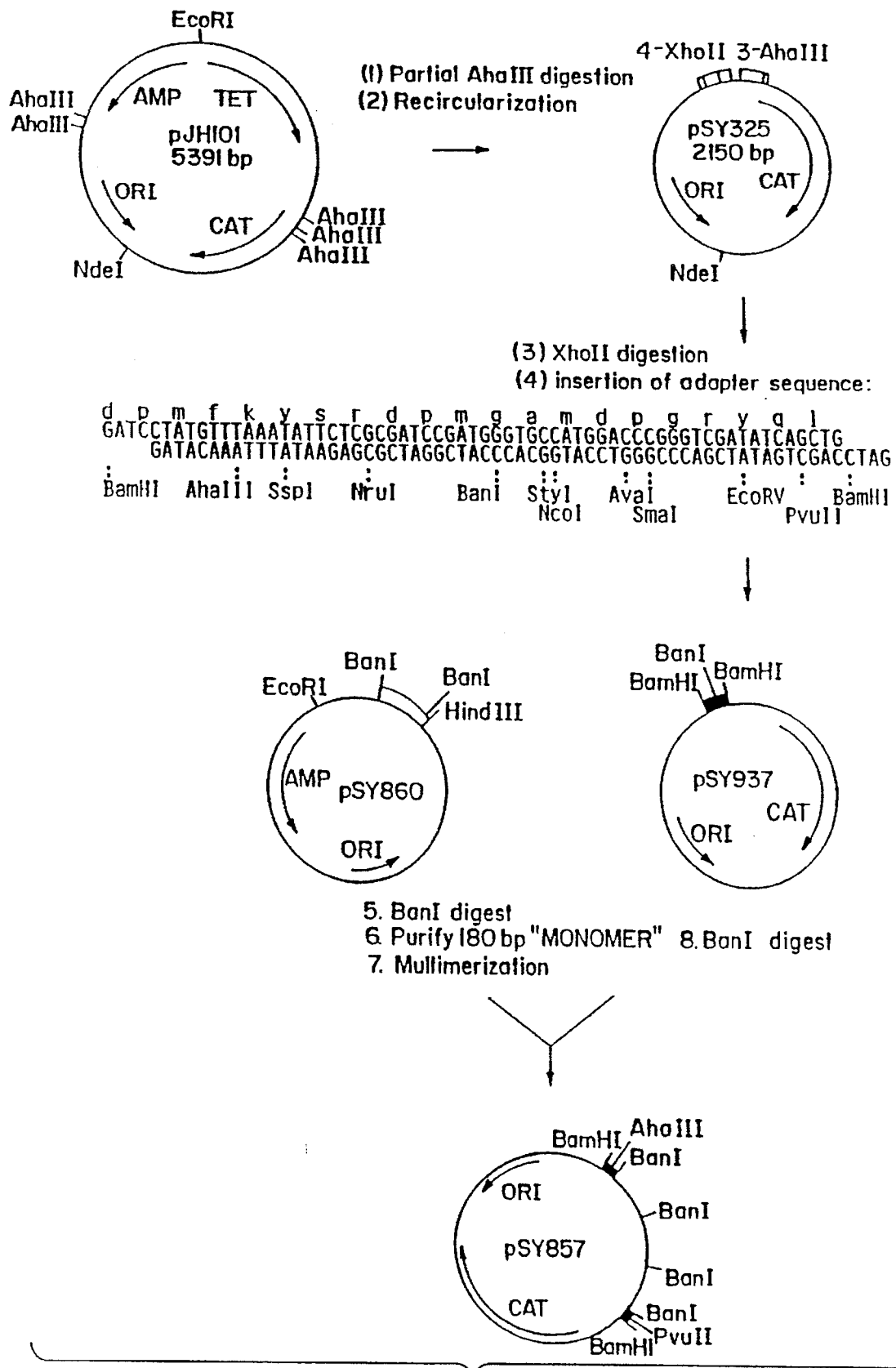
FIG._7

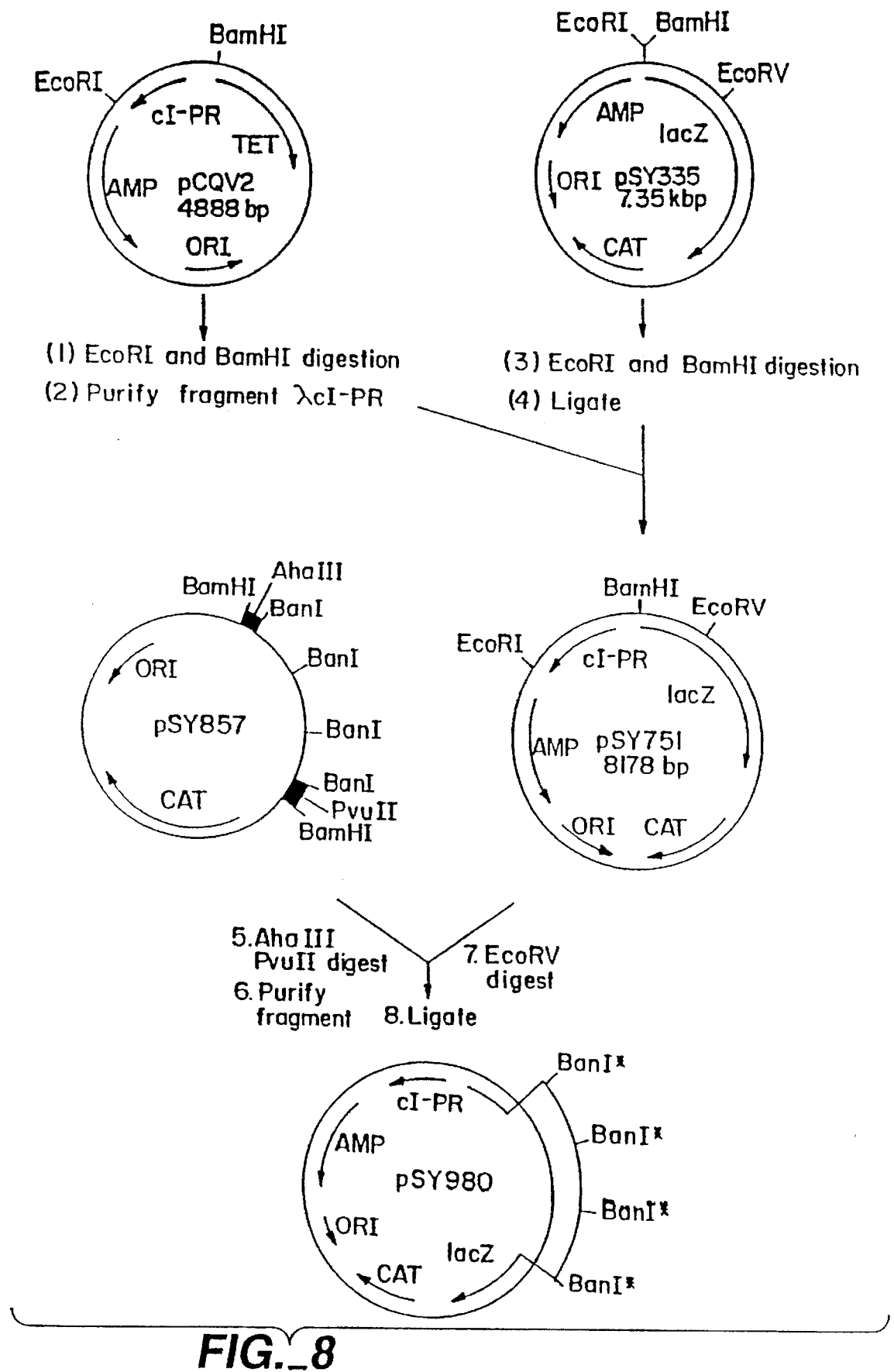
FIG._8

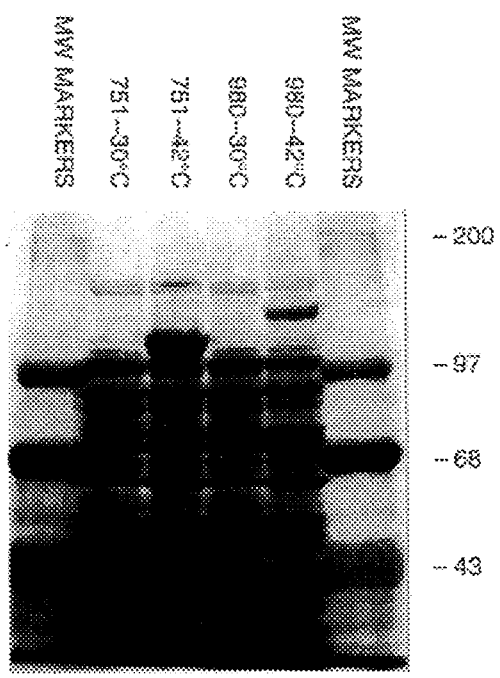
FIG._9A
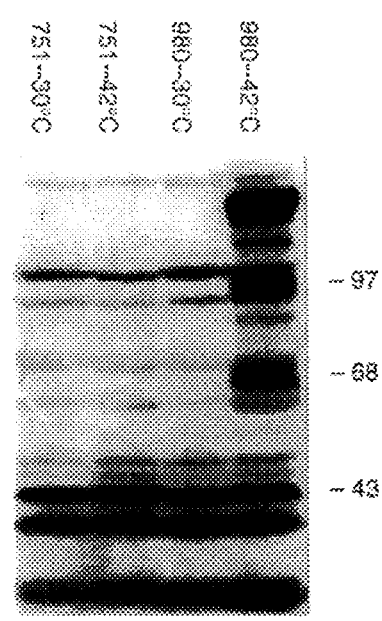
FIG._9B

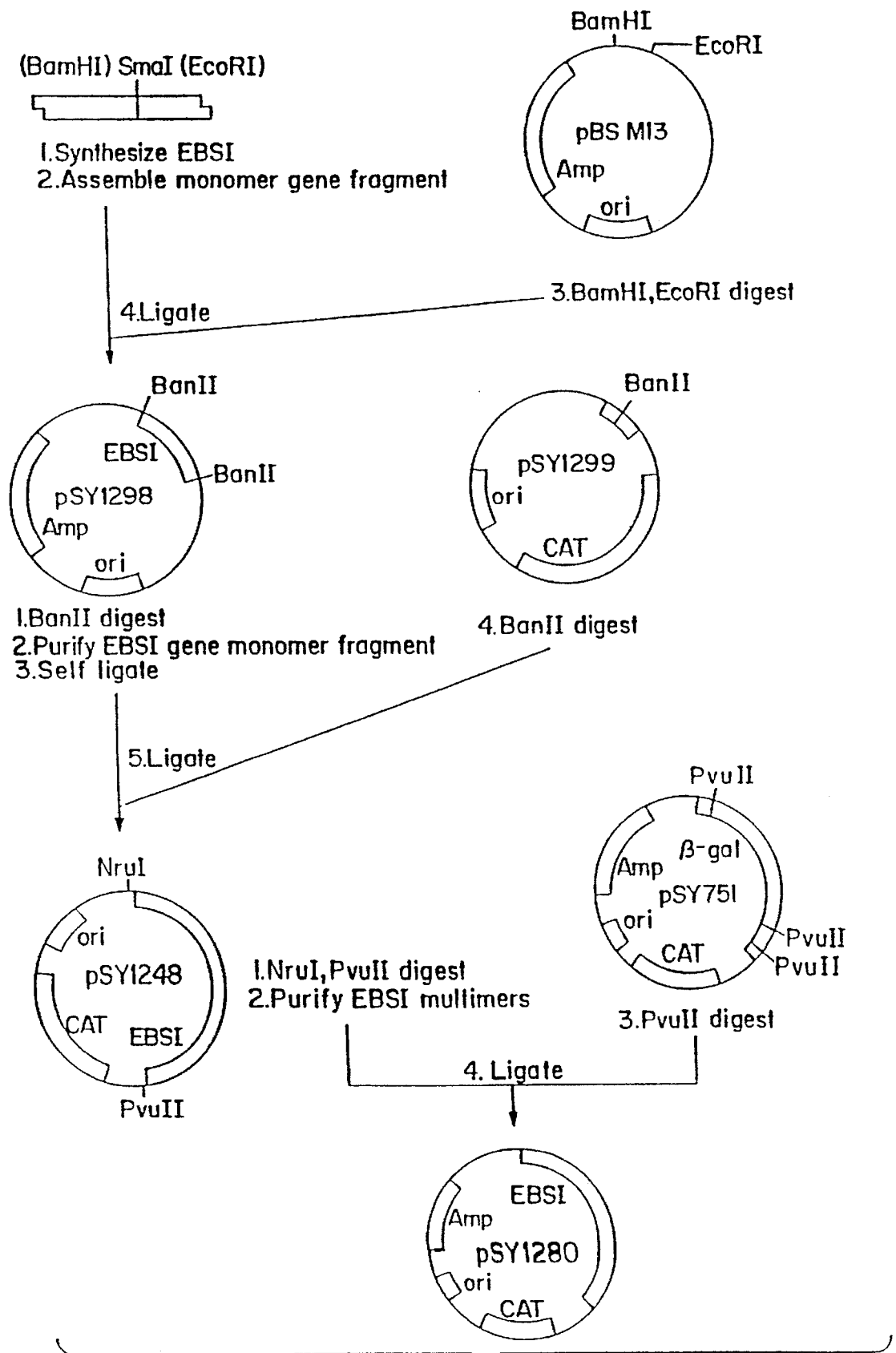
FIG._10

METHODS FOR PREPARING SYNTHETIC REPETITIVE DNA

CROSS-REFERENCE TO RELATED APPLICATIONS

This application is a continuation-in-part of application Ser. No. 08/053,049, filed Apr. 22, 1993, now abandoned, which application is a continuation of application Ser. No. 07/114,618, filed Oct. 29, 1987, now U.S. Pat. No. 5,243, 038; and a continuation in part of U.S. application Ser. No. 07/609,716 filed Nov. 6, 1990 now U.S. Pat. No. 5,514,583, which application is a continuation in part of application Ser. No. 07/269,429, filed Nov. 9, 1988, now abandoned, which is a continuation in part of application Ser. No. 07/114,618, filed Oct. 29, 1987, now U.S. Pat. No. 5,243,038, which is a continuation-in-part of application Ser. No. 06/927,258, filed Nov. 4, 1986, now abandoned.

The government has certain rights in this invention as a result of support provided by the Department of the Navy for the work leading to the present invention.

INTRODUCTION

TECHNICAL FIELD

The field is related to the production of high-molecular-weight polymers, either nucleic acids or peptides that are the expression products of the nucleic acids, and is particularly related to the production of high-molecular-weight peptides containing repeating sequences by biochemical processes, the peptides finding use as structural materials.

BACKGROUND

Recombinant DNA technology has been applied in the isolation of natural genes and the expression of these genes in a variety of host cells. Typically, this technology has had utility in producing biologically active polypeptides, such as interferons or peptide hormones, which were impractical to produce in useful amounts by other means. It was also possible to produce modified proteins by isolating natural genes and utilizing the techniques of site specific, in vitro mutagenesis to alter these genes and thereby change the polypeptides produced. Other polypeptides have been created by combining sections of various native genes to produce new polypeptides that are chimeric molecules of the several naturally occurring molecules.

With the advent of efficient and automated methods for the chemical synthesis of DNA, it has become possible to synthesize entire genes and to modify such synthetic genes at will during the course of synthesis. However, these various technologies have been applied to the production of natural or modified versions of natural polypeptides. There have been very few attempts to use these technologies to create substantially new polypeptides. In nature, polypeptides have a wide range of chemical, physical and physiological characteristics. Nevertheless, there are commercial applications for which known, naturally occurring polypeptides are not appropriate.

While biotechnology is versatile, usually it has been limited in its applications to naturally occurring products or modifications of naturally occurring molecules. One great strength of organic chemical synthesis, by contrast, has been the ability to transform inexpensive carbon materials to a wide variety of polymeric molecules, including naturally occurring molecules, but most importantly entirely new chemical structures, such as polypropylene and polyacrylates, which have defined and predicted chemical properties not associated with naturally occurring molecules.

Such materials, particularly high-molecular-weight polymers containing repeating sequences of amino acids, have proven difficult to produce by biochemical means. The genes necessary for producing large peptides containing repeating units of amino acids were unstable and often underwent intermolecular recombination causing deletions of repeating units in the gene. The development of a biotechnology which would produce polymeric molecules by biological processes similar to those available by organic synthesis would significantly broaden the range of applications of biotechnology.

BRIEF DESCRIPTION OF THE RELEVANT LITERATURE

The cloning of multiple lactose operators up to four in tandem is disclosed by Sadler et al., Gene, (1980) 8:279–300. Hybrid bacterial plasmids containing highly repeated satellite DNA is disclosed by Brutlag et al., Cell, (1977) 10:509–519. The synthesis of a poly(aspartyl-phenylalanine) in bacteria is disclosed by Doel et al., Nucleic Acids Research, (1980) 8:4575–4592. A method for enriching for proline content by cloning a plasmid which codes for the production of a proline polymer was disclosed by Kangas et al., Applied and Environmental Microbiology, (1982) 43:629–635. The biological limitations on the length of highly repetitive DNA sequences that may be stably maintained within plasmid replicons is discussed by Gupta et al. in Bio/Technology, p. 602–609, September 1983.

SUMMARY OF THE INVENTION

Methods are provided for the production of protein polymers having extended stretches of small amino acid repeating units by expression of a synthetic gene. The amino acid repeating units are sequences that provide a motif for the protein polymer and comprise a major portion of the gene encoding the protein polymer. There may be more than one type of amino acid repeating unit in a single protein polymer. According to the design of the protein polymer, one or more different amino acid repeating units and, optionally, one or more amino acid interrupting linker or spacer sequences are organized into a "monomer." In the final protein polymer, the amino acid monomer is sequentially replicated to achieve the desired molecular weight.

To construct the gene encoding the protein polymer, a DNA monomer sequence encoding the amino acid monomer sequence is first designed and synthesized. There are three different approaches to synthesizing the DNA monomer: (1) synthesizing a plurality of dsDNA segments, which when ligated correspond to desired DNA monomer sequence. Each dsDNA segment will typically encode a few amino acid repeating units, although the segment may encode an amino acid interrupting linker or spacer sequence. The dsDNA segments are synthesized by synthesizing single stranded oligomers which at least partially overlap and hybridizing pairs of oligomers to provide dsDNA, where each individual segment has a 3' terminus complementary to the 5' terminus of a second segment, and so forth. The dsDNA monomer is then assembled by cloning in a cloning vector a first dsDNA segment and characterizing such first segment; sequentially or simultaneously inserting additional dsDNA segments into the cloning vector in reading frame and optionally characterizing the resulting combination of segments, whereby a monomer is obtained, which monomer is sequenced; or (2) synthesizing a single strand of the DNA monomer and making the complementary strand, conveniently using the polymerase chain reaction, and characterizing the monomer, which is sequenced; or (3) using the appropriate restriction enzymes, combining all or part of DNA monomers previously prepared as in (1) and/or (2) above, optionally including new dsDNA segments synthesized as above, and characterizing the monomer. In those cases where new DNA is synthesized and introduced into a monomer, at least the new DNA and usually the entire monomer, will be sequenced. The monomers have predetermined termini for oligomerization. The monomer is then concatenated or oligomerized under ligating conditions to form multimers of the monomer, where the multimers may have different numbers of monomers resulting in a plurality of genes having different numbers of monomers. At least one multimer is inserted into an expression vector for introducing the vector into an appropriate expression host for expression of the gene. The expression host is then grown under conditions whereby the protein is expressed and may be isolated.

BRIEF DESCRIPTION OF THE FIGURES

FIG. 1: Plasmid pSY701 structure.

FIG. 2A–B: Immunoblots of polypeptide products using antibody to (A) beta-lactamase or to (B) gly-ala-peptide.

FIG. 3: Construction flowchart for plasmid pG10/SlpI.

FIG. 4A–C: Immunoblots of polypeptide products (A) T7gp10/SlpI with anti-Slp Ab, (B) T7gp9/SlpI with anti-Slp Ab, or (C) staining with Coomassie blue.

FIG. 5: Construction flowchart for plasmid pSY856.

FIG. 6: Time course for accumulation of the kanamycin-resistance gene product with the T7 system.

FIG. 7: Construction flowchart for plasmid pSY857.

FIG. 8: Construction flowchart for plasmid pSY980.

FIG. 9A–B: (A) Amido black stain or gel containing the product of beta-galactosidase/SlpIII gene fusion; (B) immunoblot of same product with anti-Slp antibody.

FIG. 10: Construction flowchart for plasmid pSY1280.

DESCRIPTION OF SPECIFIC EMBODIMENTS

Novel polypeptides are provided which are block polymers of repeating, relatively short, amino acid sequence units. The blocks of repeating units (oligomers) may be linked by spacers of different amino acid sequences. The polypeptides may contain only one or a plurality of repetitive amino acid sequences (having the same or different amino acid sequence). The novel polypeptides are particularly useful as fibrous or structural proteins, including crystalline, elastomeric, tough and bony materials, e.g. proteins similar to, but different from, silk, elastin, collagen, keratin, or other naturally occurring structural polymers having a repetitive amino acid sequence motif. The gene encoding the repeating-unit-containing peptides is produced to particularly avoid problems previously associated with genes containing multiple repeating units of DNA.

Genes produced according to the methods described herein will generally be at least 900 nt in length, usually at least 1200 nt in length, preferably at least 1500 nt in length, usually not more than 20 knt in length, more usually not more than 12 knt in length, frequently not more than about 6 knt in length. This will usually result in a protein of at least about 10 kDal, usually at least about 30 kDal, and more usually at least 35 kDal, and not more than about 200 kDal, more usually not more than about 125 kDal. The methods for production of the synthetic genes encoding the protein polymer involve preparation of a dsDNA "monomer", which is an extended segment of DNA principally encoding amino acid repeating units, where the dsDNA monomer is generally a repeating segment of the final product, where the final product will have from 2, frequently at least 3, and up to 50, usually not more than about 20, more usually not more than about 10, monomeric units. There is one exception, to be described below, where the monomer may be the entire final repeating unit gene. The monomer will be a dsDNA whose sequence is, with one exception, established prior to its multimerization to provide the gene.

The size of the dsDNA monomer is dependent upon the desired amino acid monomer sequence as well as the way in which the monomer is obtained. If the monomer is constructed using any newly synthesized and ligated DNA, then the monomer is always sequenced prior to multimerization and the practical limitations of DNA sequencing technology limit the monomer size to about 500 nt, usually about 400 nt. If the gene monomer is constructed solely from digestion fragments of previously constructed and sequenced monomers, then the final gene monomer is typically characterized by restriction digests. Therefore, the gene monomer can be as large as the final gene, depending upon the desired amino acid repeating unit sequences and periodicity.

There are three ways to obtain the monomer. The first way relies on synthesis and assembly of single stranded deoxynucleotide oligomers into a dsDNA monomer sequence encoding from about 1 to 12, more usually 1 to 9, frequently 1 to 6, repeating amino acid units. Each repeat unit will have about 3 to 36 codons, generally about 3 to 30 codons (9 to 90 bases), usually about 3 to 25 codons, more usually about 3 to 10 codons, frequently not more than 8 codons, particularly when mimicking a naturally occurring motif. The number of amino acid repeat units in a dsDNA monomer sequence will depend to a substantial degree on the size of the repeating unit. Conveniently, oligomers may be prepared having from about 15 to 120 bases, usually about 21 to 90 bases, more usually about 39 to 72 bases, although oligomers may be prepared with up to 300 bases, more usually up to about 252 bases. For repeating units having a few amino acids, usually in the range of 3 to 8 amino acids, more usually in the range of 2 to 10 amino acids, the single stranded oligomer will conveniently have from about 2 to 10 amino acid repeating units.

The number of different single stranded oligomers will usually be at least 2, forming 1 pair, more usually at least 6, forming 3 pairs, or may be 8 or more, forming 4 or more pairs, where the protein polymer has the same repeating unit. Where block copolymers are prepared, the number of oligomers will depend on the number of different blocks and the size of the blocks. Each pair of oligomers are complementary and at least partially overlap, providing blunt or cohesive (protruding) ends, preferably protruding ends, to allow for ease of assembly and ligation of the dsDNA to form a "monomer". By having a multiplicity of dsDNA segments, the termini may be designed that the first segment has a 3' terminus complementary to the 5' terminus of a second segment, and so on, where the termini may have different consensus sequences for different restriction enzymes or not be recognized by any known restriction enzyme. The dsDNA segments formed by the pairs of oligomers of the different ssDNA oligomers may encode the same amino acid sequence or a different amino acid sequence, but where more than one dsDNA segment is synthesized, at least two segments will have different nucleotide sequences. By having different termini at each end of each dsDNA segment, the individual segments cannot oligomerize, even if they have been phosphorylated. In this way, when the different segments are combined, the ends of the combination of the segments may have complementary termini, so that they can be oligomerized.

A first dsDNA segment is desirably cloned in a prokaryotic vector by linearizing a vector having an origin of replication and convenient restriction sites, which may involve a polylinker, for insertion of the dsDNA segment. The vector will also have a marker gene for selection, which will usually impart antibiotic resistance, but may afford another distinguishing characteristic, e.g. chromophore or fluorophore formation. The marker will preferably provide antibiotic resistance, there being a wide variety of antibiotic reagents, e.g. tetracycline, chloramphenicol, actinomycin, neomycin, ampicillin, hygromycin, heavy metals, etc. Other markers include β-galactosidase, which, with the substrate X-gal, provides a blue color. Numerous vectors are commercially available for cloning in $E.\ coli$ and need not be exemplified here. The vector is then introduced into an appropriate cloning host by any convenient means, including calcium phosphate precipitated DNA, fusion, transfection, conjugation or the like. The cells are then grown in an appropriate selective nutrient medium. Surviving cells are harvested, lysed and the plasmid isolated.

After cloning, the first dsDNA segment is characterized, such as by restriction analysis and sequencing. Where the dsDNA segment is relatively small, sequencing can be performed rapidly and substantially error free.

The termini of the dsDNA segments may be selected to have protruding 5' ends, protruding 3' ends, or a protruding 5' and a protruding 3' end on the same strand, either the coding strand or the non-coding strand. Complementation of the protruding ends may destroy the sequence of the restriction site or retain the sequence, when different dsDNA segments are ligated. In selecting DNA sequences, one selects the terminal sequence to allow for linearization of the vector and insertion of the next dsDNA segment, without cleavage within the gene being formed.

Once the first dsDNA segment has been shown to have the correct sequence, the vector may then be used in the next stage in the preparation of the gene. The vector is linearized at the 5' or 3' terminus of the first dsDNA segment cloned. By employing a polylinker in the vector at the 5' and/or 3' terminus of the dsDNA segment cloned, the vector may be digested by using a restriction enzyme which cleaves in the polylinker to provide a terminus at the 5' or 3' terminus of the vector complementary to the 3' or 5' terminus of the next dsDNA segment. Alternatively, one may use restriction enzymes which cleave an asymmetric consensus sequence or cleave distal from the consensus sequence. In this way the vector may be repeatedly cleaved and ligated, without cleavage of the gene. After cloning, the combined dsDNA segments may be characterized as described above. The process may be repeated until all of the dsDNA segments have been inserted and verified for sequence and being in the proper order and reading frame. Alternatively, each dsDNA segment comprising the monomer may be individually cloned and characterized. The individual dsDNA segments are then purified and ligated in a single cloning step to construct the monomer, which is sequenced. By appropriate choice of the restriction enzymes or polylinker, the termini of the monomer may have the same or different terminal restriction sites, but will have complementary ends, if the monomer is to be multimerized.

A second approach depends on the synthesis of a single strand of the monomer. Synthetic techniques allow reasonably accurate oligonucleotide synthesis of 300 bases or more. For the most part the single strand will be in the range of about 100 to 300 bases, usually in the range of about 100 to 250 bases. The single strand is then used to produce a complementary strand, conveniently using the polymerase chain reaction ("PCR") and the resulting dsDNA cloned, purified and sequenced to ensure that it has the correct sequence. Appropriate primers may be employed, which may serve to extend the termini for multimerization by introducing a new restriction site consensus sequence, introduce intervening sequences, or the like. The monomer prepared this way will have the same limitations as to size and the number of amino acid repeating units which are encoded as the monomer prepared by the sequential or simultaneous cloning of dsDNA segments.

After the monomer has been prepared, characterized and the desired sequence confirmed, the monomer may then be excised from the vector and purified in accordance with conventional procedures. At this time the "monomer" synthesis has been completed. The monomer may then be used to produce the gene.

The third approach relies on the use of fully characterized dsDNA which is already present in a monomer, previously prepared by either of the methods described above. Using this approach allows for great flexibility in constructing new monomers, particularly where copolymers comprising different amino acid repeating units are desired. Using the appropriate restriction enzymes, all or part of the dsDNA comprising a monomer may be purified. Then, the desired dsDNA from two or more separate monomers may be combined to construct a new monomer encoding the amino acid repeating units of interest. The digested monomer DNA fragments which are to be combined may have complementary or non-complementary ends. If the termini of the monomer sequences are not complementary, as required, the termini may be made so by employing adapters, filling in, nuclease digestion, or the like. Once the appropriate monomer sequences have been cloned together, either sequentially or simultaneously, to make the new monomer, the monomer is then characterized and sequenced, if necessary. If newly synthesized adapters or filling in reactions or nuclease digestion or the like are employed, the region comprising the modified monomer DNA is sequenced.

When the protein product is a homooligomer of the monomer, desirably the termini have cohesive ends and may retain the same restriction site consensus sequence or result in a sequence other than the consensus sequence.

As evidenced by the above description, the monomer is a molecule having a plurality of dsDNA segments, normally having at least two different dsDNA segments, which may or may not encode the same amino acid sequence, but generally providing for blocks of the same pattern of repeat amino acid units throughout the final polymer gene. (The exception is when the monomer is the gene.) Thus the monomer may provide for a homopolymer, copolymer, or polymer having a defined motif, where the amino acid repeating units vary, e.g. collagen.

The monomer is then multimerized by ligation, conveniently employing from about 0.01 to 100 μg of the monomer under ligating conditions, where multimers having different numbers of monomers are obtained. The multimers may then be segregated by size, selecting multimers of a predetermined size. Any of the original mixture, the partially purified mixture, or size segregated fractions thereof, may then be introduced into a vector. Either an adapter vector or an appropriate expression vector is employed. The adapter vector has a polylinker which will allow for insertion into the polylinker, so as to be capable of being read in any reading frame. In this way one may introduce different unique restriction sites which allow for excision and transfer of the multimer gene from the expression vector. The multimer gene may be characterized and purified before transfer to the expression vector. The multimer will have appropriate termini which will allow for insertion into the vector and, as appropriate, have end groups which are present in the vector or be inserted with termini which will allow for the exact excision of the gene. One may select a particular sized multimer or a plurality of multimers of different size for expression, so that one has a family of protein polymers, sharing the same repeating motif.

The expression vector will be characterized by having an origin of replication which is functional in an appropriate expression host, usually for episomal maintenance, and a marker for selection. Markers as described above may find use. For unintegrated vectors or constructs, the origin of replication will usually provide for multicopies, usually greater than about 5 copies on the average. The expression vector will also have a promoter which is functional in the expression host. Various promoters can find use, which provide for a high level of transcription, either inducible or constitutive transcription. Illustrative promoters include β-lactamase, β-galactosidase, $\lambda P_L$ or $\lambda P_R$ promoters, trpE promoter, trp-lac promoter, T7 promoter (particularly genes 9 and 10), $cI^{ts}$, etc. The multimer gene and the linearized vector may be combined under hybridizing, usually including ligating, conditions. Where the multimer gene does not have an initiation codon, such a codon can be added. More conveniently, the multimer gene may be inserted into a coding sequence present in the vector, under the transcriptional control of a promoter. The coding sequence in the vector will generally not exceed 200 bp, usually not exceeding about 60 bp, where the site into which the multimer gene is inserted has the coding sequence and multimer gene in proper reading frame. Generally, the coding sequence present in the vector will be not more than about 20%, usually fewer than about 10%, preferably fewer than about 5% of the total number of bases in the coding sequence.

A signal sequence may be present at the 5' terminus of the coding sequence to allow for secretion of the protein polymer into the periplasmic space or with many hosts into the nutrient medium. For the most part, the product will be produced intracellularly.

Instead of a vector, DNA constructs may be employed for transformation of the expression host, with integration of the construct into the genome of the expression host. The construct will differ from the vector primarily by lacking an origin which provides for episomal maintenance. Thus, the construct will provide at least transcriptional and translational initiation and termination regions, the gene encoding the protein polymer between the initiation and termination regions and under their regulatory control, a marker for selection as described above, and other functional sequences, such as homologous sequences for integration into the host genome, sequences for priming for the polymerase chain reaction, restriction sites, and the like.

For the most part, the expression host will normally be unicellular, prokaryotic or eukaryotic, but may be from a multicellular organism. The organism may be selected from bacteria, algae, fungi, insect cells, plant cells, etc. Illustrative hosts include *E. coli, B. subtilis, B. stearothermophilus, S. cerevisiae,* and the like.

The expression host is then grown in accordance with conventional ways in an appropriate medium in culture, e.g. fermentation. After the cells have been grown to an appropriate density, the cells may be harvested, lysed and the product isolated by appropriate means, in accordance with the physical and chemical characteristics of the product. In some instances, the product is insoluble at moderate temperatures in an aqueous medium, and may be purified by detergent extraction at mildly elevated temperatures, above about 60° C. (See U.S. Pat. No. 5,235,041.) As appropriate, the crude or purified product may then be used for its intended purpose.

The genes of the subject invention generally comprise concatenated monomers of DNA encoding the same amino acid sequence, where all or part of two or more different monomers encoding different amino acid repeating units may be joined together to form a new monomer encoding a block copolymer. The individual amino acid units will have from about 3 to 30 amino acids (9 to 90 nt), usually 3 to 25 amino acids (9 to 75 nt), more usually 3 to 15 amino acids (9 to 45 nt), usually having the same amino acid appear at least twice in the same unit, generally separated by at least one amino acid. In some instances, the minimum number of amino acids will be 4. Within a monomer, dsDNA encoding the same amino acid repeating unit may involve two or more nucleotide sequences, relying on the codon redundancy to achieve the same amino acid sequence.

For the most part the DNA compositions of this invention may be depicted by the following formula:

$$K_k (W M_r X_x N_s Y_y)_i L_l$$

wherein:

K is a DNA sequence encoding an amino acid sequence of from about 1 to 125 amino acids, usually 1 to 60 amino acids, which may be any sequence depending upon the manner of preparation of the construct and the purpose of the protein product, generally being fewer than about 20% of the total number of amino acids, more generally being fewer than about 10% of the total number of amino acids, which may be any sequence, particularly a naturally occurring sequence where the multimer structural gene has been fused to another DNA sequence in reading frame. K, if present, will have the initiation methionine codon. L may be the same or different from K, coming within the definition of K, but lacking the initiation methionine codon;

k and l are the same or different and are 0 or 1;

W has the formula:

$$[(A)_n (B)_p]_q$$

wherein:

A is a DNA sequence coding each time that it appears for the same amino acid repeating unit normally having at least one amino acid appear at least twice in the sequence, where A will generally be from about 9 to 90 nucleotides (nt), more usually from about 9 or 12 to 75 nt, preferably from about 9 or 12 to 45 nt, more preferably from about 9 or 12 to 30 nt;

where there will usually be at least two different A's, usually not more than ten different A's, more usually not more than six different A's, which code for the same amino acid sequence but differ from each other by at least one nucleotide and may differ by as many as ten nucleotides, usually not differing by more than about five nucleotides from another A sequence, each of the different A's usually being repeated at least twice; at least two different codons are employed for the same amino acid, e.g., GGC and GGA for glycine, in different A's coding for the same amino acid sequence unit;

n will be an integer of at least 2, usually at least 4, more usually at least about 8, and not more than about 250, usually not more than about 200, frequently not more than about 125, and in some instances may not exceed about 50;

B is a DNA sequence different from A coding for an amino acid sequence other than the amino acid repeating unit coded by the A unit and serves as a linking unit between oligomers of A units. B will generally have from about 3 to 45 nt (1 to 15 amino acids), more usually from about 3 to 30 nt (1 to 10 amino acids);

where the B units appearing in the gene may be the same or different, there usually not being more than about 10 different B units, more usually not more than about 5 different B units, where the B units may differ from about 1 to 45 nt, more usually from about 1 to 15 nt, where the different B's may code for the same or different amino acid sequence;

p is 0 or 1 and may differ each time there is a successive A unit;

q is an integer of at least 1 and will vary with the number of nucleotides in A and B, as well as the values of n and p. The variable q will be selected so as to provide for at least 90 nt for each multimeric portion of the structural gene, preferably at least about 150 nt, more preferably at least 450 nt, and most preferably at least 900 nt, and the number of nucleotides will usually not exceed about 10,000 nt, more usually not exceeding about 8,000 nt, generally being in the range of about 900 to 6,000 nt, more usually to about 5,000 nt; and M is a DNA nucleotide sequence of 12 to about 150 nt, usually being 18 to 150 nt, more usually not more than about 90 nt, which may encode any amino acid sequence, usually encoding a functional sequence which provides for a natural or synthetic sequence resulting in a biological or chemical function or activity;

r and s are the same or different, being 0 to 3, usually 0 to 2, depending on whether a functional group is present in the polymer, usually being 1 to 2, where different, the same or similar functional groups may be combined in a contiguous manner;

N is the same as or different from M and comes within the same definition as M;

X may be the same as or different from W, usually different, and will have the formula $$[(A^1)_n 1 \ (B^1)_p 1]_q 1$$

wherein:
$A^1$, $B^1$, $n^1$, $p^1$ and $q^1$ are the same as or different from A, B, n, p and q respectively, at least one being different, wherein the analogous symbols come within the same definition as their counterparts;

x is 0 or 1;

Y may be the same as or different from W, usually different, and will have the formula $$[(A^2)_n 2 \ (B^2)_p 2]_q 2$$

wherein:
$A^2$, $B^2$, $n^2$, $p^2$ and $q^2$ are the same as or different from A, B, n, p and q respectively, at least one being different, wherein the analogous symbols come within the same definitions as their counterparts.

y is 0 or 1;

i is 1 to 100, usually 1 to 50, more usually 1 to 30, particularly 1, when x, y, r and s are 0;

when x or y is 1, q, $q^1$ and $q^2$ will be a total of at least 2, usually at least 5 and not more than about 50, usually not more than about 33.

The total number of nucleotides will be at least 900 nt, usually at least about 1200 nt, preferably at least about 1500 nt and may be 20 knt (kilonucleotides), usually not more than about 12 knt, more usually not more than about 6 knt, and frequently not more than about 4 knt.

The polypeptide encoded by the above DNA sequence will have the following formula:

$$K_k'(W'M_r'X_x'N_s'Y_y')_i L_l'$$

wherein:
W' will have the following formula $$[(D)_n \ (E)_p]_q$$

wherein:
D is the amino acid sequence encoded for by A and therefore has the numerical limitations based on 3 nucleotides defining a codon that codes for one amino acid;

E is the amino acid sequence encoded for by B, and therefore has the numerical limitations based on 3 nucleotides defining a codon, where each E may be the same or different, depending upon the coding of B;

and, wherein, likewise K', W', M', X', N', Y' and L' is the amino acid sequence encoded for by K, W, M, X, N, Y and L respectively. However, in the case of K and L, subsequent processing, such as protease treatment, cyanogen bromide treatment, etc. may result in partial or complete removal of the N- or C-terminal non-multimeric chains.

n, p, q, k, r, s, x, y, i and l have the same definitions as previously indicated.

Particular polymeric compositions having amino acid repeating units having the same compositions (A) will have the following formula where x and y are 0, $$K_k' \ [(D)_n \ (E)_p]_q \ L_l'$$

where all of the symbols have been defined previously; and the DNA sequence will have the formula $$K_k \ [(A)_n \ (B)_p] L_l$$

where all of the symbols have been defined previously.

Particular DNA sequences encoding copolymeric compositions having two to three repeating blocks will have the following formula $$K_k"(W"M_r"X_x"N_s"Y_y")_i L_l"$$

wherein:

W" is a multimer having the formula $$[(A^3)_n3 (B^3)_p3]_q3$$

where

A³ is of 3 to 15, usually 4 to 6 codons, otherwise coming within the definition of A;

n³ will be from about 2 to 40, usually 2 to 32;

B³ is of from 2 to 20, usually 4 to 6 codons;

p³ is 0 or 1;

q³ is of from about 2 to 50, usually 2 to 30, depending on the value of n³, as discussed previously for n and q;

X" and Y" are the same as or different from W", usually different, coming within the same definitions as W";

M" and N" come within the definitions of M' and N';

i" is at least 2, usually at least 5 and not more than about 75, usually not more than about 50, generally not exceeding 30;

with the other symbols as defined previously, wherein at least one of x and y is 1.

The compositions of the invention will usually have a molecular weight of at least about 30 kDal, usually 50 kDal, frequently at least about 60 kDal and may have molecular weights as high or higher than 500 kDal, usually not exceeding 300 kDal, more usually not exceeding about 250 kDal, and in many instances not exceeding 125 kDal, the higher ranges generally being the multimer combinations, with the individual multimer usually being less than about 150 kDal, usually less than about 100 kDal.

The nucleotide sequences which are employed will be synthesized, so that the repetitive units will have different codons for the same amino acid as described above. Usually, at least about 25%, more usually at least about 40%, and generally at least about 60%, but not greater than about 95%, preferably not greater than about 90% of the nucleotide sequences encoding the repetitive units will be the same. Greater diversity within those ranges will be employed where the initial constructs are experimentally shown to undergo spontaneous recombination events.

Of particular interest are polypeptides which have as a repeating unit SGAGAG (SEQ ID NO:01) (G=glycine; A=alanine; S=serine). This repeating unit is found in a naturally occurring silk fibroin protein, which can be represented as GAGAG(SGAGAG)₈SGAAGY (SEQ ID NO: 02) (Y=tyrosine). In the subject invention, the repeating unit is designed where the N-terminus may be MGAGAG or any other sequence of generally at least about 3 amino acids, usually at least about 5 amino acids, more usually 12 amino acids and not greater than about 125, usually not greater than about 100 amino acids, which may be different from the repetitive unit. Generally, a different N-terminus will be the result of insertion of the gene into a vector in a manner that results in expression of a fusion protein. Any protein which does not interfere with the desired properties of the product may provide the N-terminus. Particularly, endogenous host proteins, e.g. bacterial proteins, may be employed. The choice of protein may depend on the nature of the transcriptional initiation region. Similarly, the C-terminus may have an amino acid sequence different from the repeat sequence. Conveniently, there may be from 1 to 100, usually 1 to 25 amino acids, which may be the C-terminus of a naturally occurring structural gene, which again typically results from the formation of a fusion product.

A silk-like-protein (Slp) gene may be produced by providing oligomers of from about 5 to 25 repeat units as described above, more usually of about 10 to 20 repeat units. By having different cohesive ends, the oligomers may be concatemerized to provide for the polymer having 2 or more of the oligomeric units, usually not more than about 50 oligomeric units, more usually not more than about 30 oligomeric units, and frequently not more than about 25 oligomeric units.

The silk-like proteins may be varied by having alternate multimers with the same or different handedness. For example, in the formula, (B)ₚ may provide an even or odd number of amino acids. In silk, the hydrogens of the glycine may align on one side and the methyls and hydroxyls of alanine and serine on the other. If (B)ₚ is even, there will be continuous alignment, if odd, there will be alternating alignment of (A)ₙ. Thus, different properties can be achieved by changing the number of amino acids encoded by (B)ₚ.

Of particular interest are polypeptides which mimic the composition and physical properties of silks found in nature, e.g. *Bombyx mori*.

Also of interest are polypeptides which have as a base repeating unit GVGVP (SEQ ID NO: 03) (G=glycine, V=valine, P=proline), which may be found in naturally occurring elastin; also VPGVG (SEQ ID NO:04) and/or APGVGV (SEQ ID NO:05) units. In the subject invention, the N-terminus may be any convenient sequence and, if desired, may be in whole or in part removed by a protease. Usually the N-terminal sequence which does not have the subject motif will be less than about 100 amino acids, more usually less than about 60 amino acids.

Of particular interest is a base sequence of about 2 to 32, preferably 8, units separated by a sequence of about 3 to 50 amino acids, usually 12 to 48 amino acids, which may include an internal repeat of from 3 to 15 amino acids different from the basic repeating unit. For example, the second repeat sequence could be GAGAGS (SEQ ID NO:06), repeated twice. The total number of base repeating units will generally be in the range of about 150 to 500, usually 150 to 300, more usually 175 to 250. The C-terminus may terminate with a repetitive unit or portion thereof or a different sequence of from 1 to 125, usually 1 to 50 amino acids. The C-terminus is not critical to the invention and will be selected primarily for convenience. As with the N-terminus, it may be designed for proteolytic cleavage. As in the case of the silk protein, the subject elastin-like protein may be similarly engineered.

Of particular interest are proteins which mimic the properties of elastin and provide for elastomeric properties.

Of particular interest are collagen like proteins which have the sequence Gαβ, where α and β may be any amino acid, particularly one being proline. Usually in the protein α and β will be selected so that the total percent proline in the protein is between about 10 to 45 number % of the amino acids in the protein. The amino acids of particular interest other than glycine and proline are alanine, isoleucine, leucine, valine, serine, threonine, asparagine, glutamine, lysine, arginine, aspartic acid, glutamic acid, histidine. By known procedures after production of the protein, one or more prolines may be oxidized to hydroxyproline.

Also of interest are polypeptides which have as a repeating unit K-L-(1)-L-A-E-A (SEQ ID NO:07) where 1 is a basic or acidic amino acid, particularly K or E and the repeating units alternate as to whether 1 is a basic or acidic amino acid. This structure is commonly found in keratin.

The copolymer involving repeating units is a powerful method for varying properties, by appropriate choice of the different units, the number of units in each multimer, the spacing between them, and the number of repeats of the multimer combination assembly. Thus, by varying the number and arrangement of primary monomers, a variety of different physical and chemical properties can be achieved.

Exemplary of the use of the block copolymers are combinations of silk units and elastin units to provide products having properties distinctive from polymers only having the same monomeric unit.

The repetitive proteins can find a variety of uses. The Slp proteins may be used in producing fibers having unique properties, as a substitute for silk, and the like. Collagen proteins can be produced, where the collagen is free of the telopeptide or contains the telopeptide, depending upon its function. Atelopeptidecollagen should have little if any immunogenicity, so as to be a useful structural element for a variety of prosthetic devices or for use as a collagen substitute in other applications. Similarly, other proteins having repetitive sequences, such as keratin, can also be prepared in accordance with the subject invention. Other useful repetitive proteins can be prepared based on sequences of spider silks and other repetitive animal fibers. Artificial peptides useful for immunization could also be prepared based on repeating sequences present in various surface antigens of disease-causing microorganisms, such as parasites, bacteria, and viruses.

The following examples are offered by way of illustration and not with limitation.

EXAMPLE 1

DNA Preparation Methods

1. Preparation of Plasmid DNA from *E. coli*

A. Small scale: Plasmid DNA was prepared from 1.5 ml cultures by either the boiling procedure or the alkaline lysis method (Maniatis et al., Molecular Cloning: A Laboratory Manual. Cold Spring Harbor Laboratory, Cold Spring Harbor. (1982)).

B. Large scale: A plasmid-carrying strain was grown overnight in 1 liter of Luria broth with the appropriate antibiotic. The cells were collected by centrifugation at 10,000 xg for 5 min and resuspended in 10 ml of ice cold TE (10 mM Tris-HCl pH 8, 1 mM EDTA). The cells were centrifuged again, resuspended in 4 ml of TES (TE and 25% w/v sucrose) and homogenized by vortexing. The samples were kept on ice for the following steps. Lysozyme (1 ml of 10 mg/ml) was added to the cell suspension and incubated for 5 min before the addition of 2 ml of 0.5M EDTA pH 8. After 10 min incubation, 50 ml of proteinase K (40 mg/ml) were added followed 10 min later with 15 ml of lysing buffer (0.1% Triton X-100, 1 mM EDTA, 50 mM Tris-HCl pH 8). After 15–20 min, the cell lysate was centrifuged at 35,000 xg for 90–120 min. The supernatant (19.8 ml) was transferred to a plastic tube with 20 g of CsCl and 400 µl of ethidium bromide (10 mg/ml). After dissolution, the mixture was divided into two polyallomer ultracentrifuge tubes, sealed with heat and centrifuged in a Beckman Ti 65 rotor at 60,000 rpm for 24 hr. The lower plasmid DNA band was removed from the tube with a hypodermic needle. The ethidium bromide was extracted three times with an equal volume of NaCl-saturated isopropanol. Two volumes of $H_2O$ were added to the DNA solution, and then the DNA was precipitated with ethanol.

2. Preparation of Double-stranded DNA

A culture of JM103 was grown to an $OD_{600}$ of about 0.2 and then divided into aliquots of 2 ml. Each aliquot was infected with a fresh plaque of M13 and incubated at 37° C. for about 6 hr with vigorous shaking. Then the cells were pelleted and the supernatant was saved for subsequent infections. The double-stranded phage DNA was extracted by the boiling method (Maniatis et al.).

3. Deproteinization

Phenol extraction was performed on a convenient volume of DNA sample, typically between 100 µl to 10 ml. The DNA sample was diluted in 0.01M Tris-HCl pH 7.5, 1 mM EDTA and an equal volume of water-saturated phenol was added. The sample was vortexed briefly and placed on ice for 3 min. After centrifugation for 3 min in a microfuge, the aqueous layer was removed to a new tube and extracted once with an equal volume of chloroform:isoamylalcohol (24:1).

4. Ethanol Precipitation

DNA in an aqueous buffer was concentrated by ethanol precipitation. To the DNA sample was added 1/10 volume of 3M sodium acetate pH 7.5 and 2–3 volumes of cold ethanol. The DNA was precipitated for 30 min at −70° C. or overnight at −20° C. and then pelleted by centrifugation in the microfuge for 15 min at 4° C. The pellet was washed once with 200 µl of cold 80% ethanol and pelleted again for 10 min at 4° C. After air drying or lyophilization, the pellets were resuspended in the appropriate buffer.

5. Phosphatase Treatment of DNA

A. Phosphatase treatment of DNA was performed by adding 1 µl (25 units) of calf intestinal phosphatase (Boehringer Mannheim) directly to the restriction enzyme digestion reaction and continuing the incubation for 30 min at 37° C. The phosphatase was inactivated for 60 min at 65° C. prior to deproteinization by phenol extraction.

B. Phosphatase treatment of DNA was also performed by resuspending ethanol precipitated DNA from the restriction enzyme digest in 20 mM Tris-HCl pH 8.0, 10 mM $MgCl_2$ to a final DNA concentration of 20 µg/ml. Shrimp alkaline phosphatase was added at 2 U/µg of DNA and the mixture was incubated at 37° C. for one hour, heat inactivated for 20 minutes at 65° C. and then passed through a Probind filter (Millipore) by microfuging for 30 seconds at 12,000 RPM. The DNA was then ethanol precipitated and resuspended in suitable buffer.

6. Phosphorylation of DNA

Phosphorylation before annealing was performed by using Polynucleotide Kinase 3'-phosphatase-free (Boehringer Mannheim). The reaction was carried out at 37° C. for 30 minutes in a 50 µl reaction volume containing: 12.5 µg DNA, 5 µl 10× kinase buffer (0.5M Tris pH 7.5, 10 mM Spermidine, 0.1M $MgCl_2$, 150 mM DTT, 1 mM EDTA), and 2 µl Polynucleotide Kinase (10 U/µl). After phosphorylation, salts and glycerol were removed from the DNA strands using a Bio-Spin 6 column (BioRad) equilibrated in TEAB.

7. Fill-in Reaction with DNA Polymerase I

DNA was resuspended in buffer containing 50 mM Tris-HCl pH 7.4, 50 mM KCl, 5 mM $MgCl_2$, and 400 µM each of the four deoxynucleotide triphosphates. Ten units of Klenow DNA polymerase (BRL) were added, and the reaction was allowed to proceed for 15 min at room temperature. The DNA was then phenol extracted and ethanol precipitated.

8. T4 Polynucleotide Kinase Reaction

The reaction (10 µl) contained: T4 polynucleotide kinase (BRL), 150 ng of DNA, 1 µl of 10× kinase buffer (0.7M Tris-HCl pH 7.6, 0.1M $MgCl_2$, 50 mM DTT) and [$^{32}$P]-ATP (200–300 nCi). This was incubated at 37° C. for 30 min and then the DNA was purified using a NACS column (Bethesda Research Labs).

9. Digestion with Restriction Endonucleases

DNA was digested with restriction endonucleases (REN) in 1× "AA" buffer [10× AA buffer is 330 mM Tris-acetate, pH 7.9, 660 mM potassium acetate, 100 mM magnesium acetate, 50 mM dithiothreitol (DTT) and 1 mg/ml bovine serum albumin (nuclease free)]. Whenever possible, the concentration of DNA was kept below 1 μg/25 μl. Incubation was at 37° C. for 1–4 hrs for most restriction endonucleases except for BalI, BanI and NaeI digestions which were incubated overnight.

10. Analytical Agarose Gel Electrophoresis of DNA

To DNA samples for gel analysis we added 0.2 volumes of loading buffer (5× electrophoresis buffer, 0.01% bromphenol blue dye, 50 mM EDTA, and 50% glycerol). Then the samples were loaded into lanes of a horizontal submerged electrophoresis unit containing a 1.0% (w/v) agarose gel. The electrophoresis buffer was either 1×TAC or 1/2× TBE. The 1×TAC is 40 mM Tris-base, 10 mM EDTA, adjusted to pH 7.8 with acetic acid. The 1/2×TBE is 0.045M Tris-base, 0.045M boric acid, 1 mM EDTA, pH 8. The gel was run at 40–50 V for 18 hr, then removed and stained with 0.5 μg/ml ethidium bromide for 30 min. The DNA bands were visualized on a long wavelength UV transilluminator.

11. Preparative Agarose Gel Electrophoresis

The procedures and materials are the same as for the analytical agarose gel electrophoresis. The only difference is the use of low melting point (LMP) agarose, ranging in concentration from 0.5 to 2.5% (w/v) depending on the size of the DNA fragment to be purified. DNA restriction fragments were excised from the LMP agarose gels after visualization with ethidium bromide. For agarose ligation, the buffer used was 1× TAE.

12. NACS Purification

Gel fragments containing DNA were melted at 70° C. for 5 min and diluted approximately 5 fold with TE1(10 mM Tris-HCl pH 7.5, 0.2M NaCl). The gel solution was applied to a NACS column (BRL). The column was washed with 5 ml of the same buffer. The bound DNA was eluted with 300 μl of either TE2 (10 mM Tris-HCl pH 7.5, 1.0M NaCl) for DNA fragments smaller than 1000 bp or TE3 (10 mM Tris-HCl pH 7.5, 2M NaCl) for larger fragments. The eluted DNA was concentrated by ethanol precipitation.

13. DNA Ligation

Reactions for ligating cohesive ends contained: 1 μg DNA, 1×AA buffer (see step 8, above) 1 mM ATP and 20 units of T4 DNA ligase (BRL) in a 20 μl final reaction volume. The ligation was allowed to proceed for 16–18 hr at 15° C. or 1–2 hr at room temperature. For blunt-ended ligations the reactions contained 1 μg DNA, 25 mM Tris-HCl pH 7.5, 5 mM MgCl$_2$, 5 mM DTT, 0.25 mM spermidine, 200 mg BSA, 1 mM hexamine cobalt chloride (HCC), 0.5 mM ATP and 400 units T4 DNA ligase (NEB) in a 20 μl reaction volume. The ligation was allowed to proceed for 30 min to 1 hr at room temperature.

14. Agarose DNA Ligation

The agarose was melted at 65° C., the temperature was then lowered to 37° C. and ligation buffer (5×=100 mM Tris-HCl, pH 7.5, 50 mM MgCl$_2$, 50 mM DTT, 1 mM ATP) was added; the tube was then placed at room temperature and ligase was added (1000 units T4 DNA ligase (NEB)), the reaction volume was usually 50 μl. The reaction was incubated at 15° C. for 16–18 hrs.

15. Agarose DNA Purification using Ultrafree®-MC Filter Unit

This procedure can be used for agarose slices up to 400 μl in size. After agarose gel electrophoresis the DNA is visualized by ethidium bromide staining and the agarose block containing the DNA band of interest is excised. The agarose is then frozen at −20° C. for 1 hour; then quickly thawed at 37° C. for 5 minutes. The agarose is then thoroughly macerated. The pieces are then transferred into the sample cup of the filter unit and spun at 5,000 xg in a standard microfuge. The agarose is then resuspended in 200 μl of Tris-EDTA, or other buffer, and incubated at room temperature to allow for elution of additional DNA from the gel. The mixture is then centrifuged for an additional 20 minutes at 10,000 RPM. The DNA is, at this point, in the filtrate tube separated from the agarose fragments and ready for subsequent DNA manipulations.

Bacterial Transformation Methods

1. Preparation of Transformation-competent E. coli Cells

A culture of 200 ml of sterile L broth was inoculated with a small loopful of E. coli cells. This was incubated with shaking at 37° C. until the OD$_{600}$ was approximately 0.5. The culture was placed on ice for 10 min and centrifuged at 6,000 xg for 10 min. The cell pellet was resuspended in 100 ml of ice-cold 0.1M MgCl$_2$, kept on ice for 30–40 min and centrifuged again. The pellet was resuspended in 2 ml of ice-cold 100 mM CaCl$_2$, transferred to a sterile test tube and incubated on ice for 24 hr. The competent cells were then aliquoted and stored at −70° C.

2. Transformation of E. coli

An aliquot of frozen competent cells were thawed on ice. To 50 μl of cells 0.1 to 1 μg of DNA was added and the mixture was incubated on ice for 30 min. The tube was removed from ice and placed in a 42° C. bath for 2 min. L broth (1 ml) was added and the transformation mix incubated with shaking at the desired temperature (usually 30° C. or 37° C.) for 2 hr. Then one-tenth of the transformation was plated on L broth plates containing the appropriate antibiotic and, when necessary, XGAL and IPTG were added.

3. DNA Transformation of B. subtilis

B. subtilis cells were grown to early stationary phase (change in Klett units of ≦5% in 15 min). Transformation followed established procedures (Anagnostopoulos et al., 1981) (ref. 8). Cells (0.45 ml) were incubated with 1–10 μg of DNA at 37° C. for 80 min with shaking, and then plated on TBAB agar plates with an appropriate antibiotic.

4. Isolation of Plasmid DNA from B. subtilis

Plasmid DNA from B. subtilis was obtained by a method similar to the alkaline-lysis method except that pelleted cells were resuspended in 8 ml of solution 1 (50 mM glucose, 10 mM EDTA, 25 mM Tris-HCl (pH 8.0), 10 mg/ml lysozyme) and incubated at room temperature for 30 min. Then 16 ml of solution 2 (0.2N NaOH, 1% (w/v) SDS) was added and incubated on ice for 10 min. Finally, 12 ml of 3M potassium acetate (pH 4.8) was added and incubated an additional 20 min on ice. The lysed cells were centrifuged 15 min at 15,000 rpm in a Sorval SS-34 rotor. The DNA was precipitated by adding an equal volume of isopropyl alcohol and centrifuged at 7,000 rpm. The pellet was resuspended in 5 ml of 10 mM Tris-HCl (pH 7.5), 1 mM EDTA (TE). The solution was phenol extracted once and chloroform extracted. DNA was precipitated with ethanol and resuspended in 3 ml of TE. The volume was adjusted to 5.2 ml by adding 4.2 g CsCl, 400 μl of ethidium bromide at 10 mg/ml and TE. The solution was transferred to a Beckman quickseal polyallomer centrifuge tube and centrifuged at 45,000 rpm in a Beckman vti65 rotor for 18 hr.

Antibody Production, Protein Chemistry and Electrophoresis of Proteins

1. Preparation of Antibody to Artificially Synthesized Peptides

Synthetic peptide of sequence (GAGAGS)$_8$GAAGY (SEQ ID NO:08) was coupled to BSA using the glutaraldehyde procedure of Kagen and Glick (1979). The degree of coupling was monitored using trace amounts of radioactive iodinated synthetic peptide. Peptide conjugates at a concentration of 1 mg/ml in complete Freund's adjuvant were used to immunize rabbits at day 0. Animals were re-injected with antigen in Freund's incomplete adjuvant at day 30 and titered at day 60. Positive sera was detected using a microtiter RIA using the synthetic peptide as antigen. Kagen and Glick (1979), in Methods of Radioimmunoassay, Jaffe and Berman (eds.), Academic Press, p. 328.

The synthetic peptide of 53 amino acids as described above was prepared on an Applied Biosystems peptide synthesizer. The yield of this material, which has a molecular weight of 3640 was approximately 0.5 grams. The peptide was coupled to bovine serum albumin. The material was sent to Antibodies, Inc. for preparation of antibodies in rabbits. Antisera was obtained that reacted with synthetic peptides of both the SlpI and SlpIII sequences. These antisera have been useful for the detection of fusion peptides containing gly-ala sequences.

Following the procedure described above an antigen was synthesized having the formula (V-P-G-V-G)(SEQ ID NO:09)$_8$, which was coupled to keyhole limpet hemocyanin. Polyclonal antisera was then prepared as described above which bound to the ELP peptide.

Following the same procedure, additional antigens were synthesized having the formula YTITVYAVTGRGD-SPASSKPISINYC (SEQ ID NO:10) of fibronectin (the FCB portion) and the formula (GAPGAPGSQGAPGLQ)$_2$ YMK (SEQ ID NO:11) (a repeat unit of the collagen-like protein (CLP) sequence) which were coupled to keyhole limpet hemocyanin for use as immunogens. Polyclonal antisera were then prepared as described above which bound, respectively, to the FCB peptide, and to the synthetic peptide of the CLP 3.7 sequence.

2. Polyacrylamide Gel Electrophoresis of Proteins

Approximately $10^9$ E. coli cells from growing cultures were pelleted by centrifugation at 10,000 xg for 5 min. The cell pellets were resuspended in 100 to 500 µl of 2× sample buffer (100 mM Tris-HCl pH 6.8, 4% SDS, 10% β-mercaptoethanol, 60% glycerol or sucrose) and sonicated for 30 sec using a Tekmar sonic disruptor. Samples were boiled for approximately 5 min and 20 to 100 µl of the cell lysates were loaded on an SDS-polyacrylamide gel (7.5 to 16% w/v). The gels were prepared following the procedure of Laemmli (Nature, 227:680–685 (1970)). The proteins in the gels were stained with 2% Coomassie brilliant blue in 10% methanol, 7.5% acetic acid for 1 hr and destained in 10% methanol, 7.5% acetic acid overnight.

3. Protein Expression Analysis

An overnight culture which had been grown at 30° C. was used to inoculate 50 ml of LB media contained in a 250 ml flask. Kanamycin was added at a final concentration of 50 µg/ml and the culture was incubated with agitation (200 RPM) at 30° C. When the culture reached an OD$_{600}$ of 0.8, 40 ml were transferred to a new flask prewarmed at 42° C. and incubated at the same temperature for approximately 2 hours. The cultures (30° and 42°) were chilled on ice and OD$_{600}$ was taken. Cells were collected by centrifugation and then divided in 1.0 OD$_{600}$ aliquots and used to perform western analysis using the appropriate antibodies.

4. Immunoblotting of Proteins in Gels

After protein electrophoresis, one of the flanking glass plates was removed from the polyacrylamide gel. The gel surface was wetted with transfer buffer (25 mM Tris-HCl, 192 mM glycine, 20% methanol). A piece of nitrocellulose paper (Sartorius, SM11307) was saturated with transfer buffer and laid on the gel. Air bubbles between the filter and the gel were removed. The gel and nitrocellulose filter were placed in the transfer unit as specified by the manufacturer (BioRad). Transfer was allowed to proceed at 200 mA for 3–4 hr. Then the nitrocellulose filter was removed and stained with Amido-Schwartz for 3 min (0.05% Amido black, 45% deionized H$_2$O, 45% methanol, 10% acetic acid) and destained in H$_2$O. The filter was incubated for at least 10 min at room temperature in "BLOTTO" (5% w/v nonfat dry milk, 50 mM Tris-HCl pH 7.4, 0.9% w/v NaCl, 0.2% w/v sodium azide). The filter was placed in serum appropriately diluted (1:50 to 1:500) in 0.5× BLOTTO (2.5% nonfat dry milk, 50 mM Tris-HCl pH 7.4, 0.9% NaCl, 0.2% sodium azide) and was gently agitated for approximately 16 hr at room temperature. The filter was washed for 1 hr with 5 changes of TSA (50 mM Tris-HCl pH 7.4, 0.9% NaCl, 0.2% sodium azide). The blot was placed in 15 ml of 0.5× BLOTTO solution containing 1×10$^7$ cpm of the $^{125}$I-protein A and gently agitated for 2 hr at room temperature. The filter was washed for 2 hr with a minimum of 7 changes of TSA, rinsed once with deionized H$^2$O and air dried. The blot was covered with Saran wrap and autoradiographed.

5. Amino Acid Analysis

Amino acid compositions are determined by the PTC derivatization procedure of Henrickson and Meredith (1984). Protein samples were hydrolysed with 5.7N constant boiling HCl at 108° C. for 24 hours in vacuo. After reaction with PITC, amino acid derivatives were detected at 254 nm by HPLC reverse phase chromatography using a Hewlett Packard 1090 or Waters 600E system and a Supelco C18 column (4.6 mm×25 cm) with a linear gradient of 0–50% acetonitrile in 0.1M NH$_4$OAc pH 6.78 as a mobile base. Henrickson, R. L. and Meredith, S. C. (1984) Amino Analysis by Reverse Phase High Performance Liquid Chromatography, Anal. Biochem. 137:65–74.

6. Amino Acid Sequence Analysis

The N-terminal amino acid sequence was determined by automated Edman degradation using an Applied Biosystems Model 470A gas phase protein sequenator. The PTH amino acid derivatives were analyzed by reverse phase HPLC using a Hewlett Packard 1090 system and an Altex C18 column (2 mm×25 cm) with a complex gradient buffer system.

7. Peptide Synthesis

Synthetic peptides were prepared by solid phase synthesis on an Applied Biosystems Model 430A Peptide Synthesizer using the standard symmetric anhydride chemistry as provided by the manufacturer. The coupling yield at each step was determined by the quantitative ninhydrin procedure of Sarin et al., (1981). The synthetic peptide was cleaved from the solid support and amino acid blocking groups were removed using anhydrous HF (Stewart and Young, 1984). Crude peptides were desalted by chromatography over Sephadex G-50. Sarin, V. K., Kent, S. B. H., Tam, J. P. and Merrifield, R. B. (1981), Anal. Biochem., 237:927–936. Stewart, J. M. and Young, J. D. (1984). Solid Phase Peptide Synthesis, Pierce Chemical Company, Rockford, Ill., pp. 85–89.

Synthetic DNA Methods

1. In vitro DNA Synthesis

The N,N-diisopropylphosphoramidites, controlled-pore glass columns and all synthesis reagents were obtained from Applied Biosystems, Foster City, Calif.

Synthetic oligonucleotides were prepared by the phosphite triester method with an Applied Biosystems Model 380A or 381A DNA synthesizer using a 10-fold excess of protected phosphoramidites and 1 µmole of nucleotide bound to the synthesis support column. The chemistries used for synthesis are the standard protocols recommended for use with the synthesizer and have been described (Matteucci et al., *Journal Amer. Chem. Soc.*, 103:3185–3319 (1981)). Deprotection and cleavage of the oligomers from the solid support were performed according to standard procedures as described by McBride et al., *Tetrahedron Letters*, 24:245–248 (1983). The repetitive yield of the synthesis as measured by the optical density of the removed protecting group as recommended by Applied Biosystems (1984) was greater than 97.5%.

The crude oligonucleotide mixture was purified by preparative gel electrophoresis as described by the Applied Biosystems protocols of Nov. 9, 1984 (User Bulletin No. 13). The acrylamide gel concentration varied from 10 to 20% depending upon the length of the oligomer. The purified oligomer was identified by UV shadowing, excised from the gel and extracted by the crush and soak procedure (Smith, *Methods in Enzymology*, 65:371–379 (1980)).

2. Sequencing of DNA

DNA sequences were determined by the following methods. Fragments containing the region of interest were cloned into the multiple cloning site of M13mp18 or M13mp19 (Maniatis et al., 1982, and Norrander et al., 1983). Single-stranded DNA was prepared and sequenced by the primer extension method (Sanger et al., 1977, and Biggin et al., 1983) using 35S-deoxyadenosine 5'-(alpha-thio)-triphosphate (New England Nuclear) as label. In some cases, reverse transcriptase (Molecular Genetics) was used to extend the primer, using the dideoxy:deoxynucleosidetriphosphate ratios utilized by Zagursky et al., *Gene Anal. Techn.* (1985) 2:89–94). Deoxyadenosine triphosphate labeled with either $^{32}P$ or $^{35}S$ was used in these reactions. Compression artifacts which appeared in some G-C rich sequences were overcome by eliminating deoxguanosine triphosphate from the G reaction, and using deoxyinosine triphosphate (P-L Biochemicals) at a final concentration of 37.5 µM instead. In the other mixes, the concentration of dideoxyGTP in the G reaction was 0.5 mM. All sequences were run on 6 or 8% polyacrylamide gels containing 8M urea (Sanger et al. 1978). Primers used for sequencing were purchased from P-L Biochemicals. Storage and analysis of data utilized software from both DNAstar and International Biotechnologies, Inc. for IBM personal computer and DNA Strider, DNA Inspection IIe or DNAid for Apple Macintosh personal computer.

3. In vitro Mutagenesis of Cloned DNA

Plasmid DNA (1 µg) containing the sequence to be mutated was digested in two separate reactions. One reaction contained either one or two restriction endonucleases which cleave at sites immediately flanking the region of interest. In the second reaction, the DNA was digested with a restriction endonuclease which cleaves only once at a site distant from the sequence to be mutated. The DNA fragments generated in the first reaction were separated by agarose gel electrophoresis and the large fragment which lacks the sequence to be mutated was excised and purified. DNA from the second reaction, the large fragment of DNA from the first reaction, and a synthetic oligodeoxynucleotide of 20–30 bases in length containing the mutant sequence were mixed in a molar ratio of 1:1:250. The mixture was denatured by heating at 100° C. for 3 min in 25 to 100 µl of 100 mM NaCl, 6.5 mM Tris-HCl pH 7.5, 8 mM $MgCl_2$, and 1 mM β-mercaptoethanol. The denatured mixture was reannealed by gradually lowering the temperature as follows: 37° C. for 30 min, 4° C. for 30 min, and 0° C. for 10 min. The reaction was supplemented with 0.5 mM deoxyribonucleotide triphosphates, 1 mM ATP, 400 units of T4 DNA ligase and 5 units of *E. coli* DNA polymerase large fragment and incubated at 15° C. for 12–16 hr. The reaction mixture was then transformed into *E. coli* and antibiotic-resistant colonies were selected.

4. Dideoxy DNA Sequencing of Double Stranded Plasmid DNA

Plamsid DNA was prepared as described previously (Preparation of plasmid DNA from *E. coli*, Small scale, Maniatis et al.). Primers were synthesized using a DNA synthesizer as described previously, and were annealed to the plasmid DNA following the procedure described above for M13 sequencing. The sequencing reactions were done using Sequenase (United States Biochemicals) and the conditions were as recommended by the supplier. All sequences were run on polyacrylamide gels as described above.

5. PCR Amplification

The PCR reaction was performed in a 100 µl volume in a Perkin Elmer thin-walled Gene Amp™ reaction tube. Approximately 1 µM of each primer DNA was added to 1× PCR buffer (supplied by Perkin Elmer as 10× solution), 200 µM of each dNT, 5 U AmpliTaq, and several concentrations of the target DNA. Amplification was performed in a Perkin Elmer DNA Thermal cycler model 480 for 30 cycles with the following step cycles of 12 min each: 95° C., 62° C., and 72° C. Aliquots from the different reactions were analyzed by Agarose Gel Electrophoresis using 1.5% Low Melting Point agarose in 0.5× TA buffer. The reaction mixtures that gave the desired band were pooled and spun through an Ultrafree-Probind filter unit (Millipore) at 12,000 RPM for 30 seconds in a Sorvall Microspin 24S to remove the AmpliTaq enzyme. The buffer was then exchanged with $H_2O$ two times, using a Microcon-30 filter (Amicon) by spinning at 12,000 RPM for 6 min in a microfuge. Salts and glycerol were removed from the amplified dsDNA using a Bio-Spin 6 column (from BioRad) equilibrated in TEAB, in a Sorvall RC5B centrifuge using an HB4 rotor at 2,500 RPM for 4 min. The DNA was then concentrated in vacuo.

Fermentation Conditions

The fermentor is a 15 L Chemap, 10 L working volume. The culture conditions are: temperature=30° C., pH 6.8; NaOH 2.5M is used for pH regulation. The headspace pressure is below 0.1 bar. The dissolved oxygen is regulated at 50%. The air flow varies from 0.5 L/min to 20L/min. The agitation rate varies between 200 to 1500 rpm. The fermentor is inoculated with a 10% (v/v) inoculum grown in medium A for 15 hours at 30° C. under agitation.

Medium B, C or D was the fermentor medium. The starting volume in the case of a 10 liter fermentation, is no less than 3 liters, and in the case of a 1 liter fermentation, is no less than 0.5 liter.

If the fermentor starting volume is less than the final volume desired, then when the carbon source concentration reaches 1%, a concentrated solution (5×) of medium B, C or D, respectively, is added to the fermentor in order to keep the carbon source concentration approximately 1%.

When the culture reached an $OD_{600}$ of 60.0, the temperature was increased to 42° C. for 10 min, then lowered to 39° C. for 2.5 hours. The cells were then harvested by centrifugation and frozen at −70° C. until processed.

TABLE 1

Medium Table

| Constituent | g/L |
|---|---|
| Medium A: LB Medium | |
| NaCl | 10 |
| tryptone | 10 |
| yeast extract | 5 |
| kanamycin | $5 \times 10^{-3}$ |
| Medium B | |
| $NH_3Cl$ | 4.5 |
| $KH_2PO_4$ | 0.76 |
| $MgSO_4 \cdot 7H_2O$ | 0.18 |
| $K_2SO_4$ | 0.09 |
| $CaCl_2$ | $24 \times 10^{-3}$ |
| $FeSO_4 \cdot 7H_2O$ | $7.6 \times 10^{-3}$ |
| TE | 0.5 ml |
| casamino acids | 25 |
| yeast extract | 5 |
| glucose | 20 |
| kanamycin | $5 \times 10^{-3}$ |
| Medium D | |
| $(NH_4)SO_4$ | 5.6 |
| $K_2HPO_4$ | 6.7 |
| $MgSO_4 \cdot 7H_2O$ | 7.8 |
| $NaH_2PO_4 \cdot H_2O$ | 3.8 |
| EDTA | 0.98 |
| Trace Elements | 1 ml |
| yeast extract or NZ Amine | 50 |
| glucose or glycerol | 20 |
| kanamycin or ampicillin | $5 \times 10^{-3}$ |

EXAMPLE 2

Assembly and Expression of the SlpI Gene

1. Summary of the Scheme for Assembling the SlpI Gene

An 18 bp DNA sequence that codes for the most frequent repeating oligopeptide in the silk fibroin protein made by *Bombyx mori* [Lucas, F. and K. M. Rudall (1986) Extracellular Fibrous Proteins: The Silks. p. 475–558, in Comprehensive Biochemistry, vol. 26, part B., M. Florkin and F. H. Stotz (eds.) Elsevier, Amsterdam] was synthesized in vitro. Two single-strands were synthesized, annealed together and then the resulting double-stranded segments were multimerized head-to-tail to generate concatamers of up to and exceeding 13 repeats. The structural gene for silk I that we proceeded to work with had 13 repeats that coded for the oligopeptide gagags, where g=glycine, a=alanine and s=serine. We refer to this structural gene as the "monomer". We constructed "dimeric, trimeric, tetrameric, pentameric and hexameric" SlpI genes containing 26 (SlpI-2), 39 (SlpI-3), 52 (SlpI-4), 65 (SlpI-5) and 78 (SlpI-6) repeats. There is a short intervening sequence between each monomer unit. The assembly is pictured as follows:

2. Assembly of the "Monomeric" SlpI Structural Gene

The two single-strands shown above were synthesized as previously described. The strands were separately purified by gel electrophoresis, phosphorylated using T4 polynucleotide kinase and then mixed together and allowed to anneal. This resulted in the double-stranded segments aligning spontaneously head-to-tail in long concatamers. The phosphodiester bonds between segments were formed with T4 DNA ligase. The reaction was stopped by filling in the terminal cohesive ends using the Klenow fragment of DNA polymerase I. The blunt-ended repeating DNA was then ligated to the HincII REN site in plasmid vector pUC12 (Veira et al., *Gene* 19:259–268 (1982)). The ligated DNA was transformed into *E. coli* HB101 and transformants were selected for their ability to grow in the presence of ampicillin. The DNA of potential clones was analyzed; for size and orientation by REN digestion and gel electrophoresis. DNA sequences were determined for isolates with large inserts that were oriented properly. The "monomer" clone selected for subsequent multimerization had 13 repeats coding for the oligopeptide agagsg, and was named pSY708. The DNA sequence, deduced amino acid sequence and REN sites of the SlpI insert and flanking regions of pSY708 are shown in Table 2.

Repeating DNA sequence  5'- G G T G C G G G C G C A G G A A G T (SEQ ID NO:12)
                           C G C C C G C G T C C T T C A C C A-5' (SEQ ID NO:13)

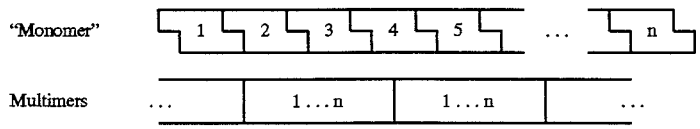

TABLE 2

```
H        P       A S
I        S       V M
N        T       A A
3        1       1 1
:        :       : :
AAGCTTGGGCTGCAGGTCACCCGGGCGGGCGCAGGAAGTGGTGCGGGCGCAGGAAGTGGT
----.----+----.----+----.----+----.----+----.----+----.----  60
TTCGAACCCGACGTCCAGTGGGCCCGCCCGCGTCCTTCACCACGCCCGCGTCCTTCACCA k  l  g  l  q  v  t  r  a  g  a  g  s  g  a  g  a  g  s  g
----.----+----.----+----.----+----.----+----.----+----.----+

GCGGGCGCAGGAAGTGGTGCGGGCGCAGGAAGTGGTGCGGGCGCAGGAAGTGGTGCGGGC
----.----+----.----+----.----+----.----+----.----+----.----+ 120
CGCCCGCGTCCTTCACCACGCCCGCGTCCTTCACCACGCCCGCGTCCTTCACCACGCCCG a  g  a  g  s  g  a  g  a  g  s  g  a  g  a  g  s  g  a  g
----.----+----.----+----.----+----.----+----.----+----.----+

GCAGGAAGTGGTGCGGGCGCAGGAAGTGGTGCGGGCGCAGGAAGTGGTGCGGGCGCAGGA
----.----+----.----+----.----+----.----+----.----+----.----+ 180
CGTCCTTCACCACGCCCGCGTCCTTCACCACGCCCGCGTCCTTCACCACGCCCGCGTCCT a  g  s  g  a  g  a  g  s  g  a  g  a  g  s  g  a  g  a  g
----.----+----.----+----.----+----.----+----.----+----.----+

AGTGGTGCGGGCGCAGGAAGTGGTGCGGGCGCAGGAAGTGGTGCGGGCGCAGGAAGTGGT
----.----+----.----+----.----+----.----+----.----+----.----+ 240
TCACCACGCCCGCGTCCTTCACCACGCCCGCGTCCTTCACCACGCCCGCGTCCTTCACCA s  g  a  g  a  g  s  g  a  g  a  g  s  g  a  g  a  g  s  g
----.----+----.----+----.----+----.----+----.----+----.----+

X       B       A S         E
              B       A       V M         C
              A       M       A A         R
              1       1       1 1         1
              :       :       : :         :
GCGGGCGCAGGAAGTGGGACTCTAGAGGATCCCCGGGCGAGCTCGAATTC
----.----+----.----+----.----+----.----+----.----+ 290 (SEQ ID NO:14)
CGCCCGCGTCCTTCACCCTGAGATCTCCTAGGGGCCCGCTCGAGCTTAAG a  g  a  g  s  g  t  l  e  d  p  r  a  s  s  n  s (SEQ ID NO:15)
----.----+----.----+----.----+----.----+----.----+
```

3. Construction of the Expression Vector, pSY701

Plasmid pSP65 (10 μg, Boehringer Mannheim) was digested with AatII REN, phenol extracted and ethanol precipitated. The DNA was resuspended in 10 μl of H$_2$O. One-half of this DNA was digested with exonuclease III in the following mix: 5 μg DNA, 10 μl 10× exonuclease III buffer (600 mM Tris-HCl pH 8.0, 6.6 mM MgCl$_2$, 10 mM β-mercaptoethanol) and 9 units of exonuclease III in a total volume of 200 μl. Samples of 20 μl were taken at 0, 1, 2.5, 5 and 7.5 min and diluted immediately in 100 μl of the following buffer (30 mM sodium acetate, pH 4.5, 0.25M NaCl, 1 mM ZnSO$_4$) containing 5 μg tRNA and 36 units of S1 nuclease. Incubation was at 30° C. for 45 min and then the reaction was terminated by the addition of 15 μl of stop buffer (0.5M Tris pH 9.0, 125 mM EDTA, 1% w/v SDS, 200 μg/ml tRNA). The samples were phenol extracted and ethanol precipitated. The resuspended DNA was digested with SmaI REN and electrophoresed through a 1% gel of low melting point agarose. The gel band corresponding to the DNA fragment carrying the β-lactamase gene, the plasmid origin and the β-galactosidase promoter was excised from the gel and melted at 65° C. One volume of H$_2$O was added. The DNA in each sample (timepoint) was recircularized by ligation in the presence of agarose. The reaction included 8 μl melted gel, 2 μl of ligation buffer (100 mM Tris-HCl pH 7.5, 50 mM MgCl$_2$, 50 mM DTT, 1 mM ATP), 10 units T4 DNA ligase and was incubated at 15° C. for 3 hr. Competent cells of JM101 were transformed with the ligated DNA and transformants were selected by growth on L broth plates containing ampicillin (40 μg/ml). Plasmid DNA was prepared from four transformants. The DNA was digested with BamHI REN, labeled with $^{32}$P-dGTP using the Klenow fragment of DNA Polymerase I, digested with PvuI and then the smallest fragment was gel purified. The fragment from one transformant was sequenced using the Maxam and Gilbert technique. The fragments of the other three plasmids were further digested with TaqI and electrophoresed on the same gel. The sequenced plasmid had a fusion between the multiple cloning site and a position upstream from the N-terminal ATG of β-lactamase. The size of the BamHI-TaqI fragment of two of the other plasmids indicated a fusion between the multiple cloning site and the 4th amino acid of the β-lactamase gene. The DNA and corresponding amino acid sequences of the N-terminal region of the altered β-lactamase, along with a circular map of REN sites for pSY701, are shown in FIG. 1. The amino acid sequence of FIG. 1 is met-thr-met-ile-thr-pro-ser-leu-gly-cys-arg-ser-thr-leu-glu-asp-pro-his-phe-arg-val-ala-leu-ile-pro-phe-phe-ala-ala-phe-cys-leu-pro-val-phe-ala-his (SEQ ID NO:16).

4. Insertion of "Monomer" SlpI from pSY708 into pSY701

Plasmid pSY708 was digested with HindIII, the cohesive ends were filled in using the Klenow fragment of DNA polymerase I and then digested with BamHI. Plasmid pSY701 was digested with XbaI, filled in as above and then digested with BamHI. The DNA fragment from pSY708 and the backbone of pSY701 were then purified by electrophoresis through a low melting temperature agarose gel and purified with NACS (BRL) columns. The appropriate fragments were mixed, ligated, and then transformed into E. coli JM109. Transformed cells were selected by growth on L plates containing ampicillin (40 mg/ml), IPTG ($5\times10^{-4}$M) and XGAL (20 mg/ml). Transformants were analyzed for plasmid contents and one (pSY756) was selected for further study since it carried the insert of the monomer SlpI-1 sequences in the proper orientation, as determined by mapping of REN sites. Although the entire DNA sequence was not determined for pSY756, the junctions between the insert and vector were verified as correct restriction sequences for XbaI, upstream and BamHI, downstream.

5. Multimerization of the SlpI Gene of pSY756

Plasmid pSY708 was digested with the REN SmaI and the DNA fragment carrying the coding sequence for the polypeptide arg(ala-gly-ala-gly-ser-gly)$_{13}$thr-leu-glu-asp-pro (R(AGAGSG)$_{13}$TLEDP) (SEQ ID NO:17) was purified as in 4 above. Plasmid pSY756 was digested with SmaI, deproteinized and then ligated with the purified DNA fragment from pSY708. Transformants of E. coli JM109 were selected on medium containing ampicillin. Clones were found to contain 2 units (dimer pSY882), 3 units (trimer pSY883), and 4 units (tetramer pSY915) of the original monomer sequence of the pSY708 clone. Similarly, pentamers and hexamers have also been constructed. All of these plasmids are genetically stable and produce the gly-ala peptide as a fusion with β-lactamase.

6. Expression of the SlpI Gene Fusion to the β-Lactamase Protein

Synthesis in E. coli cells of the SlpI peptide as a fusion protein with β-lactamase was detected by immunoblotting (Western) analysis. Anti-"Slp" antibodies were raised against a synthetic silk peptide. Fusions between β-lactamase and SlpI were also detected with antibodies raised against the E. coli β-lactamase. As shown in FIG. 2, this antibody reacts with dimers and trimers of SlpI fused to the E. coli β-lactamase. The SlpI insert precedes the fifth amino acid of the signal sequence for this enzyme. The β-lactamase antibody (FIG. 2A) detects both the unprocessed fusion proteins as well as the processed mature enzyme which appears as the major antigenic band in this figure, at about the 28 kDal position. The mobilities of all Slp-containing polypeptides are anomalously slow and the proteins are not as large as they appear on the gels.

The anti-Slp antibody also is useful in detecting these fusion products. Lanes 2–5 of FIG. 2B represent 4 separate clones that contain dimer fusions of SlpI with β-lactamase, while lanes 6 and 7 are from two clones containing trimer fusions. As can be seen the antigenicity of the trimer is considerably greater than for the dimer. It is known from prior experiments that fusion proteins containing only a monomer of SlpI are not detected at all with this anti-Slp antibody. The increased antigenicity of the trimer peptide allows it to be detected as a processed fusion with the β-lactamase signal peptide. The processed form is seen at about the 33 kDal position in lanes 6 and 7 of FIG. 2B. The appearance of normally processed β-lactamase mature enzyme (detected with β-lactamase antibody) as well as a peptide corresponding to the fusion between the SlpI-3 trimer and the signal peptide of β-lactamase (detected with gly-ala antibody) suggests that despite the insertion of SlpI sequences within the signal sequence, normal proteolytic processing of the enzyme occurs in E. coli.

7.a. Expression of the SlpI Gene by Fusion to T7 Genes

The SlpI sequence has also been expressed as a fusion protein with both the gene 9 and gene 10 proteins from bacteriophage T7 in E. coli. The construction is diagrammed in FIG. 3. Plasmid pSY915 (containing the SlpI-4 tetramer) was digested to completion with REN SalI and partially with BamHI. The DNA fragment containing the SlpI-4 tetramer was purified and then cloned in plasmid pSY114 (pG2 of Promega Biotech) which had been digested with RENs SalI and BamHI. From this intermediate plasmid, the tetramer insert of SlpI was removed with the RENs AccI and EcoRI. This fragment was then cloned in pSY633 (pBR322 containing the complete T7 gene 9 sequence; pAR441 of Studier et al., (1986)) which was digested with EcoRI and AsuII. In the resulting plasmid the SlpI tetramer is fused to the gene 9 translational reading frame near the C-terminus of gene 9. This plasmid was then used to transform E. coli strain 0–48 (strain HMS174 (λDE3) of Studier et al., 1986) which contains the T7 RNA polymerase gene inserted into the chromosome under transcriptional control of the IPTG-inducible β-galactosidase promoter. In this configuration, expression of the SlpI-4 sequence is dependent upon production of the T7 RNA polymerase which itself is controlled by the IPTG inducible β-galactosidase promoter. As shown in FIG. 4B and 4C, when these cells are induced with IPTG a protein product of the gene 9/SlpI-4 fusion gene is synthesized and is detected with antibody to the synthetic Slp peptide. The fusion product migrates in the gel as if it was 82 kDal in size. The size expected is only 65 kdal. The anomalous mobility is characteristic of the unusual amino acid composition (rich in glycine and alanine) and is seen for all Slp-containing products.

In like manner, plasmid pSY638 (pAR2113 of Studier) containing the promoter region and the first 13 amino acids of the T7 gene 10 protein, was digested with REN BamHI, filled in with the Klenow fragment of DNA polymerase and then digested with REN EcoRI. Into this linearized plasmid was cloned the AsuII-EcoRI fragment of pSY633, containing the SlpI-4 tetramer. This ligation creates an in-frame fusion of the silk tetramer following the thirteenth amino acid of T7 gene 10. The latter fusion product may be used for spinning without further processing since the N-terminal 13 amino acids are only a small part of the large SlpI protein. Although the fusion product is about 30 kDal in size, it has an anomalous mobility and migrates as if it was larger, 50 kDal. This is shown in FIG. 4A.

The plasmids pG9/SlpI-4 and pG10/SlpI-4 were further improved by inserting a kanamycin-resistance gene in the β-lactamase gene in the orientation opposite to the T7 expression system. Thus, any low level expression from the T7 system does not lead to elevated β-lactamase activity. Such activity eliminated the ampicillin in the medium that was added to select for maintenance of the plasmid. When the ampicillin was depleted the plasmids were lost from the culture. The kanamycin-resistance gene circumvents this problem and represents a significant improvement in the T7 expression system, especially for large scale cultures. The kanamycin-resistance gene (originally from Tn903) was isolated from a plasmid pUC4K (Veira, J. and Messing, J., (1982) Gene, 19:259–268) as a HincII fragment. The plasmid containing pG10/SlpI-4 and the kanamycin-resistance gene was designated pSY997.

7.b. Fermentation and Purification of SlpI-4

E. coli strain 0–48 carrying pSY997 was grown at 37° C., using a Chemap or a Braun fermentor, in 10 L of LB to an OD (Klett units) of 300 ($3\times10^9$ cells/ml). The T7 system was then induced with the addition of 3.5 mM IPTG. After 150 min the cells were concentrated 10× using a Millipore filter unit (Pellicon cassette system, 100,000 molecular weight cut off filter). The cell suspension was then frozen at −70° C. until processing.

The cell suspension was melted in a water bath at 42° C. and lysed in a french press, and the lysate was spun at 125,000 xg for 1 hour at 25° C. The cleared supernatant was treated with DNAase (250 μm/ml) for 15 min at room temperature, then filtered through a 0.45 μm sterile filter. The filtrate volume was measured and incubated in ice with slow stirring. Then 231 mg of ammonium sulphate were added for each ml of filtrate over a period of 45 min. One ml of NaOH for each 10 g of ammonium sulphate was added to neutralize the pH.

After 2 hours of continuous stirring the mixture was spun at 9,000 xg for 10 min. The pellet was resuspended in 1/10 of the original filtrate volume using distilled water. The centrifugation and resuspension was repeated three times. The pellet was resuspended in 1/10 of the original filtrate volume in distilled water. Samples were analyzed for protein concentration, amino acid composition and protein sequence by standard methods. This is one of several methods for obtaining the product. This method resulted in an SlpI-4 product that was greater than 90% pure. The amino acid composition was almost entirely gly, ala and ser, as expected, and the N-terminal amino acid sequence is that of the gene 10 leader.

8. Controlled Expression of the T7 RNA Polymerase Gene in Bacillus subtilis

The coding sequence of the T7 RNA polymerase gene (T7 gene 1, T7 nucleotides 3128 to 5845) from plasmid pSY558 (pAR1151 of Studier et al., 1986) was modified by in vitro mutagenesis of cloned DNA. We inserted the recognition sequence for the restriction endonuclease NdeI at position 3171. Using an oligodeoxynucleotide which was synthesized as previously described, the T7 gene 1 sequence was changed from its natural sequence, TAAATG (SEQ ID NO:18), to the modified sequence, CATATG (SEQ ID NO:19).

Similarly, the upstream regulatory sequence of the *Bacillus subtilis* gene spoVG, obtained from plasmid pCB1291 (Rosenblum et al., *J. Bacteriology*, 148:341–351 (1981)), was modified by in vitro mutagenesis at position 85 (Johnson et al., *Nature*, 302:800–804 (1983)) such that it also includes an NdeI cleavage site. The upstream regulatory sequences of the spoVG gene were then ligated with the coding sequence of the T7 RNA polymerase gene via these novel NdeI cleavage sites. After transformation of *E. coli* HB101, the plasmid contents of individual ampicillin-resistant isolates were checked by restriction mapping. The correct construction was named pSY649.

Plasmid DNA containing the spoVG:T7 RNA polymerase fusion gene (pSY649) was further modified to include a chloramphenicol-resistance gene that functions in *B. subtilis*. First the NdeI to SalI fragment of about 1200 base pairs from plasmid pGR71-P43 (Goldfarb et al., *Nature*, 293:309–311 (1981)) was isolated. This fragment carries the P43 promoter of *B. subtilis* and an adjacent chloramphenicol acetyltransferase gene from Tn9. After filling in all the cohesive ends using the Klenow DNA polymerase reaction, this fragment was inserted into the XbaI site within the multiple-cloning site of pUC13 (Veira et al., *Gene*, 19:259–268 (1982)). Ampicillin and chloramphenicol-resistant transformants were selected for further use. The correct plasmid construction was named pSY630. The SmaI to HincII endonuclease cleavage fragment from plasmid pSY630 containing the chloramphenicol acetyltransferase gene fused to the P43 promoter sequence was gel purified and blunt-end ligated to the PvuI site of plasmid pSY649 that had been treated first with T4 DNA polymerase. The resulting plasmid, pSY856, was then transformed into *B. subtilis* I168. Because plasmid pSY856 is unable to replicate autonomously in *B. subtilis*, stable transformants resistant to chloramphenicol must result from the integration of the plasmid into the *B. subtilis* chromosome (Ferrari et al., *J. Bacteriology*, 154:1513–1515 (1983)). The integration event, facilitated by homologous recombination, most likely occurred at either the spoVG or the P43 loci of the bacterial chromosome (pSY856 contains DNA sequences homologous to the *B. subtilis* chromosome at only these two sites). The resulting strain, "BIPol," was grown both in the presence and absence of chloramphenicol in order to determine the stability of the selectable marker. Expression of the T7 polymerase was obtained and this has no apparent effect on the growth or viability of this strain.

9.a. Expression of a Plasmid-borne Target Gene (Kanamycin-resistance) in *B. subtilis* Strain BIPol The *Staphylococcus aureus* plasmid pUB110 (Lacey et al., *J. Med. Microbiology*, 7:285–297, 1974) which contains the gene coding for resistance to the antibiotic kanamycin was used to test the expression of the growth-regulated spoVG:T7 RNA polymerase gene of strain BIPol. An EcoRI-BamHI fragment of phage T7 DNA (positions 21,402 to 22,858 containing the T7 gene 9 promoter sequence was purified from plasmid pAR441 (Studier et al., 1986). This DNA fragment was ligated into pUB110 between the EcoRI and BamHI restriction endonuclease sites. The resulting plasmid, pSY952, contains the T7-specific promoter in the same orientation as the kanamycin-resistance gene. Plasmid pSY952 was transformed into *B. subtilis* I168 and BIPol and these strains were analyzed for the level of expression of the polypeptide encoded by the plasmid derived kanamycin-resistance gene. Approximately $10^9$ cells from growing cultures of I168, I168 containing pUB110, I168 containing pSY952, BIPol, BIPol containing pUB110, and BIPol containing pSY952 were obtained at several times during the growth and sporulation cycle. The proteins in these cell samples were processed and analyzed by polyacrylamide gel electrophoresis.

Because the rate of transcription from the spoVG promoter increases as a function of cell density and reaches a maximum during early sporulation, an accelerated accumulation of the target protein is expected in the BIPol strain containing pSY952 during growth as the culture enters sporulation. The results showed that a protein of molecular weight 34 kDal increases in abundance as the culture approaches and enters stationary phase. The size of the protein is in agreement with the predicted size of the kanamycin-resistance gene product (Sadaie et al., *J. Bacteriology*, 141:1178–1182 (1980)) encoded in pSY952. This protein is not present in BIPol or I168 containing pSY952 which lacks the spoVG-regulated T7 RNA polymerase gene or in BIPol containing pUB110 which lacks the T7 promoter sequence. The maximum accumulated level of target protein after 24 hours of growth in BIPol containing pSY952 was 20% of the total cellular protein as determined by densitometry.

9.b. Expression of SlpI-4 in *B. subtilis:*

Plasmid pG10/SlpI was digested with EcoRI REN. After filling in the cohesive ends using the Klenow DNA polymerase reaction, the DNA was digested with BglII REN. Plasmid pSY662 was digested with SmaI and BamHI RENs. The two plasmids were then purified by electrophoresis through a low melting temperature agarose gel and purified with NACS (BRL) columns. The DNA fragment of pG10/SlpI was ligated to the backbone of pSY662 and transformed into *E. coli* containing ampicillin (40 μg/ml). Transformants were analyzed for plasmid contents and one (pSY662/G10/SlpI-4) was selected for further study.

Competent cells of *B. subtilis* BIPol were transformed with pSY662/G10/SlpI-4 and incubated at 37° C. with shaking for 90 min. The transformation mixture was then diluted 1:100 in fresh LB containing 10 µg/ml of tetracycline and incubated at 37° C. with shaking. Samples were taken and equal numbers of cells were lysed and loaded on gels for separation by SDS-PAGE. Immunoblot analysis was performed using anti-Slp antibodies to detect the synthesis of the gene 10/SlpI-4 fusion protein.

The expression of the SlpI-4 polypeptide in *B. subtilis* was detected by its seroreactivity with anti-Slp antibody, after transfer of the cellular proteins from the polyacrylamide gel to a nitrocellulose filter. We verified that the seroreactive protein was the product of the SlpI-4 gene by exhaustively treating the cellular proteins with CNBr. This should cleave after methionine residues, but since SlpI-4 lacks methionine it will remain intact. The CNBr treatment eliminated greater than 98% of the proteins stainable with Coomassie blue dye. And as expected for a protein lacking methionine, SlpI-4 remained intact and still reacted with anti-Slp serum.

EXAMPLE 3

Assembly and Expression of the SlpIII Gene

1. Summary of the Scheme for Assembling the SlpIII Gene

The synthetic SlpIII gene codes for a protein similar to the SlpI gene and to the crystalline region of the silk fibroin protein made by the silkworm, *Bombyx mori*. SlpIII more closely resembles the silk fibroin molecule because it includes the amino acid tyrosine at regular intervals (about 50 residues), whereas multimers of SlpI do not. The SlpIII gene was assembled from smaller parts. First, three double stranded sections of DNA of about 60 bp in length were chemically synthesized. Each section was cloned by insertion into bacteriophage M13 and the DNA sequence was verified. These sections were then removed from the vector and linked together in a specific order. This linkage of about 180 bp is named the SlpIII "monomer." "Monomers" were then linked in a specific order to yield dimers, trimers, tetramers, etc., of SlpIII. The multimers were then cloned either directly into plasmid expression vectors to detect the SlpIII protein or initially into an adapter plasmid. Insertion of the SlpIII DNA into the adapter allows for further gene manipulation and is further described later.

2. Synthesis of Double Stranded DNA Sections

The assembly scheme is pictured as follows:

The DNA and corresponding amino acid sequences of the three sections of the SlpIII gene are shown in Table 3.

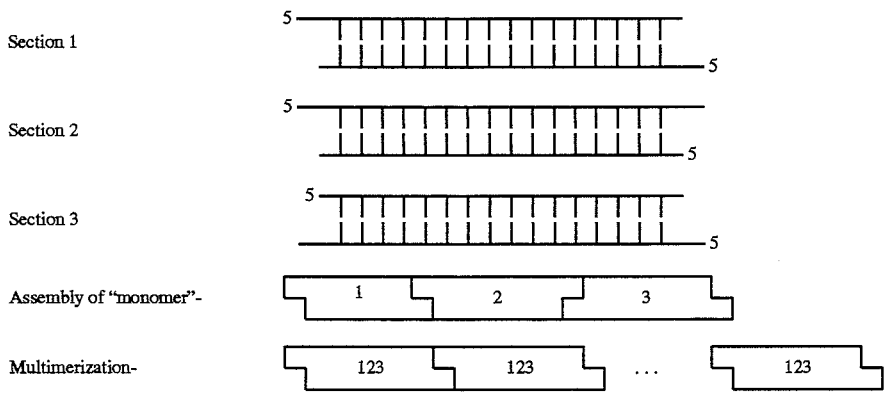

TABLE 3

```
     BanXI
     |
GGT GCC GGC AGC GGT GCA GGA GCC GGT TCT GGA GCT GGC GCG GCT GGC GCG GCA G           61bs (SEQ ID NO:20)
CCA CGG CCG TCG CCA CGT CCT CGG CCA AGA CCT CGA CCG CGC CCG CGT CCT AG              65bs (SEQ ID NO:21)
 G   A   G   S   G   A   G   S   G   A   G   S   G   A   G   S  (SEQ ID NO:22)

BaHI
     |
GA TCC GGC GCT GGT TCT GGC GCA GGG GCA GGC TCT GGC GCA GGA GCG GGG TCT GGA GCT GCA       68bs (SEQ ID NO:23)
   G CCG CGA CCA AGA CCG CGT CCC GCT CCG CGT CCG AGA CCG CGT CCT CGC CCC AGA CCT CG      60bs (SEQ ID NO:24)
 G   S   G   A   G   S   G   A   G   S   G   A   G   S   G   A  (SEQ ID NO:25)
     PstI
                                         BanHI
                                         Hin3
                                         |
      GGC TAT GGA GCT GGC GCT GGC TCA GGT GCT GGA GCA GGA AGC GGA GCG GGT GCC A        55bs (SEQ ID NO:26)
A CGT CCG ATA CCT CGA CCG CGA CCG AGT CCA CGA CCT CGT CCT TCG CCT CGC CCA CGG TTC GA   63bs (SEQ ID NO:27)
 A   G   Y   G   A   G   A   G   S   G   A   G   A   G   S   G   A  (SEQ ID NO:28)
```

The double stranded DNA sequence is shown in the 5' to 3' direction. The amino acids (g=glycine, a=alanine, s=serine, y=tyrosine) coded by the sequence are shown immediately below each section. Recognition sequences for cleavage by restriction endonucleases are shown above each section.

The above six single-strands were synthesized. After synthesis, the strands of DNA were purified and the homologous strands were annealed. About 1 μl (0.5 μg) of each strand was mixed with 2 μl of 10× AA (see Example 1) buffer and 16 μl of sterilized deionized H₂O in a 1.5 ml polypropylene Eppendorf tube. The tube was placed in a boiling water bath (500 ml in a 1 liter beaker) for 10 min and than the beaker was removed from the hot plate and allowed to cool on the bench to room temperature. This required about 1–2 hr.

Each of the three double stranded sections was cloned separately into M13mp18. Section 1 was ligated between the SmaI and BamHI restriction sites of the multiple-cloning site. Section 2 was ligated between the BamHI and PstI sites. And section 3 was inserted between the PstI and HindIII sites. The respective clones are: M13mp18.1, M13mp18.2, M13mp18.3. The DNA sequence was determined for each cloned section. One representative of each section that had the correct DNA sequence was recovered and became the material for the next step: assembly of the "monomer".

3. Assembly of the "Monomer" of SlpIII

The DNA sections 2 and 3 were isolated by digestion of the M13 clones with restriction enzymes: for section 2, M13mp18.2 was digested with BamHI and Pst1; for section 3, M13mp18.3 was digested with Pst1 and HindIII. The two sections were purified and mixed together in equal molar amounts with M13mp18.1 that had been first digested with BamHI and HindIII. T4 DNA ligase was added to link the homologous overlapping ends in the order 1-2-3. Due to the hybridization specificity of the cohesive ends, the three sections are efficiently linked in only this order. The DNA sequence of the cloned "monomer" in the assembly named M13mp18.1.2.3 was determined to be correct and as shown in Number 2 above.

4. Multimerization of the "Monomer" of SlpIII

In order to prepare large amounts of the "monomer" structural gene we first subcloned the "monomer" into the plasmid vector pUC12. M13mp18.1.2.3 was digested with EcoRI and HindIII restriction enzymes. The SlpIII "monomer" was gel purified and ligated into pUC12 digested with EcoRI and HindIII. The resulting plasmid DNA was prepared, the "monomer" was released from the vector by digestion with BanI REN and the fragment was gel purified.

To create multimers, "monomer" DNA with BanI ends were linked by ligation. The nonpalindromic terminal BanI recognition sequence allows linkage only in a head-to-tail order. The extent of multimerization is monitored by gel electrophoresis and staining the DNA with ethidium bromide. Multimers of more than 20 units have been obtained by this method.

5. Cloning of the Multimers of SlpIII

Plasmid pCQV2 (Queen et al., *J. Appl. Mol. Gen.*, 2:1–10 (1983)) was digested with EcoRI and BamHI restriction endonucleases and a fragment of about 900 bp was purified. This DNA fragment contains the bacteriophage lambda cI-857 repressor gene, the closely linked rightward promoter, $P_R$, and the beginning of the cro gene. Plasmid pSY335 (described as pJF751 in Ferrari et al., *J. Bacteriology*, 161:556–562 (1985)) was digested with EcoRI and BamHI restriction enzymes and subsequently ligated to the DNA fragment of approximately 900 bp of pCQV2. The plasmid obtained from this construction, pSY751, expresses the β-galactosidase gene at 37° C. and 42° C., but not at 30° C. (FIG. 8).

In this approach the SlpIII gene is first cloned into an "adapter" sequence in an intermediate plasmid and then subcloned to the expression systems. The adapter sequence has the following useful features: a unique central BanI REN site, three unique REN sites to either side of BanI, information coding for protein cleavage at either methionine, aspartate-proline or arginine amino acids, and small size. The BanI site is the point of insertion for the SlpIII multimers with BanI ends.

The adapter was synthesized with the Applied Biosystems 380A Synthesizer, cloned in M13mp18 and the DNA sequence verified. The adapter was then subcloned into a specially-constructed plasmid vector that lacked BanI REN sites. The recipient plasmid was made as follows. Plasmid pJH101 (Ferrari et al., 1983) was partially digested with AhaIII restriction enzyme and religated. Transformants of *E. coli* HB101 were selected on medium containing chloramphenicol (12.5 mg/ml). After restriction analysis of several isolates one plasmid was chosen, pSY325 (FIG. 7). This plasmid contains only the chloramphenicol-resistance gene and the replication origin (from pBR322) of pJH101. After digestion to completion with XhoII, pSY325 was ligated with the gel-purified adapter. The result was the adapter-plasmid, pSY937. The new pSY937 REN sites were verified.

The SlpIII multimers were cloned into the BanI site of pSY937 (FIG. 7). Positive clones were identified by colony hybridization and with the lower strand of section 1 of SlpIII as the DNA probe for hybridization (probe sequence shown in Table 2). Positive clones were characterized by gel electrophoresis for the size of the inserted multimer. Finally, the SlpIII sequences were subcloned using the REN site in the flanking adapter regions to specific locations of expression plasmids.

The SlpIII protein had the following amino acid composition:

SlpIII    1178 AA       MW 83,000       (SEQ ID NO:29)

(fM)DPVVLQRRDWENPGVTQLNRLAAHPPFASDPM
GAGS (GAGAGS)₆ GAAGY
[(GAGAGS)₉ GAAGY]₁₈
GAGAGSGAGAGSGAGAMDPGRYQLSAGRYHYQLVWCQK (fM) intends the initiation codon SlpIII Expression Vector Plasmid DNA pSY1086 is a pSY937 derivative containing 19 repeats of SlpIII (3.5 kb). This plasmid DNA was digested with NruI and PvuII and the fragments separated by agarose gel electrophoresis. The purified SlpIII multimer was then cloned in plasmid pSY751 digested with PvuII REN. Several clones were analyzed and one (pSY1008) was chosen to be used in expression experiments and SlpIII purification.

The ampicillin drug resistance gene of pSY1008 was substituted with the Kanamycin marker from pSY1010 (produced by digestion of pSY633 with DraI and SspI and insertion of Kan$^R$ obtained by HincII digestion of pUC4K) and the subsequent plasmid was called pSY1186. By removing the SlpIII portion of plasmid pSY1186 with BanI, a new plasmid, pSY1262, was generated. This plasmid contains a unique BanI site which allows for the direct ligation of fragments containing BanI ends obtained by polymerization of monomers. This plasmid has been used to generate plasmids containing inserts which include the following proteins: SELP1, 2, 3, and Slp4.

Production and Purification of SlpIII Cell Culture

E. coli are cultured in the following medium:

| Medium C | |
|---|---|
| | g/l |
| yeast extract | 20 |
| casamino acids | 20 |
| peptone | 20 |
| gelatin peptone | 20 |
| $KH_2PO_4$ | 2 |
| $K_2HPO_4$ | 2 |
| $Na_2HPO_4.7H_2O$ | 2 |
| glucose | 2 |
| ampicillin | 0.1 |

An overnight culture (500 ml–1 l) which had been grown at 30° C. was used to inoculate 375 L of media contained in a 500 L fermentor. Fermentor conditions include a tachometer reading of 100 rpm, vessel back pressure of 5 psi and an air flow of 170 l/min in order to maintain dissolved $O_2$ at greater than 50%.

Glucose (1 g/l) and ampicillin (0.05 g/l) were added to the fermentation when the culture reached an $OD_{650}$ of 1.0 and again at 2.0. When the culture reached an $OD_{650}$ of 2.0 the temperature was increased to 42° C. for 10 min and then lowered to 38° C. for 2 hours. The culture was then chilled to 10° C. and cells were harvested by centrifugation in a continuous centrifuge and frozen at –70° C. until processed. Yields from two separate fermentations were 7.3 kg and 5.2 kg wet weight of cells.

It should be noted that other media can be used and, with different plasmids, various selection conditions can be imposed (i.e., substitution of kanamycin selection for ampicillin). These conditions have been used in laboratory scale fermentations (10 L volumes).

Cell Lysis

Method 1. Cells were thawed and suspended to a concentration of 1 kg wet weight in 6 L of 50 mM Tris-HCl pH 7.0, 1 mM EDTA and broken by 2 passages through an APR Gaulin cell disrupter at 8000 psi. During this lysis procedure the cells were kept cold with an ice bath. The cell lysate was then centrifuged at 26,000 xg with a continuous centrifuge, such as the T2-28 rotor in a Sorvall RC5B refrigerated centrifuge operated at 4° C. Under these conditions greater than 90% of the SlpIII produced can be found in the pellet. The supernatant did contain some product which could be recovered by $NH_4SO_4$ precipitation as described below. The pellet was extracted with LiBr as described below.

Method 2. Frozen cells were thawed and resuspended to a concentration of 1 kg wet weight in 6 L of 50 mM Tris-HCl pH 7.0, 10 mM EDTA, and 5 mM PMSF to inhibit protease activity. Cells were stirred in this buffer at room temperature for 0.5 to 2 hours, then lysozyme was added to a concentration of 1 g/l and incubation was continued for 20 min. β-Mercaptoethanol was then added to 70 mM and the detergent NP40 was then added to a final concentration of 1% for 20 min while continuously stirring the cell suspension. Then $MgCl_2$ was added to 50 mM followed by DNAse at a concentration of 1 mg/l and incubation was continued at room temperature for 20 min. The cell lysate was then centrifuged as in Method 1 at 26,000 xg in a continuous centrifuge and the supernatant was collected and passed through the continuous centrifuge a second time at 26,000 xg. The supernatant resulting from this second centrifugation contained <5% of the total SlpIII, but what was there could be recovered with $NH_4SO_4$ as described below. The pellets resulting from the 1st and 2nd 26,000 xg centrifugations were combined and extracted with LiBr as described below.

Method 3. For this method, a strain of E. coli is used that contains a second plasmid which encodes the T7 phage lysozyme. This plasmid is compatible with the plasmid encoding the SlpIII gene and the drug resistance determinant. The strain was grown in the same medium and under the same conditions as in the first two methods. However, due to the production of the T7 lysozyme inside the cells, their cell wall was weakened and they could be easily lysed at the completion of the fermentation by the addition of EDTA to >100 mM and NP40 to a concentration of from 0.5 to 1.0% v/v. Lysis could also be achieved by the addition of chloroform (20 ml per liter) instead of NP40. Alternatively, cells could be collected by centrifugation prior to lysis, resuspended to 1 kg wet weight/6 L in Tris-EDTA as described in the first two methods and then lysed by the addition of NP40 or chloroform. Following cell lysis by either method the lysate was centrifuged in a continuous rotor at 26,000 xg as described in the first two methods. As with those methods, LiBr extraction of the pellet and $NH_4SO_4$ precipitation of the supernatant was used to recover the product.

Purification of SlpIII

The pellet obtained by centrifugation of the cell lysate at 26,000 xg as described above was extracted with an equal volume of 9M LiBr. The salt solution was added and the pellet was evenly suspended by stirring at room temperature (RT). The mixture was stirred for 1 hour at RT. After an even suspension was obtained, the mixture was then centrifuged at 26,000 xg in a continuous rotor at 4° C. or at RT to generate a pellet and a supernatant fraction. The supernatant was saved and the pellet was re-extracted with another equal volume of 9M LiBr as above. After mixing for 1 hour the mixture was centrifuged at 26,000 xg and the supernatant from this centrifugation was combined with the supernatant from the first LiBr extraction and allowed to stand at 4° C. overnight. Approximately 90% of the SlpIII contained in the cell lysate 26,000 xg pellet was extracted by LiBr using this procedure.

After the LiBr extract stood overnight at 4° C. a precipitate formed, was removed by centrifugation at 26,000 xg and was discarded. The supernatant was then placed in dialysis bags and dialyzed against several changes of $dH_2O$ for 2 days. As the LiBr was removed by dialysis the SlpIII product precipitated in the dialysis bags. The precipitate was collected by centrifugation and washed 2–3 times with $dH_2O$. The final washed product was centrifuged and dried by lyophilization.

For the recovery of SlpIII from the 26,000 xg supernatant fractions, NH$_4$SO$_4$ precipitation was used. Solid NH$_4$SO$_4$ was slowly added to the sample which was maintained at 4° C., until 38% saturation was achieved (231 g/l). The mixture was then stirred at 4° C. for 2-3 hours. The precipitate was recovered by centrifugation in a continuous flow centrifuge and washed 4-5 times with an equal volume of distilled H$_2$O or with 0.5% SDS in H$_2$O. After each wash the precipitate was recovered by continuous centrifugation. The pellet became increasingly white with successive washes as contaminating protein was removed. SlpIII was recovered as a washed pellet and was dried by lyophilization.

Trypsin Treatment Step of SlpIII

SlpIII was suspended in 50 mM Tris-HCl, pH 8.0, 0.1M NaCl buffer, and was placed in a 37° C. water bath, and TPCK treated trypsin solution was mixed into the suspension. The final trypsin concentration was 0.1%. After 3 hours, the solution was centrifuged at 16,000 xg for 15 min, the pellet was washed with a half equal volume of 0.5% SDS in H$_2$O first, then with distilled water. After each wash the pellet was recovered by centrifugation. The final product was resuspended in water and kept at 4° C. for further analysis.

solvents (Isuka and Young, *Proc. Natl. Acad. Sci. USA* (1966) 55:1175) indicated that SlpIII in solution consists of a mixture of the random and highly ordered structures seen in silk fibroins.

TABLE 4

| Material | a (Å) | b (Å) | c (Å) |
|---|---|---|---|
| (AG)$_n$ | 9.42 | 6.95 | 8.87 |
| (AGAGSG)$_n$ | 9.39 | 6.85 | 9.05 |
| CTP fraction | 9.38 | 6.87 | 9.13 |
| Native fibroin | 9.40 | 6.97 | 9.20 |
|  | 9.44 | 6.95 | 9.30 |
| SlpIII | 9.38 | 6.94 | 8.97 |

Reference in Fraser et al., J. Mol. Biol., (1966) 19:580.

EXAMPLE 4

EBSI Gene Construction

Six oligonucleotide strands were synthesized and purified as described previously.

```
      (HIII)      BanII        StuI
i.  5'AGCTGGGCTCTGGAGTAGGCCTG3'
```
(SEQ ID NO:30)

```
ii. 5'AATTCAGGCCTACTCCAGAGCCC3'
      (ER1)       StuI         BanII
```
(SEQ ID NO:31)

```
       (HIII)     BanII
iii. 5'AGCTTGGTGCCAGGTGTAGGAGTTCCGGGTGTAGGCGTTCCGGGAGTTGG
     TGTACCTGGAGTGGGTGTTCCAGGCGTAGGTGTGC3'
```
(SEQ ID NO:32)

```
       (XmaI)
iv. 5'CCGGGCACACCTACGCCTGGAACACCCACTCCAGGTACACCAACTCCCGGA
     ACGCCTACACCCGGAACTCCTACACCTGGCACCA3'
                                    BanI
```
(SEQ ID NO:33)

```
       (XmaI)                                   AhaII
v.  5'CCGGGGTAGGAGTACCAGGGGTAGGCGTCCCTGGAGCGGGTGCTGGTAG
     CGGCGCAGGCGCGGGCTCCGGAGTAGGGGTGCCG3'
          BanII           BanI
```
(SEQ ID NO:34)

```
       (ERI)     BanI           BanII
vi. 5'AATTCGGCACCCCTACTCCGGAGCCCGCGCCTGCGCCGCTACCAGCACCCG
     CTCCAGGGACGCCTACCCCTGGTACTCCTACC3'
         AhaII
```
(SEQ ID NO:35)

With the trypsin treatment, SlpIII was purified to 99.4% purity.

Physical Measurements of SlpIII

Physical measurements of the purified silk-like proteins have been compared with those of *Bombyx mori* silk in order to establish that the repetitive amino acid polymers produced microbiologically accurately mimic the properties of naturally occurring polymers. Physical measurements were performed to confirm the model of anti-parallel chain pleated sheet conformation for the crystalline regions of *Bombyx mori* silk fibroin (Marsh, Corey and Pauling, *Biochem. Biophys. Acta* (1955) 16; Pauling and Corey, *Proc. Natl. Acad. Sci. USA* (1953) 39:247). Preliminary analysis of x-ray diffraction patterns obtained from Slp films are consistent with those described by Fraser, MacRay, and Steward (1966) (Table 4). Circular Dichroic (CD) and Fourier transform infrared (FTIR) spectroscopic analysis of SlpIII were consistent with a high degree of extended β and β-turn conformations. Comparisons of the spectra obtained from SlpIII with that of naturally occurring silk fibroin in various Oligonucleotide strands (iii), (iv), (v) and (vi) were annealed and ligated with the DNA of plasmid pBSm13(+) (Stratagene) which had been digested with HindIII and EcoRI. The products of this ligation reaction were transformed into *E. coli* strain JM109. Transformant colonies were selected for resistance to ampicillin. Colonies were screened for their hybridization with $^{32}$P-labelled oligonucleotides (iii), (v). Plasmid DNA from several positively hybridizing clones was purified and sequenced. Two of the plasmids, pSY1292 and pSY1293, contained the sequence shown for oligonucleotides (iii), (v) and (iv), (vi). These sequences contained all of the nucleotides present in these synthetic oligonucleotides except one. A G:C basepair was missing at position 7 (iii). The lack of this basepair obstructed one of the BanI sites. In order to introduce a second BanII site at the 5' end of the gene fragment, oligonucleotides (i) and (ii) were annealed and ligated with plasmid pBSm13(+) which had been digested with HindIII and EcoRI. Plasmid DNA from the transformant colonies resistant to ampicillin was purified. Two plasmids, pSY1295 and pSY1296, which were digestible with StuI, a unique site contained in the oligonucleotide sequence, were sequenced. They were both shown to contain the sequence shown for oligonucleotides (i) and (ii). Plasmid DNA From pSY1292 was digested sequentially with HindIII, SI nuclease, and EcoRI. The digestion products were separated by electrophoresis in an agarose gel and the DNA fragment of approximately 150 basepairs was excised from the gel. This DNA fragment was ligated with plasmid DNA pSY1296 which had been digested with StuI and EcoRI. The products of this ligation reaction were transformed into *E. coli* strain JM109 and were selected for resistance to ampicillin. Colonies were screened for hybridization to $^{32}$P-labelled oligonucleotide (v). The plasmid DNA from two positively hybridizing clones was purified and sequenced. These plasmids were named pSY1297 and pSY1298. They contained the following sequence:

from 450 bp to 6,000 bp. The products of the self-ligation were then ligated with plasmid DNA pSY1299 which had been digested with BanII. The products of this ligation reaction were transformed into *E. coli* strain HB101. Transformants were selected for resistance to chloramphenicol. Plasmid DNA from individual transformants was purified and analyzed for increased size due to EBSI multimer DNA insertions. Ten clones (pSY1240–1249) with inserts ranging in size from 1.5 Kbp to 4.4 Kbp were obtained.

Expression of EBSI Multimer Gene

One of these clones, pSY1248, which contained a 4 Kb EBSI multimer gene was recloned in the $\lambda P_R$ expression vector, pSY751. Plasmid DNA from pSY1248 was digested with NruI and PvuII, separated by agarose gel electrophoresis, and the DNA band corresponding to the

```
(HindIII)    BanII                                                                          (SEQ ID NO:36)
AGCTGGGCTCTGGAGTAGGTGTGCCAGGTGTAGGAGTTCCGGGTGTAGGCGTTCCGGGAG    60
TCGACCCGAGACCTCATCCACACGGTCCACATCCTCAAGGCCCACATCCGCAAGGCCCTC XmaI
TTGGTGTACCTGGAGTGGGTGTTCCAGGCGTAGGTGTCCCGGGGTAGGAGTACCAGGGG    120
AACCACATGGACCTCACCCACAAGGTCCGCATCCACACGGGCCCCTACCTCATGGTCCCC BanII
TAGGCGTCCCTGGAGCGGGTGCTGGTAGCGGCGCAGGCGCGGGCTCCGGAGTAGGGGTGC    180
ATCCGCAGGGACCTCGCCCACGACCATCGCCGCGTCCGCGCCCGAGGCCTCATCCCCACG EcoRI
    CGAATTC
    GCTTAAG
```

EBSI Multimer Gene Assembly

The BanI acceptor plasmid pSY937 was modified in order to accept BanII terminal cohesive DNA fragments. Two oligonucleotides were synthesized for this purpose.

EBSI multimer gene was excised and purified by NACS purification. DNA from plasmid pSY751 was digested with PvuII and ligated with the NruI-PvuII fragment from pSY1248. The products of this ligation were transformed into *E. coli* HB101, and the transformants selected for

```
      (BamHI)    DraI   SspI        NruI                 BanII                          (SEQ ID NO:37)
vii.  5'GATCCTATGTTTAAATATTCTCGCGAACGTTTTTGTATGGGCTCGATGTGT TACCGTGCGCATGGATATCAGCTG3'
        NruI     EcoRV   PvuII (BamHI)  PvuII  EcoRV      FspI                  BanII                            (SEQ ID NO:38)
viii. 5'GATCCAGCTGATATCCATGCGCACGGTAACACATCGAGCCCATACAAAAA CGTTCGCGAGAATATTTAAACATAG3'
         NruI     SspI   DraI
```

Oligonucleotides (vii) and (viii) were annealed and ligated with plasmid DNA pSY937 which was digested with BamHI. The products of this ligation were transformed into *E. coli* strain JM109 and colonies were selected for resistance to chloramphenicol. Transformant colonies were screened by hybridization to $^{32}$P-labelled oligonucleotide (vii). Plasmid DNA from two positively hybridizing clones, pSY1299 and pSY1300, contained the sequence shown for oligonucleotides (vii) and (viii), as determined by DNA sequencing.

Plasmid DNA pSY1298 was digested with BanII and the digestion fragments separated by agarose gel electrophoresis. The EBSI gene fragment, approximately 150 base pairs, was excised and purified by electro-elution and ethanol precipitation. Approximately 1 μg of purified fragment was self-ligated in order to produce multimers ranging in size resistance to ampicillin. Two clones were isolated containing the new plasmid pSY1280. *E. coli* cells containing pSY1280 were grown at 30° C. to an $OD_{600}$ of 0.7 and then shifted to 42° C. for 1.5 hours. The proteins produced by these cells was analyzed by SDS-PAGE. The separated proteins were transferred to nitrocellulose paper and detected by immunoreactivity with anti-ELP rabbit serum. A strongly reactive protein band was observed with an apparent molecular weight of 120 kDal.

The Ampicillin drug resistance gene of pSY1280 was substituted with the Kanamycin marker and the subsequent plasmid was called pSY1332. This plasmid was used in fermentation for the purification of EBSI. (See Methods.)

| pSY1332/pSY1280 | EBSI Protein | 1413 AA | MW 113,159 | (SEQ ID NO:39) |

MDPVVLQRRDWENPGVTQLNRLAAHPPFASERFCMGS
[(GVGVP)₈(GAGAGSGAGAGS)₁]₂₆
MCYRAHGYQLSAGRYHYQLVWCQK

Purification of EBSI Protein

E. coli strain HB101 containing plasmid pSY1280 was fermented in 10 L volume. The cells were concentrated by filtration and further harvested by centrifugation. Pelleted cells were stored frozen at −70° C. until processed. Frozen cells were thawed on ice and suspended in 4 ml of 50 mM Tris-HCl pH 7.0, 10 mM EDTA, 5 mM PMSF per gram wet weight of cells. The cells were broken by French pressing twice at 15,000 psi and then cooled to 0° C. The crude lysate was cleared by centrifugation at 26,000 xg for 20 minutes. The supernatant proteins were precipitated by addition of solid ammonium sulfate to 20% of saturation (114 g/l). The precipitate was collected by centrifugation at 10,000 xg for 10 min. The pellet was resuspended in 10 ml of $H_2O$ and dialyzed against 10 mM Tris pH 8.0, 0.15M NaCl at 4° C. The dialyzed solution was digested with 0.1% Trypsin (Sigma) for 1.5 hours at room temperature, and reprecipitated with 20% ammonium sulfate. The precipitated protein was resuspended in $H_2O$ and dialyzed against 10 mM Tris pH 7.0, 1 mM EDTA at 4° C. The protein purity of this sample was analyzed by amino acid composition and determined to be 83%.

Elastic Properties of EBSI Protein

The soluble preparation of semi-purified EBSI protein described above was incubated at 37° C. for 30 min and centrifuged at 10,000 xg for 10 min at room temperature. This treatment caused the EBSI protein to aggregate, become insoluble, and pellet into a translucent solid. The solid was resistant to mechanical disruption either by vortexing or by maceration using a glass rod. The solid could be cut with a razor blade into strips which exhibited a high degree of elasticity. These strips fully retained their shape after repeated extensions and relaxations. They resisted compression with no apparent irreversible deformation of structure.

EBSI Purification

EBSI sample (~70% pure) was dialyzed in 50 mM Tris HCl, 50 mM NaCl, pH 8.0 at 4° C. overnight with one change of buffer. If precipitation was observed, the sample was centrifuged at 27,000 xg for 15 min at 4° C. All remaining steps were performed at 4° C. The supernatant was applied to a DEAE-Sephacel column which had been equilibrated with 50 mM Tris HCl, 50 mM NaCl, pH 8.0. The flow through fractions which contained EBSI were collected and pooled. NaCl was added to the pooled fractions from DEAE-Sephacel column to make a final concentration of 2M NaCl in the sample. Insoluble material was removed by centrifugation at 27,000 xg for 20 min. The supernatant was then loaded onto Phenyl-Sepharose column which was equilibrated with 50 mM sodium phosphate buffer, pH 7.0, with 2M NaCl. The column was washed extensively with buffer until no eluting protein was detected by $A_{280}$. The column was then eluted stepwise with 50 mM sodium phosphate buffer, pH 7.0 and finally with water. The EBSI active fractions were pooled and stored at 4° C. for further analysis.

With the addition of these steps to the previous procedures, 100% pure EBSI was obtained.

EXAMPLE 5

ELPI Construction and Expression

Two oligonucleotide strands were synthesized and purified as described in the Methods section.

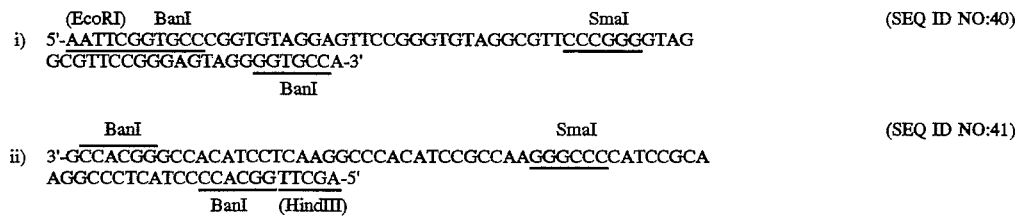

The two oligonucleotide strands were annealed and lighted with the DNA of plasmid pBS m13(+) (Stratagene) which had been digested with RENs HindIII and EcoRI. The products of this ligation reaction were transformed into E. coli strain JM109. Transformant colonies were screened for their hybridization with ³²P-labeled oligonucleotide (i). Plasmid DNA from positively hybridizing clones was purified and sequenced. One plasmid, pSY1287, contained the sequence shown for oligonucleotides (i) and (ii).

Plasmid DNA from pSY1287 was digested with BanI REN and the digestion fragments were separated by agarose gel electrophoresis. The ELPI gene fragment, approximately 60 bp, was excised and purified by NACS column. Approximately 1 µg of purified fragment was self-ligated in order to produce multimers ranging in size from 300 bp to 5000 bp.

The products of the self-ligation were then ligated with plasmid DNA pSY937 which had been digested with REN BanI. The product of this ligation reaction was transformed into E. coli strain HB101. Transformants were selected for resistance to chloramphenicol. Plasmid DNA from individual transformants was purified and analyzed for increased size due to ELPI multiple DNA insertions. Four clones (pSY1388–1391) with inserts ranging in size from 1.0 kbp to 2.5 kbp were obtained. These clones were recloned in the $\lambda P_R$ expression vector pSY751. The clones obtained (pSY1392–1395) were used for expression of ELPI.

The ELPI protein had the following amino acid composition:

pSY1395  ELPI Protein  859 AA  MW 72,555
MDPVVLQRRDWENPGVTQLNRLAAHPPFARNILAIRW
[(VPGVG)$_4$]$_{40}$VPWTRVDLSAGRYHYQLVWCQK  (SEQ ID NO:42)

SELP1 Gene Construction and Expression

Two oligonucleotide strands were synthesized and purified as described in the Methods section.

```
      FspI  PvuII    SnaBI   (PstI)              (SEQ ID NO:43)
(i)  5'-GTGCGCAGCTGGTACGTAGCTGCA-3'

(PstI)     PvuII                          (SEQ ID NO:44)
(ii) 3'-ACGTCiACGCGTCGACCATGCATCG-5'-
             FspI         SnaBI
```

These oligonucleotide strands were annealed and ligated with plasmid pSY1304 which had been digested with PstI REN (pSY1304 differs from pSY857 by having a monomeric unit of SlpIII in place of the trimeric unit of pSY857). Plasmid DNA from transformant colonies resistant to chloramphenicol was purified. One plasmid, pSY1365, which was digestible with REN SnaBI, was sequenced and proven to be correct.

ELPI gene fragment purified as described (ELPI construction and expression) was treated with Mung Bean Nuclease as described by supplier (Stratagene). The DNA fragments mixture was then ligated with plasmid DNA pSY1364 which had been digested sequentially with RENs FspI, SnaBI and calf intestinal phosphatase. The products of this ligation reaction were transformed into E. coli strain HB101 and were selected for resistance to chloramphenicol. Plasmid DNA from individual transformants was purified and analyzed for the ELPI monomer DNA insertion. Two plasmids, pSY1365 A and B, were sequenced. They were both shown to contain the ELPI DNA sequence in the correct orientation.

Plasmid DNA pSY1365 was digested with REN BanI and the DNA fragment containing the SELP1 monomer was gel purified. To create multimers, 1 µg of the SELP1 DNA fragment was self-ligated. Multimers were obtained ranging in size from 500 bp to 10 kbp. The SELP1 multimers were cloned into the BanI site of pSY1262. Positive clones were characterized by gel electrophoresis for the size of the inserted multimer and used for expression and protein analysis.

The products of the ligation mixture were transformed in E. coli strain HB101. Transformants were selected for resistance to chloramphenicol. After restriction analysis of several isolates, one plasmid was chosen, pSY1301, containing a DNA fragment corresponding to the SELP2 monomer gene.

SELP2—Multiple Gene Assembly and Expression

Plasmid DNA pSY1301 was digested with REN BanI and the DNA fragment containing the SELP2 "monomer" was gel purified. To create multimers, 1 µg of the SELP2 DNA fragment was self-ligated. Multimers were obtained greater than 12 kb in size.

The SELP2 multimers were cloned into the BanI site of pSY1262. Positive clones were characterized by gel electrophoresis for the size of the inserted multimer. The clones with inserts ranging in size from 1.5 kb to 11 kb were selected. Plasmid DNA pSY1372 containing an insert of 6 kb (18 repeats) was used for further analysis and protein purification.

SELP2—Protein Purification

E. coli strain HB101 containing plasmid pSY1372 was fermented according to the procedure described in Methods for fermentation. The cells were harvested by centrifugation. Pelleted cells were stored frozen at −70° C. until processed. Frozen cells were thawed on ice and suspended in 4 ml of 50 mM Tris-HCl, pH 7.0, 10 mM EDTA, 5 mM PMSF per gram wet weight of cells. The cells were broken by passing through a Gaulin cell disrupter at 8,000 psi. The crude lysate was cleared by centrifugation at 26,000 xg for 20 min. The supernatant, which contained >75% of the SELP2 protein, was precipitated by addition of 20% ammonium sulfate (114 g/L). The precipitate was collected by centrifugation at 10,000 xg for 10 min. The pellet was resuspended in 10 ml of H$_2$O and dialyzed against 10 mM Tris pH 8.0, 0.15M NaCl at 4° C. The dialyzed material was centrifuged at 26,000 xg for 15 min in order to collect the insoluble fraction of protein which contained approximately 10% of the SELP2 protein. This insoluble protein pellet was washed twice in 0.2% SDS at 50° C. for 30 min with occasional shaking. The insoluble protein was collected each time by centrifugation at 26,000 xg for 15 min followed by a wash of 50% ethanol. The final protein pellet was resuspended in water and analyzed by Western blot analysis and amino acid (SEQ ID NO:45)

pSY1396  SELP1 Protein  2107 AA  MW 148,212
MDPVVLQRRDWENPGVTQLNRLAAHPPFASDPMGAGS(GAGAGS)$_6$
[GAA(VPGVG)$_4$VAAGY(GAGAGS)$_9$]$_{24}$
GAA(VPGVG)$_4$VAAGY(GAGAGS)$_2$GAGAMDPGRYQLSAGRTHYQLVWCQK

SELP2—Monomer Construction

Plasmid DNA pSY1298 was digested with BanII REN and the EBSI gene fragment was purified as described previously. The EBSI monomer fragment was ligated into pSY1304 (pSY937 containing a monomer of SlpIII, constructed as pSY857) which had been digested with BanII REN and treated with calf intestinal phosphatase.

composition. By Western blot the SELP2 protein appeared to be homogeneous in size consistent with its large molecular weight (>150 kDal). By amino acid composition the SELP2 preparation was approximately 80% pure and the observed molar ratio of amino acids (Ser:Gly:Ala:Pro:Val:Tyr) agreed very closely with the expected composition as predicted from the SELP2 sequence present in pSY1372.

(SEQ ID NO:46)

pSY1372  SELP2 Protein  2055 AA  MW 152,354
MDPVVLQRRDWENPGVTQLNRLAAHPPFASDPMGAGS(GAGAGS)$_2$(GVGVP)$_8$
[(GAGAGS)$_6$GAAGY(GAGAGS)$_5$(GVGVP)$_8$]$_{17}$
(GAGAGS)$_6$GAAGY(GAGAGS)$_2$GAGAMDPGRY3LSAGRYHYQLVWCQK SELPQ—Construction and Expression Plasmid DNA pSY1301 was partially digested with REN HaeII and the digestion fragments separated by agarose gel electrophoresis. The larger DNA fragments were excised and purified by NACS column. The purified fragments were self-ligated, the ligation reaction was heated at 70° C. for 15 min to inactivate the T4 DNA ligase and eventually digested with REN PstI. The digestion mixture was then transformed into *E. coli* strain JM109. Transformants were selected for resistance to chloramphenicol. Plasmid DNA from individual transformants was purified and analyzed for: (1) resistance to REN PstI; and (2) deletion of 60 bp HaeII fragment contained within the SELP2 gene fragment. One clone (pSY1377) satisfied both requirements. Plasmid DNA from pSY1377 was digested with REN BanI and the DNA fragment containing the SELP3 monomer was gel purified. To create multimers, 1 μg of the SELP3 DNA fragment was self-ligated. Multimers were obtained ranging in size from 500 bp to 10 kbp. The SELP3 multimers were cloned into the BanI site of pSY1262. Positive clones were characterized by gel electrophoresis for the size of the inserted multimer and used for expression and protein analysis.

FCB-SLPIII (SLPF) Construction and Expression

The SLPIII polymer was chosen as a backbone structure for insertion of a biologically functional sequence because of its predicted structure, allowing for fabrication of useful products; having good structural properties for use in a wide variety of applications; having B-turn structures between interactive strands; and allowing for substitution of the turn sequences with other sequences. The fibronectin cell-binding domain, amino acids 1405–1512, has a strong turn propensity, with the tripeptide RGD providing for cell attachment, predicted to be present within a hydrophilic loop between adjacent B-strands. A 10 amino acid sequence spanning this proposed loop structure (referred to as fibronectin cell-binding or FCB sequence) was chosen to constitute the functional block of amino acids to be inserted within the SLPIII backbone. The insertion site within the SLPIII backbone was chosen to correspond with the amino-acid sequence GAAGY which is also predicted to provide a turn structure (Chou and Fassman, *Biochemistry*, 13:222–244 (1974)). The design allows for conservation of the FCB structure while causing minimal disruption of the SLPIII $(GAGAGS)_9$ B-strand crystal-packing domains.

pSY1397 SELP3 Protein 2257 AA MW 168,535
MDPVVLQRRDWENPGVTQLNRLAAHPPFASDPMGAGS$(GAGAGS)_2$
$[(GVGVP)_8(GAGAGS)_8]_{24}$
$(GVGVP)_8(GAGAGS)_5$GAGAMDPGRYQLSAGRYHYQLVWCQK(SEQ ID NO:47)

SLP4—Construction and Expression

Plasmid DNA from pSY1304 was partially digested with REN HaeII and the digestion fragments separated by agarose gel electrophoresis. The larger DNA fragments were excised and purified by NACS column. The purified fragments were self-ligated, the ligation reaction was heated at 70° C. for 15 min to inactivate the T4 DNA ligase and eventually digested with REN PstI. The digestion mixture was then transformed into *E. coli* strain JM109. Transformants were selected for resistance to chloramphenicol. Plasmid DNA from individual transformants was purified and analyzed for: (1) resistance to REN PstI; and (2) deletion of 60 bp HaeII fragment contained within the SELP2 gene fragment. One clone (pSY1378) satisfied both requirements. Plasmid DNA pSY1378 was digested with REN BanI and the DNA fragment containing the SLP4 monomer was gel purified. To create multimers, 1 μg of SLP4 DNA was self-ligated. Multimers were obtained ranging in size from 300 bp to 6 kbp. The SLP4 multimers were cloned into the BanI site of pSY1262. Positive clones were characterized by gel electrophoresis for the size of the inserted multimer and used for expression and protein analysis.

The SLPIII gene monomer contains a PstI restriction endonuclease site within the sequence encoding the proposed turn structure, GAAGY. This site was used to insert the synthetic DNA encoding the 10 amino acids of the FCB sequence. Two complementary DNA strands comprising the FCB site, 36 bases in length, were synthesized consisting of the sequence shown below:

5'- GTGACTGGCCGTGGTGATAGCCCGGCTAGCGCTGCA -3'(SEQ ID NO:49)
3'- ACGTCACTGACCGGCACCACTATCGGGCCGATCGCG -5'(SEQ ID NO:50)

These oligonucleotides were purified according to the procedures described in Example 1, and cloned into the PstI site of pSY1304. pSY1304 DNA was digested with PstI and ligated with a mixture of the FCB oligonucleotides. The ligation reaction products were transformed into *E. coli* cells. Colonies containing the plasmid were selected on bacterial culture plates containing the antibiotic chloramphenicol. Individual colonies were grown and plasmid DNA purified and analyzed for the presence of the FCB oligonucleotide sequence by restriction digestion with NheI. Plasmids containing this restriction site were subjected to DNA sequencing and two candidates were shown to be correct. The partial nucleotide sequence of one of these, pSY1325, and the encoded amino-acid sequence were as follows:

pSY1398 SLP4 Protein 1059 AA MW 76,231
MDPVVLQRRDWENPGVTQLNRLAAHPPFASDPMGAGS
$[(GAGAGS)_6]_{27}$
$(GAGAGS)_4$GAGAMDPGRYQLSAGRYHYQLVWCQK(SEQ ID NO:48)

```
BanI
GGT GCC GGC AGC GGT GCA GGA GCC GGT TCT GGA GCT GGC
 G   A   G   S   G   A   G   A   G   S   G   A   G

Bam HI
GCG GGC TCT GGC GCG GGC GCA GGA TCC GGC GCA GGC GCT
 A   G   S   G   A   G   A   G   S   G   A   G   A

GGT TCT GGC GCA GGG GCA GGC TCT GGC GCA GGA GCG GGG
 G   S   G   A   G   A   G   S   G   A   G   A   G

Pst I
TCT GGA GCT GCA GTG ACT GGC CGT GGT GAT AGC CCG GCT
 S   G   A   A   V   T   G   R   G   D   S   P   A

Pst I
AGC GCT GCA GGC TAT GGA GCT GGC GCT GGC TCA GGT GCT
 S   A   A   G   Y   G   A   G   A   G   S   G   A

Ban I
GGA GCA GGA AGC GGA GCG GGT GCC(SEQ ID NO:51)
 G   A   G   S   G   A   G(SEQ ID NO:52)
```

The FCB-SLP monomer gene fragment was purified from pSY1325 by digestion with BanI, agarose-gel electrophoresis, and NACS purification (Example 1). The monomer gene fragment was self-ligated and cloned into pSY937 which had been digested with BanI. The products of this ligation were transformed into *E. coli* and selected for growth on chloramphenicol. Plasmid DNA from individual colonies was analyzed for inserts containing multiple FCB-SLP monomer fragments by digestion with NruI and EcoRV and electrophoresis on agarose gels. One clone was identified containing two inserts, one of approximately 2.1 kb and the other of 2.8 kb. Both inserts were cloned individually and transferred to the expression vector pSY751. Plasmid pSY1325 was digested with NruI and PvuII and the 2.1 and 2.8 kb insert bands were purified. These DNA fragments were ligated with pSY751 that had been digested with PvuII. The products of this reaction were transformed into *E. coli* and selected for growth on the antibiotic ampicillin. Plasmid DNA from individual colonies was analyzed by restriction digestion for the presence of the FCB-SLP polymer gene. Two clones were identified, pSY1520 and 1521, containing the 2.1 and the 2.8 kb inserts, respectively.

*E. coli* cells containing pSY1520 and pSY1521 were grown at 30° C. in LB medium containing 50 µg/ml ampicillin to an $OD_{600}$ of 0.7. Production of the FCB-SLP polymer proteins were induced by increasing the culture temperature to 42° C. for 1.5 hrs. The cells were harvested by centrifugation and lysed in sample buffer containing sodium dodecylsulfate (SDS) and β-mercaptoethanol by heating at 100° C. for 5 min. Samples of these lysates corresponding to $5 \times 10^8$ cells were applied to an 8% polyacrylamide gel containing SDS, electrophoresed, and transferred to nitrocellulose filters by electroblotting. The filters were incubated either with anti-SLP or anti-FCB peptide antibody. Specific immunoreactivity with the anti-SLP antibody was observed for a protein band of approximately 75 kd in lysates of pSY1520, 95 kd in lysates of pSY1521, and 120 kd in lysates of the SLPIII clone pSY1186. Reactivity with the anti-FCB antibody was observed only for the two FCB-SLP polymer bands.

```
pSY1520         FCB-SLPIII              767 AA       MW 57,467
        (fM)DPVVLQRRDWENPGVTQLNRLAAHPPFASDPM
            GAGS(GAGAGS)6GAAVTGRGDSPASAAGY
            [(GAGAGS)9GAAVTGRGDSPASAAGY]9
            GAGAGSGAGAGSGAGAMDPGRYQLSAGRYHYQLVWCQK(SEQ ID NO:53)

pSY1521         FCB-SLPIII              1050 AA      MW 72,738
        (fM)DPVVLQRRDWENPGVTQLNRLAAHPPFASDPM
            GAGS(GAGAGS)6GAAVTGRGDSPASAAGY
            [(GAGAGS)9GAAVTGRGDSPASAAGY]13
            GAGAGSGAGAGSGAGAMDPGRYQLSAGRYHYQLVWCQK(SEQ ID NO:54)
```

Plasmid pPT0134 Construction

Two oligonucleotide strands containing multiple cloning sites (MCS) were synthesized and purified as described in Example 1.

```
           FokI                    FokI         ScaI
0.A) 5'- GTGCTGCGGATGCTCGAGATGGTGCATGCATGTACATCCGAGTACTTCGAT (SEQ ID NO:55)
0.B) 3'-      ACGCCTACGAGCTCTACCACGTACGTACATGTAGGCTCATGAAGCTA (SEQ ID NO:56)
```

After annealing, the two oligonucleotide strands were ligated with pSY937 which had been digested with BanI and EcoRV RENs. The product of the ligation mixture was transformed into *E. coli* and selected on bacterial plates containing the antibiotic chloramphenicol. Plasmid DNA from individual colonies was analyzed on agarose gel electrophoresis after digestion with ScaI and StuI RENs. One plasmid, pPT0124, contained the expected DNA fragment.

The new MCS were then moved to plasmid pSY1367. This plasmid is a derivative of pSY1299, which was digested with NciI REN and the large DNA fragment was purified by agarose gel electrophoresis and NACS purification. The purified DNA fragment was treated with DNA Polymerase (Example 1), ligated, then digested with FokI prior to transformation in *E. coli* strain HB101. Plasmid DNA from single colonies was purified and analyzed by restriction digests. One plasmid, pSY1366, was found to be correct and lacking the only FokI site present in pSY1299.

Two oligonucleotide strands were synthesized and purified as described in Example 1:

```
              (BanII)         FokI          (SEQ ID NO:57)
1.A) 5'-CTACATGTGTTACACATCCCGTGC
                                              (SEQ ID NO:58)
1.B) 3'-CCGAGATGTACACAATGTGTAGGGCACG
```

Oligonucleotide strands 1.A and 1.B were annealed and ligated with the DNA of plasmid pSY1366 which had been digested with BanII and FspI RENs. The products of this ligation reaction were transformed into *E. coli* strain HB101. Plasmid DNA from transformed colonies was purified and digested with FokI. Clones which linearized with FokI were sequenced. Plasmid pSY1367 contained the desired MCS sequence and was chosen for subsequent constructions.

Plasmids pPT0124 and pSY1367 were digested with NruI and NcoI and the DNA fragments were purified by agarose gel electrophoresis and NACS purification. The small fragment (approximately 500 bp) from pPT0124 was ligated with the large fragment from pSY1367. The product of the ligation mixture was transformed into *E. coli*. Plasmid DNA from single colonies was purified and analyzed by restriction digests and DNA sequencing. One plasmid, pPT0134, contained the desired sequence and was used as the acceptor vector for further DNA constructions.

SELPF Construction and Expression

Plasmid DNA pSY1521 was digested with BanI REN and the SLPF (FCB-SlpIII) monomer was purified using NACS column (see Example 1). The DNA fragment was ligated with pPT0134 previously digested with FokI REN, treated with calf intestinal phosphatase (see Example 1), and subsequently purified using NACS column. The product of this ligation reaction was transformed into *E. coli* strain HB101. Transformants were selected for resistance to chloramphenicol. Plasmid DNA from transformed colonies was purified and digested with FokI. Clones with the correct restriction pattern were sequenced. Plasmid pPT0141 contained the desired SLPF monomer sequence and was chosen for subsequent constructions.

Plasmid pSY1377 was digested with BanI REN and the SELP3 gene monomer DNA fragment was purified by agarose gel electrophoresis followed by NACS column. The purified SELP3 gene monomer, 268 bp, was ligated with plasmid DNA pPT0141 previously digested with BanI REN and purified using NACS column. The product of this ligation reaction was transformed into *E. coli* strain HB101. Transformants were selected for resistance to chloramphenicol. Plasmid DNA from transformed colonies was purified and digested with FokI. Clones with the correct restriction pattern were sequenced. Plasmid pPT0146 contained the desired SELPF monomer DNA.

Plasmid DNA from pPT0146 was digested with FokI REN and the digestion fragments were separated by agarose gel electrophoresis. The SELPF gene fragment, 477 bp, was excised and purified by NACS column (see Example 1). The purified fragment was ligated with plasmid pSY1262 which had been digested with REN BanI. The product of this ligation reaction was transformed into *E. coli* strain HB101. Transformants were selected for resistance to kanamycin. Plasmid DNA from individual transformants was purified and analyzed for increased size due to SELPF multiple DNA insertion. Several clones were obtained ranging in size from 1 kbp to 6 kbp. One clone pPT0183, with an insert of approximately 2.9 kbp was chosen for expression and protein analysis.

*E. coli* strain HB101 containing plasmid pPT0183 was grown as described in Example 1. The protein produced by these cells was analyzed by SDS-PAGE for detection of reactivity to SLP and ELP antibodies. In every analysis a strong reactive band was observed with an apparent molecular weight of approximately 100 kD.

```
pPT0183     SELPF     1011 AA     MW 79,597
```

MDPVVLQRRDWENPGVTQLNRLAAHPPFASDPM                        (SEQ ID NO:59)
GAGS(GAGAGS)$_2$(GVGVP)$_8$
[(GAGAGS)$_{12}$GAAVTGRGDSPASAAGY(GAGAGS)$_5$(GVGVP)$_8$]$_6$
(GAGAGS)$_{12}$GAAVTGRGDSPASAAGY(GAGAGS)$_2$
GAGAMDPGRYQLSAGRYHYQLVWCQK

Plasmid pPT0285 Construction

Plasmid pACYC184 (Chang, A. Y. C. and Cohen, S. N., *J. Bacteriol.*, 134:1141–1156 (1978)) was digested with BanI REN, purified by agarose gel electrophoresis, and the DNA fragment corresponding to approximately 2,000 bp was further purified using a NACS column. This DNA fragment was filled in using DNA polymerase (see Example 1) and then self-ligated. The products of the ligation mixture were transformed into *E. coli* strain HB101 and selected on bacterial plates containing chloramphenicol at 30 μg/ml. Plasmid DNA from individual colonies was linearized by digestion with Eco47III. One clone, pPT0235, was used as the acceptor vector for subsequent DNA manipulations.

Two oligonucleotide strands were synthesized and purified as described in Example 1:

```
       (Eco47III)PmeI    PmlI    NruI     BanI
StuI EcoRV    SnaBI(SnaI)
1.5'-GCTATGTTTAAACCACGTGTTCGCGATCCGGGTGCCGATCCAGGCCTGCGATATCAGTACGTA      (SEQ ID NO:60)

2.3'-CGATACAAATTTGGTGCACAAGCGCTAGGCCCACGGCTAGGTCCGGACGCTATAGTCATGCAT       (SEQ ID NO:61)

A  M  F  K  P  R  V  R  D  P  G  A  D  P  G  L  R  Y  Q  Y  V     (SEQ ID NO:62)
```

The two oligonucleotide strands were annealed and ligated with the DNA of plasmid pPT0235 which had been digested with Eco47III and SnaI RENs. The product of this ligation reaction was transformed into *E. coli* strain HB101. Plasmid DNA from transformants was purified and digested with EcoRI in combination with Eco47III or SnaI or NruI RENs. Plasmid DNA from two clones that gave the correct digestion pattern was sequenced. One plasmid, designated pPT0285, was found to be correct and chosen for further constructions.

CLP3.7 Construction and Expression

One oligonucleotide strand coding for the CLP 3.7 gene monomer (see Table 5) was synthesized using an Applied Biosystems DNA synthesizer model 381A and a 2000 Å synthesis column supplied by Glen Research. After the synthesis, the 226 base DNA fragment was deprotected and cleaved from the column support by treatment in $NH_4OH$ at 55° C. for 6 hrs.

The PCR reaction was performed as described in Example 1.

The DNA was resuspended and digested with BanI REN as described in Example 1. The digested DNA was purified as described in Example 1, and then ligated with pPT0285 previously digested with BanI, treated with SAP, and purified as described in Example 1. The product of the ligation reaction was transformed into *E. coli* strain HB101. Plasmid DNA from transformants was purified and analyzed as described below. Colonies were picked and transferred onto a plate and into a 0.5 ml microfuge tube containing 50 µl of lysis buffer (1% Tween 20, 10 Tris-HCl pH 8.0, 1 mM EDTA). The tube was closed, incubated at 95° C. for 10 min. and then cooled to room temperature. 5 µl of lysate was added to 45 µl MasterMix (1× PCR buffer as described previously, 5 U Amplitaq, 200 µM dNTPs) in a 0.5 ml Perkin Elmer thin-walled GeneAmp™ reaction tube. Amplification was performed in a Perkin Elmer DNA Thermal cycler model 480 for 30 cycles with the following step cycle of 1 min. each: 95° C., 52° C., and 72° C. Aliquots from the different reactions were analyzed by agarose gel electrophoresis using 1.5% Low Melting Point agarose in 0.5× TAE buffer. Plasmid DNA from the clones showing the correct size insert was purified and analyzed by DNA sequencing. Plasmid pPT0310 contained the desired CLP 3.7 monomer sequence (see Table 6).

TABLE 5

| | |
|---|---|
| 5'-ATGGCAGCGAAAGGGGACCGGTGCCCCGGGTACTCCTGGTCCACAAGGTCTGCCGGGAAGCCCAGGG GCTCCGGGTACTCCAGGTCCGCAAGGCCTGCCGGGTTCACCGGGTGCTCCGGGAACTCCTGGCCCGC AGGGCTTGCCGGGATCCCCAGGTGCACCAGGAACGCCGGGACCTCAGGGTCTTCCGGGTAGCCCTGG TGCCTTTCCGCTAAAGTCCTGCCGT-3' | (SEQ ID NO:63) |

Two additional DNA strands were synthesized to be used as primers for PCR amplification. The synthesis and purification of these DNA primers was performed as described in Example 1. The two strands are:

1. 5'- AAG AAG GAG ATA TCA TAT GGC AGC GAA AGG GGA CC -3'  (SEQ ID NO:64)

2. 5'- CGC AGA TCT TTA AAT TAC GGC AGG ACT TTA GCG GAA A -3'  (SEQ ID NO:65)

TABLE 6

```
    BanI    AvaI/SmaI
5'- GGTGCCCCGGGTACTCCTGGTCCACAAGGTCTGCCGGGAAGCCCA
3'- CCACGGGGCCCATGAGGACCAGGTGTTCCAGACGGCCCTTCGGGT
    G  A  P  G  T  P  G  P  Q  G  L  P  G  S  P

BanII       GsuI            StuI        DraIII
    GGGGCTCCGGGTACTCCAGGTCCGCAAGGCCTGCCGGGTTCACCG
    CCCCGAGGCCCATGAGGTCCAGGCGTTCCGGACGGCCCAAGTGGC
    G  A  P  G  T  P  G  P  Q  G  L  P  G  S  P

BglI       BamHI
    GGTGCTCCGGGAACTCCTGGCCCGCAGGGCTTGCCGGGATCCCCA
    CCACGAGGCCCTTGAGGACCGGGCGTCCCGAACGGCCCTAGGGGT
    G  A  P  G  T  P  G  P  Q  G  L  P  G  S  P

Eco0109I                     BanI
    GGTGCACCAGGAACGCCGGGACCTCAGGGTCTTCCGGGTAGCCCTGGTGCC    -3'
    CCACGTGGTCCTTGCGGCCCTGGAGTCCCAGAAGGCCCATCGGGACCACGG    -5'
    G  A  P  G  T  P  G  P  Q  G  L  P  G  S  P  (G  A)
```

(SEQ ID NO:66)
(SEQ ID NO:67)

CLP3.7 Polymer Construction

Plasmid DNA from pPT0310 was digested with BanI REN and the digestion fragments were separated by agarose gel electrophoresis. The CLP 3.7 gene fragment, 180 bp, was excised and purified by NACS column (see Methods). The purified fragment was ligated with plasmid pSY1262 which had been prepared as follows: pSY1262 plasmid DNA was digested with BanI REN and subsequently treated with Shrimp Alkaline Phosphatase (SAP) as described in Example 1.

The product of this ligation reaction was transformed into *E. coli* strain HB101. Transformants were selected for resistance to kanamycin. Plasmid DNA from individual transformants was purified and analyzed for increased size due to CLP3.7 multiple DNA insertion. Several clones were obtained and two of them containing inserts of approximately 1.25 kbp and 2.6 kbp (pPT0314 and pPT0312 respectively) were chosen to be used for expression of CLP 3.7.

CLP 3.7 Analysis

*E. coli* strain HB101 containing plasmid pPT0312 or pPT0314 were grown as described in Example 1. The proteins produced by these cells were analyzed by SDS-PAGE for detection of reactivity to CLP antibodies. In every analysis a strong reactive band was observed with an apparent molecular weight of 130 kD and 50 kD respectively.

pPT0312     CLP 3.7     837 AA     MW 72,637

(SEQ ID NO:68)
MDPVVLQRRDWENPGVTQLNRLAAHPPFASDPM
[(GAPGTPGPQGLPGSP)$_4$]$_{13}$
GAMDPGRYQLSAGRYHYQLVWCQK (SEQ ID NO:69)
MDPVVLQRRDWENPGVTQLNRLAAHPPFASDPM
[(GAPGTPGPQGLPGSP)$_4$]$_6$
GAMDPGRYQLSAGRYHYQLVWCQK

As is evident from the above results, highly repetitive sequences can be prepared, cloned, and used for expression to produce a wide variety of products which may mimic natural products, such as silk and other proteins and antigens. In addition, novel systems are provided for controlling the expression of the peptide under inducible conditions in a variety of hosts. In this manner, new proteinaceous products can be provided which provide for new properties or may closely mimic the properties of naturally occurring products.

BIBLIOGRAPHY

1. Maniatis, T., Fritsch, E. F. and Sambrook, J. 1982. Molecular Cloning: A Laboratory Manual, Cold Spring Harbor Laboratory, Cold Spring Harbor, N.Y.
2. Laemmli, U. K. 1970. *Nature* (London), 227:680–685.
3. Applied Biosystems User Bulletin. 1984. No. 13.
4. Matteucci, M. D. and Caruthers, M. H. 1981. *Journal Amer. Chem. Soc.*, 103:3185–3319.
5. McBride, L. J. and Caruthers, M. H. 1983. *Tetrahedron Letters*, 24:245–248.
6. Smith. 1980. *Methods in Enzymology*, 65:371–379.
7. Vieira, J. and Messing, J. 1982. *Gene*, 19:259–268.
8. Anagnostopouls, C. and Spizizen, J. 1981. *J.Bacteriol.*, 81:741–746.
9. Davanloo, P., Rosenberg, A. H. Dunn, J. J. and Studier, F. W. 1984. *Proc. Natl. Acad. Sci. USA*, 81:2035–2039.
10. Rosenbluh, A., Banner, C. D. B., Losick, R. and Fitz-James, P. C. 1981. *J. Bacteriol.*, 148:341–351.
11. Sadaie, Y., Burtis, K. C. and Doi, R. 1980. *J. Bacteriol.*, 141:1178–1182.
12. Queen, C. 1983. *J. Applied Molecular Genetics*, 2:1–10.
13. Ferrari, F. A., Trach, K. and Hoch, J. A. 1985. *J. Bacteriol.*, 161:556–562.
14. Johnson, W. C., Moran, C. P. and Losick, T. R. 1983. *Nature* (London), 302:800–804.
15. Studier, W. F. and Moffat, B. A. 1986. *J. Mol. Biol.*, 189:113–130.
16. Goldfarb, D. S., Doi, R. H. and Rodriguez, R. L. 1981. *Nature* (London), 293:309–311.
17. Ferrari, F. A., Nguyen, A., Lang, D. and Hoch, J. A. 1983. *J. Bacteriol.*, 154:1513–1515.
18. Lacey, R. W. and Chopra, I. 1974. *J. Med. Microbiology*, 7:285–297.
19. Norrander, J., Kempe, T. and Messing, J. 1983. *Gene*, 26:101–106.
20. Sanger, F., Nicklen, S. and Coulson, A. R. 1977. *Proc. Natl. Acad. Sci. USA*, 74:5463–5467.
21. Biggin, M. D., Gibson, T. J. and Hong, G. F. 1983. *Proc. Natl. Acad. Sci. USA*, 80:3963–3965.
22. Zagursky, R. J., Baumeister, K., Lomax, N. and Berman, M. L. 1985. *Gene Anal. Techn.*, 2:89–94.
23. Sanger, F. and Coulson, A. R. 1978. *FEBS Letters*, 87:107–110.
24. Sadler, J. R., Techlenburg, M. and J. L. Betz. 1980. Plasmids containing many tandem copies of a synthetic lactose operator. *Gene*, 8:279–300.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

---

What is claimed is:

1. A method of preparing a synthetic DNA sequence of from 900 to 10,000 nt encoding a protein, said DNA sequence comprising repeating units of from 4 to 30 codons, said method comprising:
   (1) synthesizing different pairs of single stranded oligomers, wherein each of the oligomers of a pair overlap except as to any protruding ends;
   (2) hybridizing each pair of single stranded oligomers to provide double stranded segments;
   (3) combining said segments or cloned copies thereof in a cloning vector to form a monomer, where the combined segments are in reading frame;
   (4) excising said monomer from said cloning vector by restriction enzyme digestion; and
   (5) oligomerizing said monomer to provide a multimer comprising at least two monomers.

2. A method according to claim 1, wherein each of said monomers has two different units.

3. A method according to claim 2, wherein different units encode the same amino acid sequence.

4. A method according to claim 2, wherein different units encode different amino acid sequences.

5. A method according to claim 1, wherein each of said units encodes the same amino acid at least twice.

6. A method according to claim 1, wherein said repeating units have from 4 to 15 codons.

7. A method according to claim 1, wherein the DNA of said monomer has been sequenced prior to oligomerizing to form said multimer.

8. A method according to claim 1, wherein at least one repeating unit encodes an amino acid sequence consisting of an amino acid sequence selected from the group consisting of:

GAGAGS, VPGVG, SGAGAG, and AGAGSG.

9. A method according to claim 1, wherein each segment has a 3' terminus which specifically hybridizes to the 5' terminus of the next successive segment and not to its own 5' terminus or has a 5' terminus which specifically hybridizes to the 3' terminus of the next successive segment and not to its own 3' terminus.

10. A method of preparing a synthetic DNA sequence of from 900 to 10,000 nt encoding a protein, said DNA sequence comprising repeating units of from about 4 to 30 codons, said method comprising:

(1) synthesizing different pairs of single stranded oligomers, wherein each of the oligomers of a pair overlap except as to any protruding ends;

(2) hybridizing each pair of single stranded oligomers to provide double stranded segments;

(3) cloning and sequencing said double stranded segments;

(4) combining said segments in a cloning vector to provide a monomer, where the combined segments are in reading frame;

(5) excising said monomer from said cloning vector by restriction enzyme digestion; and (6) oligomerizing said monomer to provide a multimer comprising at least two monomers.

11. A method according to claim 10, wherein said monomer has protruding ends which are cohesive.

12. A method according to claim 10, wherein said repeating units have from 4 to 15 codons.

13. A method according to claim 12, wherein at least one repeating unit encodes an amino acid sequence consisting of an amino acid sequence selected from the group consisting of:

GAGAGS, VPGVG, SGAGAG, and AGAGSG.

14. A method of preparing a synthetic DNA sequence comprising repeating units of from 4 to 30 codons, and consisting of from 900 to 5,000 nucleotides, said method comprising:

(1) synthesizing at least two different pairs of single stranded oligomers, wherein each of the oligomers of a pair overlap except as to any protruding ends;

(2) hybridizing a first pair of single stranded oligomers to provide a first segment and hybridizing successive pairs of single stranded oligomers to provide additional segments;

(3) cloning each of said segments in a cloning vector;

(4) sequencing said segments to ensure the fidelity of replication of said segments;

(5) sequentially adding additional segments with each successive segment in reading frame with the prior segment, to provide a monomer;

(6) cloning said monomer;

(7) excising said monomer from said cloning vector;

(8) oligomerizing said monomer to provide at least one multimer comprising at least two monomers;

wherein the sequences of said segments and vector are selected to permit insertion of said segments and excision of said monomer by restriction enzyme digestion;

(9) inserting said multimer in an expression vector functional for expression in an expression host;

(10) introducing said expression vector into said expression host; and

(11) growing said expression host, whereby the protein encoded by said multimer is expressed.

15. A method according to claim 14, wherein said expression host is *E. coli*.

16. A method of preparing a synthetic DNA sequence comprising repeating units of from 4 to 30 codons for oligomerization to a gene of from 900 to 10,000 nucleotides for expression of a protein, said method comprising:

(a) combining a plurality of DNA segments comprising said repeating units in a cloning vector to provide a monomer having an open reading frame, where all of the DNA in said monomer has been sequenced at least once;

(b) excising said monomer from said cloning vector by restriction enzyme digestion to provide said monomer having complementary ends; and (c) oligomerizing said monomer to provide a multimer having at least two monomers.

17. A method according to claim 16, wherein each of said monomers has two different units.

18. A method according to claim 17, wherein different units encode the same amino acid sequence.

19. A method according to claim 17, wherein different units encode different amino acid sequences.

20. A method according to claim 16, wherein said combining comprises:

(1) synthesizing single stranded oligomers encoding at least 2 repeating units, wherein each of the oligomers of a pair overlap except as to any protruding ends;

(2) hybridizing said pairs of oligomers to provide segments; and (3) cloning said segments.

* * * * *

SEQUENCE LISTING ( 1 ) GENERAL INFORMATION:

( i i i ) NUMBER OF SEQUENCES: 69

( 2 ) INFORMATION FOR SEQ ID NO:1:

( i ) SEQUENCE CHARACTERISTICS:

( A ) LENGTH: 6 amino acids (B) TYPE: amino acid
(C) STRANDEDNESS: single
(D) TOPOLOGY: linear (ii) MOLECULE TYPE: peptide (xi) SEQUENCE DESCRIPTION: SEQ ID NO:1:

Ser Gly Ala Gly Ala Gly
1               5

(2) INFORMATION FOR SEQ ID NO:2:

(i) SEQUENCE CHARACTERISTICS:
  (A) LENGTH: 59 amino acids
  (B) TYPE: amino acid
  (C) STRANDEDNESS: single
  (D) TOPOLOGY: linear (ii) MOLECULE TYPE: peptide (xi) SEQUENCE DESCRIPTION: SEQ ID NO:2:

Gly Ala Gly Ala Gly Ser Gly Ala Gly Ala Gly Ser Gly Ala Gly Ala
1               5                   10                  15
Gly Ser Gly Ala Gly Ala Gly Ser Gly Ala Gly Ala Gly Ser Gly Ala
                20                  25                  30
Gly Ala Gly Ser Gly Ala Gly Ala Gly Ser Gly Ala Gly Ala Gly Ser
                35                  40                  45
Gly Ala Gly Ala Gly Ser Gly Ala Ala Gly Tyr
                50                  55

(2) INFORMATION FOR SEQ ID NO:3:

(i) SEQUENCE CHARACTERISTICS:
  (A) LENGTH: 5 amino acids
  (B) TYPE: amino acid
  (C) STRANDEDNESS: single
  (D) TOPOLOGY: linear (ii) MOLECULE TYPE: peptide (xi) SEQUENCE DESCRIPTION: SEQ ID NO:3:

Gly Val Gly Val Pro
1               5

(2) INFORMATION FOR SEQ ID NO:4:

(i) SEQUENCE CHARACTERISTICS:
  (A) LENGTH: 5 amino acids
  (B) TYPE: amino acid
  (C) STRANDEDNESS: single
  (D) TOPOLOGY: linear (ii) MOLECULE TYPE: peptide (xi) SEQUENCE DESCRIPTION: SEQ ID NO:4:

Val Pro Gly Val Gly
1               5

(2) INFORMATION FOR SEQ ID NO:5:

(i) SEQUENCE CHARACTERISTICS:
  (A) LENGTH: 6 amino acids
  (B) TYPE: amino acid
  (C) STRANDEDNESS: single
  (D) TOPOLOGY: linear (ii) MOLECULE TYPE: peptide (xi) SEQUENCE DESCRIPTION: SEQ ID NO:5:

```
        Ala  Pro  Gly  Val  Gly  Val
        1                 5
```

( 2 ) INFORMATION FOR SEQ ID NO:6:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:6:

```
        Gly  Ala  Gly  Ala  Gly  Ser
        1                 5
```

( 2 ) INFORMATION FOR SEQ ID NO:7:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..7
        ( D ) OTHER INFORMATION: /note= "X = a basic or acidic amino
            acid, particularly K or E."

( x i ) SEQUENCE DESCRIPTION: SEQ ID NO:7:

```
        Lys  Leu  Xaa  Leu  Ala  Glu  Ala
        1                 5
```

( 2 ) INFORMATION FOR SEQ ID NO:8:

( i ) SEQUENCE CHARACTERISTICS:
        ( A ) LENGTH: 53 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:8:

```
        Gly  Ala  Gly  Ala  Gly  Ser  Gly  Ala  Gly  Ala  Gly  Ser  Gly  Ala  Gly  Ala
        1                 5                                10                                15

Gly  Ser  Gly  Ala  Gly  Ala  Gly  Ser  Gly  Ala  Gly  Ala  Gly  Ser  Gly  Ala
                          20                                25                                30

Gly  Ala  Gly  Ser  Gly  Ala  Gly  Ala  Gly  Ser  Gly  Ala  Gly  Ala  Gly  Ser
                          35                                40                                45

Gly  Ala  Ala  Gly  Tyr
                          50
```

( 2 ) INFORMATION FOR SEQ ID NO:9:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:9:

```
        Val  Pro  Gly  Val  Gly
        1              5
```

( 2 ) INFORMATION FOR SEQ ID NO:10:

( i ) SEQUENCE CHARACTERISTICS:
        ( A ) LENGTH: 26 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:10:

```
Tyr  Thr  Ile  Thr  Val  Tyr  Ala  Val  Thr  Gly  Arg  Gly  Asp  Ser  Pro  Ala
1              5                        10                       15

Ser  Ser  Lys  Pro  Ile  Ser  Ile  Asn  Tyr  Cys
               20                       25
```

( 2 ) INFORMATION FOR SEQ ID NO:11:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:11:

GAGAGGAGGA GAGGAG                                           16

( 2 ) INFORMATION FOR SEQ ID NO:12:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:12:

GGTGCGGGCG CAGGAAGT                                     18

( 2 ) INFORMATION FOR SEQ ID NO:13:

( i ) SEQUENCE CHARACTERISTICS:
        ( A ) LENGTH: 18 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:13:

ACCACTTCCT GCGCCCGC                                     18

( 2 ) INFORMATION FOR SEQ ID NO:14:

( i ) SEQUENCE CHARACTERISTICS:
        ( A ) LENGTH: 290 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:14:

```
AAGCTTGGGC  TGCAGGTCAC  CCGGGCGGGC  GCAGGAAGTG  GTGCGGGCGC  AGGAAGTGGT    60

GCGGGCGCAG  GAAGTGGTGC  GGGCGCAGGA  AGTGGTGCGG  GCGCAGGAAG  TGGTGCGGGC   120

GCAGGAAGTG  GTGCGGGCGC  AGGAAGTGGT  GCGGGCGCAG  GAAGTGGTGC  GGGCGCAGGA   180

AGTGGTGCGG  GCGCAGGAAG  TGGTGCGGGC  GCAGGAAGTG  GTGCGGGCGC  AGGAAGTGGT   240

GCGGGCGCAG  GAAGTGGGAC  TCTAGAGGAT  CCCCGGGCGA  GCTCGAATTC               290
```

( 2 ) INFORMATION FOR SEQ ID NO:15:

( i ) SEQUENCE CHARACTERISTICS:
        ( A ) LENGTH: 97 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:15:

```
Lys  Leu  Gly  Leu  Gln  Val  Thr  Arg  Ala  Gly  Ala  Gly  Ser  Gly  Ala  Gly
 1              5                        10                       15

Ala  Gly  Ser  Gly  Ala  Gly  Ala  Gly  Ser  Gly  Ala  Gly  Ala  Gly  Ser  Gly
              20                       25                       30

Ala  Gly  Ala  Gly  Ser  Gly  Ala  Gly  Ala  Gly  Ser  Gly  Ala  Gly  Ala  Gly
         35                       40                       45

Ser  Gly  Ala  Gly  Ala  Gly  Ser  Gly  Ala  Gly  Ala  Gly  Ser  Gly  Ala  Gly
     50                       55                       60

Ala  Gly  Ser  Gly  Ala  Gly  Ala  Gly  Ser  Gly  Ala  Gly  Ala  Gly  Ser  Gly
 65                       70                       75                       80

Ala  Gly  Ala  Gly  Ser  Gly  Thr  Leu  Glu  Asp  Pro  Arg  Ala  Ser  Ser  Asn
              85                       90                       95

Ser
```

( 2 ) INFORMATION FOR SEQ ID NO:16:

( i ) SEQUENCE CHARACTERISTICS:
        ( A ) LENGTH: 37 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:16:

```
Met  Thr  Met  Ile  Thr  Pro  Ser  Leu  Gly  Cys  Arg  Ser  Thr  Leu  Glu  Asp
 1              5                        10                       15

Pro  His  Phe  Arg  Val  Ala  Leu  Ile  Pro  Phe  Phe  Ala  Ala  Phe  Cys  Leu
              20                       25                       30

Pro  Val  Phe  Ala  His
              35
```

( 2 ) INFORMATION FOR SEQ ID NO:17:

( i ) SEQUENCE CHARACTERISTICS:
        ( A ) LENGTH: 84 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:17:

```
Arg  Ala  Gly  Ala  Gly  Ser  Gly  Ala  Gly  Ala  Gly  Ser  Gly  Ala  Gly  Ala
 1              5                        10                       15
```

```
        Gly  Ser  Gly  Ala  Gly  Ala  Gly  Ser  Gly  Ala  Gly  Ala  Gly  Ser  Gly  Ala
                       20                      25                      30

Gly  Ala  Gly  Ser  Gly  Ala  Gly  Ala  Gly  Ser  Gly  Ala  Gly  Ala  Gly  Ser
                       35                      40                      45

Gly  Ala  Gly  Ala  Gly  Ser  Gly  Ala  Gly  Ala  Gly  Ser  Gly  Ala  Gly  Ala
                       50                      55                      60

Gly  Ser  Gly  Ala  Gly  Ala  Gly  Ser  Gly  Ala  Gly  Ala  Gly  Ser  Gly  Thr
        65                             70                      75                      80

Leu  Glu  Asp  Pro
```

( 2 ) INFORMATION FOR SEQ ID NO:18:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:18:

```
        Thr  Ala  Ala  Ala  Thr  Gly
        1                    5
```

( 2 ) INFORMATION FOR SEQ ID NO:19:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:19:

```
        Cys  Ala  Thr  Ala  Thr  Gly
        1                    5
```

( 2 ) INFORMATION FOR SEQ ID NO:20:

( i ) SEQUENCE CHARACTERISTICS:
        ( A ) LENGTH: 61 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:20:

```
GGTGCCGGCA  GCGGTGCAGG  AGCCGGTTCT  GGAGCTGGCG  CGGGCTCTGG  CGCGGGCGCA    60
G                                                                        61
```

( 2 ) INFORMATION FOR SEQ ID NO:21:

( i ) SEQUENCE CHARACTERISTICS:
        ( A ) LENGTH: 65 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:21:

```
GATCCTGCGC  CCGCGCCAGA  GCCCGCGCCA  GCTCCAGAAC  CGGCTCCTGC  ACCGCTGCCG    60
GCACC                                                                    65
```

( 2 ) INFORMATION FOR SEQ ID NO:22:

( i ) SEQUENCE CHARACTERISTICS:
        ( A ) LENGTH: 22 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:22:

```
Gly Ala Gly Ser Gly Ala Gly Ala Gly Ser Gly Ala Gly Ala Gly Ser
 1               5                  10                  15
Gly Ala Gly Ala Gly Ser
            20
```

( 2 ) INFORMATION FOR SEQ ID NO:23:

( i ) SEQUENCE CHARACTERISTICS:
        ( A ) LENGTH: 68 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:23:

```
GATCCGGCGC AGGCGCTGGT TCTGGCGCAG GGGCAGGCTC TGGCGCAGGA GCGGGGTCTG          60
GAGCTGCA                                                                   68
```

( 2 ) INFORMATION FOR SEQ ID NO:24:

( i ) SEQUENCE CHARACTERISTICS:
        ( A ) LENGTH: 60 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:24:

```
GCTCCAGACC CCGCTCCTGC GCCAGAGCCT GCCCCTGCGC CAGAACCAGC GCCTGCGCCG          60
```

( 2 ) INFORMATION FOR SEQ ID NO:25:

( i ) SEQUENCE CHARACTERISTICS:
        ( A ) LENGTH: 23 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:25:

```
Gly Ser Gly Ala Gly Ala Gly Ser Gly Ala Gly Ala Gly Ser Gly Ala
 1               5                  10                  15
Gly Ala Gly Ser Gly Ala Ala
            20
```

( 2 ) INFORMATION FOR SEQ ID NO:26:

( i ) SEQUENCE CHARACTERISTICS:
        ( A ) LENGTH: 55 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:26:

GGCTATGGAG CTGGCGCTGG CTCAGGTGCT GGAGCAGGAA GCGGAGCGGG TGCCA　　　　　55

( 2 ) INFORMATION FOR SEQ ID NO:27:

( i ) SEQUENCE CHARACTERISTICS:
        ( A ) LENGTH: 69 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:27:

AGCTTGGCAC CCGCTCCGCT TCCTGCTCCA GCACCTGAGC CAGCGCCAGC GCCAGCTCCA　　　　　60

TAGCCTGCA　　　　　69

( 2 ) INFORMATION FOR SEQ ID NO:28:

( i ) SEQUENCE CHARACTERISTICS:
        ( A ) LENGTH: 19 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:28:

```
Ala  Gly  Tyr  Gly  Ala  Gly  Ala  Gly  Ser  Gly  Ala  Gly  Ala  Gly  Ser  Gly
 1                   5                            10                           15

Ala  Gly  Ala
```

( 2 ) INFORMATION FOR SEQ ID NO:29:

( i ) SEQUENCE CHARACTERISTICS:
        ( A ) LENGTH: 1177 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:29:

```
Asp  Pro  Val  Val  Leu  Gln  Arg  Arg  Asp  Trp  Glu  Asn  Pro  Gly  Val  Thr
 1                   5                            10                           15

Gln  Leu  Asn  Arg  Leu  Ala  Ala  His  Pro  Pro  Phe  Ala  Ser  Asp  Pro  Met
                    20                            25                           30

Gly  Ala  Gly  Ser  Gly  Ala  Gly  Ala  Gly  Ser  Gly  Ala  Gly  Ala  Gly  Ser
                    35                            40                           45

Gly  Ala  Gly  Ala  Gly  Ser  Gly  Ala  Gly  Ala  Gly  Ser  Gly  Ala  Gly  Ala
                    50                            55                           60

Gly  Ser  Gly  Ala  Gly  Ala  Gly  Ser  Gly  Ala  Ala  Gly  Tyr  Gly  Ala  Gly
 65                                 70                            75                       80

Ala  Gly  Ser  Gly  Ala  Gly  Ala  Gly  Ser  Gly  Ala  Gly  Ala  Gly  Ser  Gly
                         85                            90                            95

Ala  Gly  Ala  Gly  Ser  Gly  Ala  Gly  Ala  Gly  Ser  Gly  Ala  Gly  Ala  Gly
                        100                           105                           110

Ser  Gly  Ala  Gly  Ala  Gly  Ser  Gly  Ala  Gly  Ala  Gly  Ser  Gly  Ala  Gly
                        115                           120                           125

Ala  Gly  Ser  Gly  Ala  Ala  Gly  Tyr  Gly  Ala  Gly  Ala  Gly  Ser  Gly  Ala
                        130                           135                           140
```

```
Gly Ala Gly Ser Gly Ala Gly Ala Gly Ser Gly Ala Gly Ala Gly Ser
145                 150                 155                 160
Gly Ala Gly Ala Gly Ser Gly Ala Gly Ala Gly Ser Gly Ala Gly Ala
                165                 170                 175
Gly Ser Gly Ala Gly Ala Gly Ser Gly Ala Gly Ala Gly Ser Gly Ala
            180                 185                 190
Ala Gly Tyr Gly Ala Gly Ala Gly Ser Gly Ala Gly Ala Gly Ser Gly
        195                 200                 205
Ala Gly Ala Gly Ser Gly Ala Gly Ala Gly Ser Gly Ala Gly Ala Gly
    210                 215                 220
Ser Gly Ala Gly Ala Gly Ser Gly Ala Gly Ala Gly Ser Gly Ala Gly
225                 230                 235                 240
Ala Gly Ser Gly Ala Gly Ala Gly Ser Gly Ala Ala Gly Tyr Gly Ala
                245                 250                 255
Gly Ala Gly Ser Gly Ala Gly Ala Gly Ser Gly Ala Gly Ala Gly Ser
            260                 265                 270
Gly Ala Gly Ala Gly Ser Gly Ala Gly Ala Gly Ser Gly Ala Gly Ala
            275                 280                 285
Gly Ser Gly Ala Gly Ala Gly Ser Gly Ala Gly Ala Gly Ser Gly Ala
        290                 295                 300
Gly Ala Gly Ser Gly Ala Ala Gly Tyr Gly Ala Gly Ala Gly Ser Gly
305                 310                 315                 320
Ala Gly Ala Gly Ser Gly Ala Gly Ala Gly Ser Gly Ala Gly Ala Gly
                325                 330                 335
Ser Gly Ala Gly Ala Gly Ser Gly Ala Gly Ala Gly Ser Gly Ala Gly
                340                 345                 350
Ala Gly Ser Gly Ala Gly Ala Gly Ser Gly Ala Gly Ala Gly Ser Gly
            355                 360                 365
Ala Ala Gly Tyr Gly Ala Gly Ala Gly Ser Gly Ala Gly Ala Gly Ser
    370                 375                 380
Gly Ala Gly Ala Gly Ser Gly Ala Gly Ala Gly Ser Gly Ala Gly Ala
385                 390                 395                 400
Gly Ser Gly Ala Gly Ala Gly Ser Gly Ala Gly Ala Gly Ser Gly Ala
                405                 410                 415
Gly Ala Gly Ser Gly Ala Gly Ala Gly Ser Gly Ala Ala Gly Tyr Gly
            420                 425                 430
Ala Gly Ala Gly Ser Gly Ala Gly Ala Gly Ser Gly Ala Gly Ala Gly
        435                 440                 445
Ser Gly Ala Gly Ala Gly Ser Gly Ala Gly Ala Gly Ser Gly Ala Gly
    450                 455                 460
Ala Gly Ser Gly Ala Gly Ala Gly Ser Gly Ala Gly Ala Gly Ser Gly
465                 470                 475                 480
Ala Gly Ala Gly Ser Gly Ala Ala Gly Tyr Gly Ala Gly Ala Gly Ser
                485                 490                 495
Gly Ala Gly Ala Gly Ser Gly Ala Gly Ala Gly Ser Gly Ala Gly Ala
            500                 505                 510
Gly Ser Gly Ala Gly Ala Gly Ser Gly Ala Gly Ala Gly Ser Gly Ala
        515                 520                 525
Gly Ala Gly Ser Gly Ala Gly Ala Gly Ser Gly Ala Gly Ala Gly Ser
    530                 535                 540
Gly Ala Ala Gly Tyr Gly Ala Gly Ala Gly Ser Gly Ala Gly Ala Gly
545                 550                 555                 560
Ser Gly Ala Gly Ala Gly Ser Gly Ala Gly Ala Gly Ser Gly Ala Gly
```

|     |     |     |     |     |     |     |     |     |     |     |     |     |     |     |
|-----|-----|-----|-----|-----|-----|-----|-----|-----|-----|-----|-----|-----|-----|-----|
|     |     |     |     | 565 |     |     |     | 570 |     |     |     | 575 |     |     |
| Ala | Gly | Ser | Gly | Ala | Gly | Ala | Gly | Ser | Gly | Ala | Gly | Ala | Gly | Ser | Gly |
|     |     |     | 580 |     |     |     |     | 585 |     |     |     | 590 |     |     |
| Ala | Gly | Ala | Gly | Ser | Gly | Ala | Gly | Ala | Gly | Ser | Gly | Ala | Ala | Gly | Tyr |
|     |     | 595 |     |     |     |     | 600 |     |     |     |     | 605 |     |     |
| Gly | Ala | Gly | Ala | Gly | Ser | Gly | Ala | Gly | Ala | Gly | Ser | Gly | Ala | Gly | Ala |
|     | 610 |     |     |     |     | 615 |     |     |     |     | 620 |     |     |     |
| Gly | Ser | Gly | Ala | Gly | Ala | Gly | Ser | Gly | Ala | Gly | Ala | Gly | Ser | Gly | Ala |
| 625 |     |     |     |     | 630 |     |     |     |     | 635 |     |     |     |     | 640 |
| Gly | Ala | Gly | Ser | Gly | Ala | Gly | Ala | Gly | Ser | Gly | Ala | Gly | Ala | Gly | Ser |
|     |     |     |     | 645 |     |     |     |     | 650 |     |     |     |     | 655 |     |
| Gly | Ala | Gly | Ala | Gly | Ser | Gly | Ala | Ala | Gly | Tyr | Gly | Ala | Gly | Ala | Gly |
|     |     |     | 660 |     |     |     |     | 665 |     |     |     |     | 670 |     |     |
| Ser | Gly | Ala | Gly | Ala | Gly | Ser | Gly | Ala | Gly | Ala | Gly | Ser | Gly | Ala | Gly |
|     |     |     | 675 |     |     |     |     | 680 |     |     |     | 685 |     |     |     |
| Ala | Gly | Ser | Gly | Ala | Gly | Ala | Gly | Ser | Gly | Ala | Gly | Ala | Gly | Ser | Gly |
|     | 690 |     |     |     |     | 695 |     |     |     |     | 700 |     |     |     |     |
| Ala | Gly | Ala | Gly | Ser | Gly | Ala | Gly | Ala | Gly | Ser | Gly | Ala | Gly | Ala | Gly |
| 705 |     |     |     |     | 710 |     |     |     |     | 715 |     |     |     |     | 720 |
| Ser | Gly | Ala | Ala | Gly | Tyr | Gly | Ala | Gly | Ala | Gly | Ser | Gly | Ala | Gly | Ala |
|     |     |     |     | 725 |     |     |     |     | 730 |     |     |     |     | 735 |     |
| Gly | Ser | Gly | Ala | Gly | Ala | Gly | Ser | Gly | Ala | Gly | Ala | Gly | Ser | Gly | Ala |
|     |     |     | 740 |     |     |     |     | 745 |     |     |     |     | 750 |     |     |
| Gly | Ala | Gly | Ser | Gly | Ala | Gly | Ala | Gly | Ser | Gly | Ala | Gly | Ala | Gly | Ser |
|     |     |     |     | 755 |     |     |     |     | 760 |     |     |     | 765 |     |     |
| Gly | Ala | Gly | Ala | Gly | Ser | Gly | Ala | Gly | Ala | Gly | Ser | Gly | Ala | Ala | Gly |
|     | 770 |     |     |     |     | 775 |     |     |     |     | 780 |     |     |     |     |
| Tyr | Gly | Ala | Gly | Ala | Gly | Ser | Gly | Ala | Gly | Ala | Gly | Ser | Gly | Ala | Gly |
| 785 |     |     |     |     | 790 |     |     |     |     | 795 |     |     |     |     | 800 |
| Ala | Gly | Ser | Gly | Ala | Gly | Ala | Gly | Ser | Gly | Ala | Gly | Ala | Gly | Ser | Gly |
|     |     |     |     | 805 |     |     |     |     | 810 |     |     |     |     | 815 |     |
| Ala | Gly | Ala | Gly | Ser | Gly | Ala | Gly | Ala | Gly | Ser | Gly | Ala | Gly | Ala | Gly |
|     |     |     | 820 |     |     |     |     | 825 |     |     |     |     | 830 |     |     |
| Ser | Gly | Ala | Gly | Ala | Gly | Ser | Gly | Ala | Ala | Gly | Tyr | Gly | Ala | Gly | Ala |
|     |     |     | 835 |     |     |     |     | 840 |     |     |     |     | 845 |     |     |
| Gly | Ser | Gly | Ala | Gly | Ala | Gly | Ser | Gly | Ala | Gly | Ala | Gly | Ser | Gly | Ala |
|     | 850 |     |     |     |     | 855 |     |     |     |     | 860 |     |     |     |     |
| Gly | Ala | Gly | Ser | Gly | Ala | Gly | Ala | Gly | Ser | Gly | Ala | Gly | Ala | Gly | Ser |
| 865 |     |     |     |     | 870 |     |     |     |     | 875 |     |     |     |     | 880 |
| Gly | Ala | Gly | Ala | Gly | Ser | Gly | Ala | Gly | Ala | Gly | Ser | Gly | Ala | Gly | Ala |
|     |     |     |     | 885 |     |     |     |     | 890 |     |     |     |     | 895 |     |
| Gly | Ser | Gly | Ala | Ala | Gly | Tyr | Gly | Ala | Gly | Ala | Gly | Ser | Gly | Ala | Gly |
|     |     |     | 900 |     |     |     |     | 905 |     |     |     |     | 910 |     |     |
| Ala | Gly | Ser | Gly | Ala | Gly | Ala | Gly | Ser | Gly | Ala | Gly | Ala | Gly | Ser | Gly |
|     |     |     | 915 |     |     |     |     | 920 |     |     |     | 925 |     |     |     |
| Ala | Gly | Ala | Gly | Ser | Gly | Ala | Gly | Ala | Gly | Ser | Gly | Ala | Gly | Ala | Gly |
|     |     | 930 |     |     |     |     | 935 |     |     |     |     | 940 |     |     |     |
| Ser | Gly | Ala | Gly | Ala | Gly | Ser | Gly | Ala | Gly | Ala | Gly | Ser | Gly | Ala | Ala |
| 945 |     |     |     |     | 950 |     |     |     |     | 955 |     |     |     |     | 960 |
| Gly | Tyr | Gly | Ala | Gly | Ala | Gly | Ser | Gly | Ala | Gly | Ala | Gly | Ser | Gly | Ala |
|     |     |     |     | 965 |     |     |     |     | 970 |     |     |     |     | 975 |     |
| Gly | Ala | Gly | Ser | Gly | Ala | Gly | Ala | Gly | Ser | Gly | Ala | Gly | Ala | Gly | Ser |
|     |     |     | 980 |     |     |     |     | 985 |     |     |     |     | 990 |     |     |

```
Gly Ala Gly Ala Gly Ser Gly Ala Gly Ala Gly Ser Gly Ala Gly Ala
        995                 1000                1005

Gly Ser Gly Ala Gly Ala Gly Ser Gly Ala Ala Gly Tyr Gly Ala Gly
        1010                1015                1020

Ala Gly Ser Gly Ala Gly Ala Gly Ser Gly Ala Gly Ala Gly Ser Gly
1025                1030                1035                1040

Ala Gly Ala Gly Ser Gly Ala Gly Ala Gly Ser Gly Ala Gly Ala Gly
                1045                1050                1055

Ser Gly Ala Gly Ala Gly Ser Gly Ala Gly Ala Gly Ser Gly Ala Gly
        1060                1065                1070

Ala Gly Ser Gly Ala Ala Gly Tyr Gly Ala Gly Ala Gly Ser Gly Ala
        1075                1080                1085

Gly Ala Gly Ser Gly Ala Gly Ala Gly Ser Gly Ala Gly Ala Gly Ser
        1090                1095                1100

Gly Ala Gly Ala Gly Ser Gly Ala Gly Ala Gly Ser Gly Ala Gly Ala
1105                1110                1115                1120

Gly Ser Gly Ala Gly Ala Gly Ser Gly Ala Gly Ala Gly Ser Gly Ala
                1125                1130                1135

Ala Gly Tyr Gly Ala Gly Ala Gly Ser Gly Ala Gly Ala Gly Ser Gly
        1140                1145                1150

Ala Gly Ala Met Asp Pro Gly Arg Tyr Gln Leu Ser Ala Gly Arg Tyr
        1155                1160                1165

His Tyr Gln Leu Val Trp Cys Gln Lys
        1170                1175
```

( 2 ) INFORMATION FOR SEQ ID NO:30:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:30:

```
AGCTGGGCTC TGGAGTAGGC CTG                                          23
```

( 2 ) INFORMATION FOR SEQ ID NO:31:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:31:

```
AATTCAGGCC TACTCCAGAG CCC                                          23
```

( 2 ) INFORMATION FOR SEQ ID NO:32:

( i ) SEQUENCE CHARACTERISTICS:
        ( A ) LENGTH: 85 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:32:

```
AGCTTGGTGC CAGGTGTAGG AGTTCCGGGT GTAGGCGTTC CGGGAGTTGG TGTACCTGGA  60
```

GTGGGTGTTC CAGGCGTAGG TGTGC                                                              85

( 2 ) INFORMATION FOR SEQ ID NO:33:

( i ) SEQUENCE CHARACTERISTICS:
        ( A ) LENGTH: 85 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:33:

CCGGGCACAC CTACGCCTGG AACACCCACT CCAGGTACAC CAACTCCCGG AACGCCTACA    60

CCCGGAACTC CTACACCTGG CACCA                                         85

( 2 ) INFORMATION FOR SEQ ID NO:34:

( i ) SEQUENCE CHARACTERISTICS:
        ( A ) LENGTH: 83 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:34:

CCGGGGTAGG AGTACCAGGG GTAGGCGTCC CTGGAGCGGG TGCTGGTAGC GGCGCAGGCG    60

CGGGCTCCGG AGTAGGGGTG CCG                                           83

( 2 ) INFORMATION FOR SEQ ID NO:35:

( i ) SEQUENCE CHARACTERISTICS:
        ( A ) LENGTH: 83 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:35:

AATTCGGCAC CCCTACTCCG GAGCCCGCGC CTGCGCCGCT ACCAGCACCC GCTCCAGGGA    60

CGCCTACCCC TGGTACTCCT ACC                                           83

( 2 ) INFORMATION FOR SEQ ID NO:36:

( i ) SEQUENCE CHARACTERISTICS:
        ( A ) LENGTH: 187 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:36:

AGCTGGGCTC TGGAGTAGGT GTGCCAGGTG TAGGAGTTCC GGGTGTAGGC GTTCCGGGAG    60

TTGGTGTACC TGGAGTGGGT GTTCCAGGCG TAGGTGTGCC CGGGGTAGGA GTACCAGGGG   120

TAGGCGTCCC TGGAGCGGGT GCTGGTAGCG GCGCAGGCGC GGGCTCCGGA GTAGGGGTGC   180

CGAATTC                                                            187

( 2 ) INFORMATION FOR SEQ ID NO:37:

( i ) SEQUENCE CHARACTERISTICS:
        ( A ) LENGTH: 75 base pairs 5,641,648

77

78

-continued ( B ) TYPE: nucleic acid
      ( C ) STRANDEDNESS: single
      ( D ) TOPOLOGY: linear ( i i ) MOLECULE TYPE: cDNA ( x i ) SEQUENCE DESCRIPTION: SEQ ID NO:37:

```
GATCCTATGT TTAAATATTC TCGCGAACGT TTTTGTATGG GCTCGATGTG TTACCGTGCG      60

CATGGATATC AGCTG                                                       75
```

( 2 ) INFORMATION FOR SEQ ID NO:38:

( i ) SEQUENCE CHARACTERISTICS:
      ( A ) LENGTH: 75 base pairs
      ( B ) TYPE: nucleic acid
      ( C ) STRANDEDNESS: single
      ( D ) TOPOLOGY: linear ( i i ) MOLECULE TYPE: cDNA ( x i ) SEQUENCE DESCRIPTION: SEQ ID NO:38:

```
GATCCAGCTG ATATCCATGC GCACGGTAAC ACATCGAGCC CATACAAAAA CGTTCGCGAG      60

AATATTTAAA CATAG                                                       75
```

( 2 ) INFORMATION FOR SEQ ID NO:39:

( i ) SEQUENCE CHARACTERISTICS:
      ( A ) LENGTH: 1413 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:39:

```
Met Asp Pro Val Val Leu Gln Arg Arg Asp Trp Glu Asn Pro Val
 1               5                  10                  15

Thr Gln Leu Asn Arg Leu Ala Ala His Pro Pro Phe Ala Ser Glu Arg
            20                  25                  30

Phe Cys Met Gly Ser Gly Val Gly Val Pro Gly Val Gly Val Pro Gly
            35                  40                  45

Val Gly Val Pro Gly Val Gly Val Pro Gly Val Gly Val Pro Gly Val
        50                  55                  60

Gly Val Pro Gly Val Gly Val Pro Gly Val Gly Val Pro Gly Ala Gly
65                  70                  75                  80

Ala Gly Ser Gly Ala Gly Ala Gly Ser Gly Val Gly Val Pro Gly Val
                85                  90                  95

Gly Val Pro Gly Val Gly Val Pro Gly Val Gly Val Pro Gly Val Gly
               100                 105                 110

Val Pro Gly Val Gly Val Pro Gly Val Gly Val Pro Gly Val Gly Val
               115                 120                 125

Pro Gly Ala Gly Ala Gly Ser Gly Ala Gly Ala Gly Ser Gly Val Gly
               130                 135                 140

Val Pro Gly Val Gly Val Pro Gly Val Gly Val Pro Gly Val Gly Val
145                 150                 155                 160

Pro Gly Val Gly Val Pro Gly Val Gly Val Pro Gly Val Gly Val Pro
                165                 170                 175

Gly Val Gly Val Pro Gly Ala Gly Ala Gly Ser Gly Ala Gly Ala Gly
                180                 185                 190

Ser Gly Val Gly Val Pro Gly Val Gly Val Pro Gly Val Gly Val Pro
                195                 200                 205
```

```
Gly  Val  Gly  Val  Pro  Gly  Val  Gly  Val  Pro  Gly  Val  Gly  Val  Pro  Gly
     210                      215                     220
Val  Gly  Val  Pro  Gly  Val  Gly  Val  Pro  Gly  Ala  Gly  Ala  Gly  Ser  Gly
225                      230                      235                         240
Ala  Gly  Ala  Gly  Ser  Gly  Val  Gly  Val  Pro  Gly  Val  Gly  Val  Pro  Gly
                    245                      250                      255
Val  Gly  Val  Pro  Gly  Val  Gly  Val  Pro  Gly  Val  Gly  Val  Pro  Gly  Val
               260                      265                      270
Gly  Val  Pro  Gly  Val  Gly  Val  Pro  Gly  Val  Gly  Val  Pro  Gly  Ala  Gly
          275                      280                      285
Ala  Gly  Ser  Gly  Ala  Gly  Ala  Gly  Ser  Gly  Val  Gly  Val  Pro  Gly  Val
     290                      295                      300
Gly  Val  Pro  Gly  Val  Gly  Val  Pro  Gly  Val  Gly  Val  Pro  Gly  Val  Gly
305                      310                      315                         320
Val  Pro  Gly  Val  Gly  Val  Pro  Gly  Val  Gly  Val  Pro  Gly  Val  Gly  Val
               325                      330                      335
Pro  Gly  Ala  Gly  Ala  Gly  Ser  Gly  Ala  Gly  Ala  Gly  Ser  Gly  Val  Gly
          340                      345                      350
Val  Pro  Gly  Val  Gly  Val  Pro  Gly  Val  Gly  Val  Pro  Gly  Val  Gly  Val
     355                      360                      365
Pro  Gly  Val  Gly  Val  Pro  Gly  Val  Gly  Val  Pro  Gly  Val  Gly  Val  Pro
370                      375                      380
Gly  Val  Gly  Val  Pro  Gly  Ala  Gly  Ala  Gly  Ser  Gly  Ala  Gly  Ala  Gly
385                      390                      395                         400
Ser  Gly  Val  Gly  Val  Pro  Gly  Val  Gly  Val  Pro  Gly  Val  Gly  Val  Pro
               405                      410                      415
Gly  Val  Gly  Val  Pro  Gly  Val  Gly  Val  Pro  Gly  Val  Gly  Val  Pro  Gly
          420                      425                      430
Val  Gly  Val  Pro  Gly  Val  Gly  Val  Pro  Gly  Ala  Gly  Ala  Gly  Ser  Gly
     435                      440                      445
Ala  Gly  Ala  Gly  Ser  Gly  Val  Gly  Val  Pro  Gly  Val  Gly  Val  Pro  Gly
     450                      455                      460
Val  Gly  Val  Pro  Gly  Val  Gly  Val  Pro  Gly  Val  Gly  Val  Pro  Gly  Val
465                      470                      475                         480
Gly  Val  Pro  Gly  Val  Gly  Val  Pro  Gly  Val  Gly  Val  Pro  Gly  Ala  Gly
               485                      490                      495
Ala  Gly  Ser  Gly  Ala  Gly  Ala  Gly  Ser  Gly  Val  Gly  Val  Pro  Gly  Val
          500                      505                      510
Gly  Val  Pro  Gly  Val  Gly  Val  Pro  Gly  Val  Gly  Val  Pro  Gly  Val  Gly
     515                      520                      525
Val  Pro  Gly  Val  Gly  Val  Pro  Gly  Val  Gly  Val  Pro  Gly  Val  Gly  Val
     530                      535                      540
Pro  Gly  Ala  Gly  Ala  Gly  Ser  Gly  Ala  Gly  Ala  Gly  Ser  Gly  Val  Gly
545                      550                      555                         560
Val  Pro  Gly  Val  Gly  Val  Pro  Gly  Val  Gly  Val  Pro  Gly  Val  Gly  Val
               565                      570                      575
Pro  Gly  Val  Gly  Val  Pro  Gly  Val  Gly  Val  Pro  Gly  Val  Gly  Val  Pro
          580                      585                      590
Gly  Val  Gly  Val  Pro  Gly  Ala  Gly  Ala  Gly  Ser  Gly  Ala  Gly  Ala  Gly
               595                      600                      605
Ser  Gly  Val  Gly  Val  Pro  Gly  Val  Gly  Val  Pro  Gly  Val  Gly  Val  Pro
     610                      615                      620
Gly  Val  Gly  Val  Pro  Gly  Val  Gly  Val  Pro  Gly  Val  Gly  Val  Pro  Gly
```

|  625 |  |  |  |  | 630 |  |  |  |  | 635 |  |  |  |  | 640 |
|---|---|---|---|---|---|---|---|---|---|---|---|---|---|---|---|
| Val | Gly | Val | Pro | Gly | Val | Gly | Val | Pro | Gly | Ala | Gly | Ala | Gly | Ser | Gly |
|  |  |  |  | 645 |  |  |  |  | 650 |  |  |  |  | 655 |  |
| Ala | Gly | Ala | Gly | Ser | Gly | Val | Gly | Val | Pro | Gly | Val | Gly | Val | Pro | Gly |
|  |  |  | 660 |  |  |  |  | 665 |  |  |  |  | 670 |  |  |
| Val | Gly | Val | Pro | Gly | Val | Gly | Val | Pro | Gly | Val | Gly | Val | Pro | Gly | Val |
|  |  | 675 |  |  |  |  | 680 |  |  |  |  | 685 |  |  |  |
| Gly | Val | Pro | Gly | Val | Gly | Val | Pro | Gly | Val | Gly | Val | Pro | Gly | Ala | Gly |
|  | 690 |  |  |  |  | 695 |  |  |  |  | 700 |  |  |  |  |
| Ala | Gly | Ser | Gly | Ala | Gly | Ala | Gly | Ser | Gly | Val | Gly | Val | Pro | Gly | Val |
| 705 |  |  |  |  | 710 |  |  |  |  | 715 |  |  |  |  | 720 |
| Gly | Val | Pro | Gly | Val | Gly | Val | Pro | Gly | Val | Gly | Val | Pro | Gly | Val | Gly |
|  |  |  |  | 725 |  |  |  |  | 730 |  |  |  |  | 735 |  |
| Val | Pro | Gly | Val | Gly | Val | Pro | Gly | Val | Gly | Val | Pro | Gly | Val | Gly | Val |
|  |  |  | 740 |  |  |  |  | 745 |  |  |  |  | 750 |  |  |
| Pro | Gly | Ala | Gly | Ala | Gly | Ser | Gly | Ala | Gly | Ala | Gly | Ser | Gly | Val | Gly |
|  |  | 755 |  |  |  |  | 760 |  |  |  |  | 765 |  |  |  |
| Val | Pro | Gly | Val | Gly | Val | Pro | Gly | Val | Gly | Val | Pro | Gly | Val | Gly | Val |
|  | 770 |  |  |  |  | 775 |  |  |  |  | 780 |  |  |  |  |
| Pro | Gly | Val | Gly | Val | Pro | Gly | Val | Gly | Val | Pro | Gly | Val | Gly | Val | Pro |
| 785 |  |  |  |  | 790 |  |  |  |  | 795 |  |  |  |  | 800 |
| Gly | Val | Gly | Val | Pro | Gly | Ala | Gly | Ala | Gly | Ser | Gly | Ala | Gly | Ala | Gly |
|  |  |  |  | 805 |  |  |  |  | 810 |  |  |  |  | 815 |  |
| Ser | Gly | Val | Gly | Val | Pro | Gly | Val | Gly | Val | Pro | Gly | Val | Gly | Val | Pro |
|  |  |  | 820 |  |  |  |  | 825 |  |  |  |  | 830 |  |  |
| Gly | Val | Gly | Val | Pro | Gly | Val | Gly | Val | Pro | Gly | Val | Gly | Val | Pro | Gly |
|  |  | 835 |  |  |  |  | 840 |  |  |  |  | 845 |  |  |  |
| Val | Gly | Val | Pro | Gly | Val | Gly | Val | Pro | Gly | Ala | Gly | Ala | Gly | Ser | Gly |
|  | 850 |  |  |  |  | 855 |  |  |  |  | 860 |  |  |  |  |
| Ala | Gly | Ala | Gly | Ser | Gly | Val | Gly | Val | Pro | Gly | Val | Gly | Val | Pro | Gly |
| 865 |  |  |  |  | 870 |  |  |  |  | 875 |  |  |  |  | 880 |
| Val | Gly | Val | Pro | Gly | Val | Gly | Val | Pro | Gly | Val | Gly | Val | Pro | Gly | Val |
|  |  |  |  | 885 |  |  |  |  | 890 |  |  |  |  | 895 |  |
| Gly | Val | Pro | Gly | Val | Gly | Val | Pro | Gly | Val | Gly | Val | Pro | Gly | Ala | Gly |
|  |  |  | 900 |  |  |  |  | 905 |  |  |  |  | 910 |  |  |
| Ala | Gly | Ser | Gly | Ala | Gly | Ala | Gly | Ser | Gly | Val | Gly | Val | Pro | Gly | Val |
|  |  | 915 |  |  |  |  | 920 |  |  |  |  | 925 |  |  |  |
| Gly | Val | Pro | Gly | Val | Gly | Val | Pro | Gly | Val | Gly | Val | Pro | Gly | Val | Gly |
|  | 930 |  |  |  |  | 935 |  |  |  |  | 940 |  |  |  |  |
| Val | Pro | Gly | Val | Gly | Val | Pro | Gly | Val | Gly | Val | Pro | Gly | Val | Gly | Val |
| 945 |  |  |  |  | 950 |  |  |  |  | 955 |  |  |  |  | 960 |
| Pro | Gly | Ala | Gly | Ala | Gly | Ser | Gly | Ala | Gly | Ala | Gly | Ser | Gly | Val | Gly |
|  |  |  |  | 965 |  |  |  |  | 970 |  |  |  |  | 975 |  |
| Val | Pro | Gly | Val | Gly | Val | Pro | Gly | Val | Gly | Val | Pro | Gly | Val | Gly | Val |
|  |  |  | 980 |  |  |  |  | 985 |  |  |  |  | 990 |  |  |
| Pro | Gly | Val | Gly | Val | Pro | Gly | Val | Gly | Val | Pro | Gly | Val | Gly | Val | Pro |
|  |  | 995 |  |  |  |  | 1000 |  |  |  |  | 1005 |  |  |  |
| Gly | Val | Gly | Val | Pro | Gly | Ala | Gly | Ala | Gly | Ser | Gly | Ala | Gly | Ala | Gly |
|  | 1010 |  |  |  |  | 1015 |  |  |  |  | 1020 |  |  |  |  |
| Ser | Gly | Val | Gly | Val | Pro | Gly | Val | Gly | Val | Pro | Gly | Val | Gly | Val | Pro |
| 1025 |  |  |  |  | 1030 |  |  |  |  | 1035 |  |  |  |  | 1040 |
| Gly | Val | Gly | Val | Pro | Gly | Val | Gly | Val | Pro | Gly | Val | Gly | Val | Pro | Gly |
|  |  |  |  | 1045 |  |  |  |  | 1050 |  |  |  |  | 1055 |  |

| | | | | | | | | | | | | | | | |
|---|---|---|---|---|---|---|---|---|---|---|---|---|---|---|---|
|Val|Gly|Val|Pro|Gly|Val|Gly|Val|Pro|Gly|Ala|Gly|Ala|Gly|Ser|Gly|
| | | |1060| | | |1065| | | |1070| | | | |
|Ala|Gly|Ala|Gly|Ser|Gly|Val|Gly|Val|Pro|Gly|Val|Gly|Val|Pro|Gly|
| | | |1075| | | |1080| | | |1085| | | | |
|Val|Gly|Val|Pro|Gly|Val|Gly|Val|Pro|Gly|Val|Gly|Val|Pro|Gly|Val|
| | | |1090| | | |1095| | | |1100| | | | |
|Gly|Val|Pro|Gly|Val|Gly|Val|Pro|Gly|Val|Gly|Val|Pro|Gly|Ala|Gly|
|1105| | | |1110| | | |1115| | | | | | |1120|
|Ala|Gly|Ser|Gly|Ala|Gly|Ala|Gly|Ser|Gly|Val|Gly|Val|Pro|Gly|Val|
| | | |1125| | | |1130| | | | | |1135| | |
|Gly|Val|Pro|Gly|Val|Gly|Val|Pro|Gly|Val|Gly|Val|Pro|Gly|Val|Gly|
| | | |1140| | | |1145| | | | |1150| | | |
|Val|Pro|Gly|Val|Gly|Val|Pro|Gly|Val|Gly|Val|Pro|Gly|Val|Gly|Val|
| | | |1155| | | |1160| | | | |1165| | | |
|Pro|Gly|Ala|Gly|Ala|Gly|Ser|Gly|Ala|Gly|Ala|Gly|Ser|Gly|Val|Gly|
| | | |1170| | | |1175| | | | |1180| | | |
|Val|Pro|Gly|Val|Gly|Val|Pro|Gly|Val|Gly|Val|Pro|Gly|Val|Gly|Val|
|1185| | | |1190| | | |1195| | | | | | |1200|
|Pro|Gly|Val|Gly|Val|Pro|Gly|Val|Gly|Val|Pro|Gly|Val|Gly|Val|Pro|
| | | |1205| | | |1210| | | | |1215| | | |
|Gly|Val|Gly|Val|Pro|Gly|Ala|Gly|Ala|Gly|Ser|Gly|Ala|Gly|Ala|Gly|
| | | |1220| | | |1225| | | | |1230| | | |
|Ser|Gly|Val|Gly|Val|Pro|Gly|Val|Gly|Val|Pro|Gly|Val|Gly|Val|Pro|
| | | |1235| | | |1240| | | | |1245| | | |
|Gly|Val|Gly|Val|Pro|Gly|Val|Gly|Val|Pro|Gly|Val|Gly|Val|Pro|Gly|
| | | |1250| | | |1255| | | | |1260| | | |
|Val|Gly|Val|Pro|Gly|Val|Gly|Val|Pro|Gly|Ala|Gly|Ala|Gly|Ser|Gly|
|1265| | | |1270| | | |1275| | | | | | |1280|
|Ala|Gly|Ala|Gly|Ser|Gly|Val|Gly|Val|Pro|Gly|Val|Gly|Val|Pro|Gly|
| | | |1285| | | |1290| | | | |1295| | | |
|Val|Gly|Val|Pro|Gly|Val|Gly|Val|Pro|Gly|Val|Gly|Val|Pro|Gly|Val|
| | | |1300| | | |1305| | | | |1310| | | |
|Gly|Val|Pro|Gly|Val|Gly|Val|Pro|Gly|Val|Gly|Val|Pro|Gly|Ala|Gly|
| | | |1315| | | |1320| | | | |1325| | | |
|Ala|Gly|Ser|Gly|Ala|Gly|Ala|Gly|Ser|Gly|Val|Gly|Val|Pro|Gly|Val|
| | | |1330| | | |1335| | | | |1340| | | |
|Gly|Val|Pro|Gly|Val|Gly|Val|Pro|Gly|Val|Gly|Val|Pro|Gly|Val|Gly|
|1345| | | |1350| | | |1355| | | | | | |1360|
|Val|Pro|Gly|Val|Gly|Val|Pro|Gly|Val|Gly|Val|Pro|Gly|Val|Gly|Val|
| | | |1365| | | |1370| | | | |1375| | | |
|Pro|Gly|Ala|Gly|Ala|Gly|Ser|Gly|Ala|Gly|Ala|Gly|Ser|Met|Cys|Tyr|
| | | |1380| | | |1385| | | | |1390| | | |
|Arg|Ala|His|Gly|Tyr|Gln|Leu|Ser|Ala|Gly|Arg|Tyr|His|Tyr|Gln|Leu|
| | | |1395| | | |1400| | | | |1405| | | |
|Val|Trp|Cys|Gln|Lys| | | | | | | | | | | |
| | | |1410| | | | | | | | | | | | |

( 2 ) INFORMATION FOR SEQ ID NO:40:

( i ) SEQUENCE CHARACTERISTICS:
        ( A ) LENGTH: 72 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:40:

| | | | | | |
|---|---|---|---|---|---|
| AATTCGGTGC | CCGGTGTAGG | AGTTCCGGGT | GTAGGCGTTC | CCGGGGTAGG | CGTTCCGGGA | 60 |
| GTAGGGGTGC | CA | | | | | 72 |

( 2 ) INFORMATION FOR SEQ ID NO:41:

( i ) SEQUENCE CHARACTERISTICS:
        ( A ) LENGTH: 73 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:41:

| | | | | | |
|---|---|---|---|---|---|
| GCCACGGGCC | ACATCCTCAA | GGCCCACATC | CGCCAAGGGC | CCCATCCGCA | AGGCCCTCAT | 60 |
| CCCCACGGTT | CGA | | | | | 73 |

( 2 ) INFORMATION FOR SEQ ID NO:42:

( i ) SEQUENCE CHARACTERISTICS:
        ( A ) LENGTH: 859 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:42:

```
Met Asp Pro Val Val Leu Gln Arg Arg Asp Trp Glu Asn Pro Gly Val
 1               5                  10                  15

Thr Gln Leu Asn Arg Leu Ala Ala His Pro Pro Phe Ala Arg Asn Ile
                20                  25                  30

Leu Ala Ile Arg Trp Val Pro Val Gly Val Pro Gly Val Gly Val
                35                  40                  45

Pro Gly Val Gly Val Pro Gly Val Gly Val Pro Gly Val Gly Val Pro
         50                  55                  60

Gly Val Gly Val Pro Gly Val Gly Val Pro Gly Val Gly Val Pro Gly
 65                  70                  75                  80

Val Gly Val Pro Gly Val Gly Val Pro Gly Val Gly Val Pro Gly Val
                 85                  90                  95

Gly Val Pro Gly Val Gly Val Pro Gly Val Gly Val Pro Gly Val Gly
            100                 105                 110

Val Pro Gly Val Gly Val Pro Gly Val Gly Val Pro Gly Val Gly Val
            115                 120                 125

Pro Gly Val Gly Val Pro Gly Val Gly Val Pro Gly Val Gly Val Pro
        130                 135                 140

Gly Val Gly Val Pro Gly Val Gly Val Pro Gly Val Gly Val Pro Gly
145                 150                 155                 160

Val Gly Val Pro Gly Val Gly Val Pro Gly Val Gly Val Pro Gly Val
                165                 170                 175

Gly Val Pro Gly Val Gly Val Pro Gly Val Gly Val Pro Gly Val Gly
            180                 185                 190

Val Pro Gly Val Gly Val Pro Gly Val Gly Val Pro Gly Val Gly Val
            195                 200                 205

Pro Gly Val Gly Val Pro Gly Val Gly Val Pro Gly Val Gly Val Pro
        210                 215                 220

Gly Val Gly Val Pro Gly Val Gly Val Pro Gly Val Gly Val Pro Gly
225                 230                 235                 240
```

| | | | | | | | | | | | | | | |
|---|---|---|---|---|---|---|---|---|---|---|---|---|---|---|
|Val|Gly|Val|Pro|Gly|Val|Gly|Val|Pro|Gly|Val|Gly|Val|Pro|Gly|Val|
| | | | |245| | | |250| | | |255| | |
|Gly|Val|Pro|Gly|Val|Gly|Val|Pro|Gly|Val|Gly|Val|Pro|Gly|Val|Gly|
| | | |260| | | |265| | | |270| | | |
|Val|Pro|Gly|Val|Gly|Val|Pro|Gly|Val|Gly|Val|Pro|Gly|Val|Gly|Val|
| | |275| | | |280| | | |285| | | | |
|Pro|Gly|Val|Gly|Val|Pro|Gly|Val|Gly|Val|Pro|Gly|Val|Gly|Val|Pro|
| |290| | | |295| | | |300| | | | | |
|Gly|Val|Gly|Val|Pro|Gly|Val|Gly|Val|Pro|Gly|Val|Gly|Val|Pro|Gly|
|305| | | |310| | | |315| | | | |320| |
|Val|Gly|Val|Pro|Gly|Val|Gly|Val|Pro|Gly|Val|Gly|Val|Pro|Gly|Val|
| | | |325| | | |330| | | | |335| | |
|Gly|Val|Pro|Gly|Val|Gly|Val|Pro|Gly|Val|Gly|Val|Pro|Gly|Val|Gly|
| | |340| | | |345| | | |350| | | | |
|Val|Pro|Gly|Val|Gly|Val|Pro|Gly|Val|Gly|Val|Pro|Gly|Val|Gly|Val|
| |355| | | | |360| | | |365| | | | |
|Pro|Gly|Val|Gly|Val|Pro|Gly|Val|Gly|Val|Pro|Gly|Val|Gly|Val|Pro|
|370| | | |375| | | |380| | | | | | |
|Gly|Val|Gly|Val|Pro|Gly|Val|Gly|Val|Pro|Gly|Val|Gly|Val|Pro|Gly|
|385| | | |390| | | |395| | | | | |400|
|Val|Gly|Val|Pro|Gly|Val|Gly|Val|Pro|Gly|Val|Gly|Val|Pro|Gly|Val|
| | | |405| | | |410| | | | |415| | |
|Gly|Val|Pro|Gly|Val|Gly|Val|Pro|Gly|Val|Gly|Val|Pro|Gly|Val|Gly|
| | |420| | | |425| | | |430| | | | |
|Val|Pro|Gly|Val|Gly|Val|Pro|Gly|Val|Gly|Val|Pro|Gly|Val|Gly|Val|
| |435| | | | |440| | | |445| | | | |
|Pro|Gly|Val|Gly|Val|Pro|Gly|Val|Gly|Val|Pro|Gly|Val|Gly|Val|Pro|
|450| | | |455| | | |460| | | | | | |
|Gly|Val|Gly|Val|Pro|Gly|Val|Gly|Val|Pro|Gly|Val|Gly|Val|Pro|Gly|
|465| | | |470| | | |475| | | | | |480|
|Val|Gly|Val|Pro|Gly|Val|Gly|Val|Pro|Gly|Val|Gly|Val|Pro|Gly|Val|
| | | |485| | | |490| | | | |495| | |
|Gly|Val|Pro|Gly|Val|Gly|Val|Pro|Gly|Val|Gly|Val|Pro|Gly|Val|Gly|
| | |500| | | |505| | | |510| | | | |
|Val|Pro|Gly|Val|Gly|Val|Pro|Gly|Val|Gly|Val|Pro|Gly|Val|Gly|Val|
| |515| | | | |520| | | |525| | | | |
|Pro|Gly|Val|Gly|Val|Pro|Gly|Val|Gly|Val|Pro|Gly|Val|Gly|Val|Pro|
|530| | | |535| | | |540| | | | | | |
|Gly|Val|Gly|Val|Pro|Gly|Val|Gly|Val|Pro|Gly|Val|Gly|Val|Pro|Gly|
|545| | | |550| | | |555| | | | | |560|
|Val|Gly|Val|Pro|Gly|Val|Gly|Val|Pro|Gly|Val|Gly|Val|Pro|Gly|Val|
| | | |565| | | |570| | | | |575| | |
|Gly|Val|Pro|Gly|Val|Gly|Val|Pro|Gly|Val|Gly|Val|Pro|Gly|Val|Gly|
| | |580| | | |585| | | |590| | | | |
|Val|Pro|Gly|Val|Gly|Val|Pro|Gly|Val|Gly|Val|Pro|Gly|Val|Gly|Val|
| |595| | | | |600| | | |605| | | | |
|Pro|Gly|Val|Gly|Val|Pro|Gly|Val|Gly|Val|Pro|Gly|Val|Gly|Val|Pro|
|610| | | |615| | | |620| | | | | | |
|Gly|Val|Gly|Val|Pro|Gly|Val|Gly|Val|Pro|Gly|Val|Gly|Val|Pro|Gly|
|625| | | |630| | | |635| | | | | |640|
|Val|Gly|Val|Pro|Gly|Val|Gly|Val|Pro|Gly|Val|Gly|Val|Pro|Gly|Val|
| | | |645| | | |650| | | | |655| | |
|Gly|Val|Pro|Gly|Val|Gly|Val|Pro|Gly|Val|Gly|Val|Pro|Gly|Val|Gly|

-continued

```
                    660                         665                         670
   Val  Pro  Gly  Val  Gly  Val  Pro  Val  Gly  Val  Pro  Gly  Val  Gly  Val
                       675                         680                         685

Pro  Gly  Val  Gly  Val  Pro  Gly  Val  Gly  Val  Pro  Gly  Val  Gly  Val  Pro
                  690                         695                         700

Gly  Val  Gly  Val  Pro  Gly  Val  Gly  Val  Pro  Gly  Val  Gly  Val  Pro  Gly
   705                              710                         715                         720

Val  Gly  Val  Pro  Gly  Val  Gly  Val  Pro  Gly  Val  Gly  Val  Pro  Gly  Val
                            725                         730                         735

Gly  Val  Pro  Gly  Val  Gly  Val  Pro  Gly  Val  Gly  Val  Pro  Gly  Val  Gly
                       740                         745                         750

Val  Pro  Gly  Val  Gly  Val  Pro  Gly  Val  Gly  Val  Pro  Gly  Val  Gly  Val
                  755                         760                         765

Pro  Gly  Val  Gly  Val  Pro  Gly  Val  Gly  Val  Pro  Gly  Val  Gly  Val  Pro
             770                         775                         780

Gly  Val  Gly  Val  Pro  Gly  Val  Gly  Val  Pro  Gly  Val  Gly  Val  Pro  Gly
   785                              790                         795                         800

Val  Gly  Val  Pro  Gly  Val  Gly  Val  Pro  Gly  Val  Gly  Val  Pro  Gly  Val
                            805                         810                         815

Gly  Val  Pro  Gly  Val  Gly  Val  Pro  Gly  Val  Gly  Val  Pro  Gly  Val  Gly
                       820                         825                         830

Val  Pro  Gly  Val  Gly  Val  Pro  Trp  Thr  Arg  Val  Asp  Leu  Ser  Ala  Gly
                  835                         840                         845

Arg  Tyr  His  Tyr  Gln  Leu  Val  Trp  Cys  Gln  Lys
                  850                         855
```

( 2 ) INFORMATION FOR SEQ ID NO:43:

( i ) SEQUENCE CHARACTERISTICS:
        ( A ) LENGTH: 24 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:43:

```
   Gly  Thr  Gly  Cys  Gly  Cys  Ala  Gly  Cys  Thr  Gly  Gly  Thr  Ala  Cys  Gly
   1                   5                             10                        15

Thr  Ala  Gly  Cys  Thr  Gly  Cys  Ala
                       20
```

( 2 ) INFORMATION FOR SEQ ID NO:44:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:44:

GCTACGTACC AGCTGCGCAC TGCA                                                 24

( 2 ) INFORMATION FOR SEQ ID NO:45:

( i ) SEQUENCE CHARACTERISTICS:
        ( A ) LENGTH: 2107 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:45:

| Met | Asp | Pro | Val | Val | Leu | Gln | Arg | Arg | Asp | Trp | Glu | Asn | Pro | Gly | Val |
|---|---|---|---|---|---|---|---|---|---|---|---|---|---|---|---|
| 1 | | | | 5 | | | | | 10 | | | | | 15 | |
| Thr | Gln | Leu | Asn | Arg | Leu | Ala | Ala | His | Pro | Pro | Phe | Ala | Ser | Asp | Pro |
| | | | 20 | | | | | 25 | | | | | 30 | | |
| Met | Gly | Ala | Gly | Ser | Gly | Ala | Gly | Ala | Gly | Ser | Gly | Ala | Gly | Ala | Gly |
| | | | 35 | | | | 40 | | | | | 45 | | | |
| Ser | Gly | Ala | Gly | Ala | Gly | Ser | Gly | Ala | Gly | Ala | Gly | Ser | Gly | Ala | Gly |
| | 50 | | | | | 55 | | | | | 60 | | | | |
| Ala | Gly | Ser | Gly | Ala | Gly | Ala | Gly | Ser | Gly | Ala | Ala | Val | Pro | Gly | Val |
| 65 | | | | | 70 | | | | | 75 | | | | | 80 |
| Gly | Val | Pro | Gly | Val | Gly | Val | Pro | Gly | Val | Gly | Val | Pro | Gly | Val | Gly |
| | | | | 85 | | | | | 90 | | | | | 95 | |
| Val | Ala | Ala | Gly | Tyr | Gly | Ala | Gly | Ala | Gly | Ser | Gly | Ala | Gly | Ala | Gly |
| | | | 100 | | | | | 105 | | | | | 110 | | |
| Ser | Gly | Ala | Gly | Ala | Gly | Ser | Gly | Ala | Gly | Ala | Gly | Ser | Gly | Ala | Gly |
| | | | 115 | | | | | 120 | | | | | 125 | | |
| Ala | Gly | Ser | Gly | Ala | Gly | Ala | Gly | Ser | Gly | Ala | Gly | Ala | Gly | Ser | Gly |
| | 130 | | | | | 135 | | | | | 140 | | | | |
| Ala | Gly | Ala | Gly | Ser | Gly | Ala | Gly | Ala | Gly | Ser | Gly | Ala | Ala | Val | Pro |
| 145 | | | | | 150 | | | | | 155 | | | | | 160 |
| Gly | Val | Gly | Val | Pro | Gly | Val | Gly | Val | Pro | Gly | Val | Gly | Val | Pro | Gly |
| | | | | 165 | | | | | 170 | | | | | 175 | |
| Val | Gly | Val | Ala | Ala | Gly | Tyr | Gly | Ala | Gly | Ala | Gly | Ser | Gly | Ala | Gly |
| | | | 180 | | | | | 185 | | | | | 190 | | |
| Ala | Gly | Ser | Gly | Ala | Gly | Ala | Gly | Ser | Gly | Ala | Gly | Ala | Gly | Ser | Gly |
| | | 195 | | | | | 200 | | | | | 205 | | | |
| Ala | Gly | Ala | Gly | Ser | Gly | Ala | Gly | Ala | Gly | Ser | Gly | Ala | Gly | Ala | Gly |
| | 210 | | | | | 215 | | | | | 220 | | | | |
| Ser | Gly | Ala | Gly | Ala | Gly | Ser | Gly | Ala | Gly | Ala | Gly | Ser | Gly | Ala | Ala |
| 225 | | | | | 230 | | | | | 235 | | | | | 240 |
| Val | Pro | Gly | Val | Gly | Val | Pro | Gly | Val | Gly | Val | Pro | Gly | Val | Gly | Val |
| | | | | 245 | | | | | 250 | | | | | 255 | |
| Pro | Gly | Val | Gly | Val | Ala | Ala | Gly | Tyr | Gly | Ala | Gly | Ala | Gly | Ser | Gly |
| | | | 260 | | | | | 265 | | | | | 270 | | |
| Ala | Gly | Ala | Gly | Ser | Gly | Ala | Gly | Ala | Gly | Ser | Gly | Ala | Gly | Ala | Gly |
| | | 275 | | | | | 280 | | | | | 285 | | | |
| Ser | Gly | Ala | Gly | Ala | Gly | Ser | Gly | Ala | Gly | Ala | Gly | Ser | Gly | Ala | Gly |
| | 290 | | | | | 295 | | | | | 300 | | | | |
| Ala | Gly | Ser | Gly | Ala | Gly | Ala | Gly | Ser | Gly | Ala | Gly | Ala | Gly | Ser | Gly |
| 305 | | | | | 310 | | | | | 315 | | | | | 320 |
| Ala | Ala | Val | Pro | Gly | Val | Gly | Val | Pro | Gly | Val | Gly | Val | Pro | Gly | Val |
| | | | | 325 | | | | | 330 | | | | | 335 | |
| Gly | Val | Pro | Gly | Val | Gly | Val | Ala | Ala | Gly | Tyr | Gly | Ala | Gly | Ala | Gly |
| | | | 340 | | | | | 345 | | | | | 350 | | |
| Ser | Gly | Ala | Gly | Ala | Gly | Ser | Gly | Ala | Gly | Ala | Gly | Ser | Gly | Ala | Gly |
| | | 355 | | | | | 360 | | | | | 365 | | | |
| Ala | Gly | Ser | Gly | Ala | Gly | Ala | Gly | Ser | Gly | Ala | Gly | Ala | Gly | Ser | Gly |
| | 370 | | | | | 375 | | | | | 380 | | | | |
| Ala | Gly | Ala | Gly | Ser | Gly | Ala | Gly | Ala | Gly | Ser | Gly | Ala | Gly | Ala | Gly |
| 385 | | | | | 390 | | | | | 395 | | | | | 400 |

```
Ser  Gly  Ala  Ala  Val  Pro  Gly  Val  Gly  Val  Pro  Gly  Val  Gly  Val  Pro
               405            410                 415
Gly  Val  Gly  Val  Pro  Gly  Val  Gly  Val  Ala  Ala  Gly  Tyr  Gly  Ala  Gly
               420            425                 430
Ala  Gly  Ser  Gly  Ala  Gly  Ala  Gly  Ser  Gly  Ala  Gly  Ala  Gly  Ser  Gly
               435            440                 445
Ala  Gly  Ala  Gly  Ser  Gly  Ala  Gly  Ala  Gly  Ser  Gly  Ala  Gly  Ala  Gly
     450                 455                 460
Ser  Gly  Ala  Gly  Ala  Gly  Ser  Gly  Ala  Gly  Ala  Gly  Ser  Gly  Ala  Gly
465                 470                 475                           480
Ala  Gly  Ser  Gly  Ala  Ala  Val  Pro  Gly  Val  Gly  Val  Pro  Gly  Val  Gly
               485                 490                 495
Val  Pro  Gly  Val  Gly  Val  Pro  Gly  Val  Gly  Val  Ala  Ala  Gly  Tyr  Gly
               500            505                 510
Ala  Gly  Ala  Gly  Ser  Gly  Ala  Gly  Ala  Gly  Ser  Gly  Ala  Gly  Ala  Gly
               515            520                 525
Ser  Gly  Ala  Gly  Ala  Gly  Ser  Gly  Ala  Gly  Ala  Gly  Ser  Gly  Ala  Gly
530                 535                 540
Ala  Gly  Ser  Gly  Ala  Gly  Ala  Gly  Ser  Gly  Ala  Gly  Ala  Gly  Ser  Gly
545                 550                 555                           560
Ala  Gly  Ala  Gly  Ser  Gly  Ala  Ala  Val  Pro  Gly  Val  Gly  Val  Pro  Gly
               565                 570                 575
Val  Gly  Val  Pro  Gly  Val  Gly  Val  Pro  Gly  Val  Gly  Val  Ala  Ala  Gly
               580                 585                 590
Tyr  Gly  Ala  Gly  Ala  Gly  Ser  Gly  Ala  Gly  Ala  Gly  Ser  Gly  Ala  Gly
               595            600                 605
Ala  Gly  Ser  Gly  Ala  Gly  Ala  Gly  Ser  Gly  Ala  Gly  Ala  Gly  Ser  Gly
          610                 615                 620
Ala  Gly  Ala  Gly  Ser  Gly  Ala  Gly  Ala  Gly  Ser  Gly  Ala  Gly  Ala  Gly
625                 630                 635                           640
Ser  Gly  Ala  Gly  Ala  Gly  Ser  Gly  Ala  Ala  Val  Pro  Gly  Val  Gly  Val
               645                 650                 655
Pro  Gly  Val  Gly  Val  Pro  Gly  Val  Gly  Val  Pro  Gly  Val  Gly  Val  Ala
               660                 665                 670
Ala  Gly  Tyr  Gly  Ala  Gly  Ala  Gly  Ser  Gly  Ala  Gly  Ala  Gly  Ser  Gly
               675                 680                 685
Ala  Gly  Ala  Gly  Ser  Gly  Ala  Gly  Ala  Gly  Ser  Gly  Ala  Gly  Ala  Gly
          690                 695                 700
Ser  Gly  Ala  Gly  Ala  Gly  Ser  Gly  Ala  Gly  Ala  Gly  Ser  Gly  Ala  Gly
705                 710                 715                           720
Ala  Gly  Ser  Gly  Ala  Gly  Ala  Gly  Ser  Gly  Ala  Ala  Val  Pro  Gly  Val
               725                 730                 735
Gly  Val  Pro  Gly  Val  Gly  Val  Pro  Gly  Val  Gly  Val  Pro  Gly  Val  Gly
               740                 745                 750
Val  Ala  Ala  Gly  Tyr  Gly  Ala  Gly  Ala  Gly  Ser  Gly  Ala  Gly  Ala  Gly
          755                 760                 765
Ser  Gly  Ala  Gly  Ala  Gly  Ser  Gly  Ala  Gly  Ala  Gly  Ser  Gly  Ala  Gly
          770                 775                 780
Ala  Gly  Ser  Gly  Ala  Gly  Ala  Gly  Ser  Gly  Ala  Gly  Ala  Gly  Ser  Gly
785                 790                 795                           800
Ala  Gly  Ala  Gly  Ser  Gly  Ala  Gly  Ala  Gly  Ser  Gly  Ala  Ala  Val  Pro
               805                 810                 815
Gly  Val  Gly  Val  Pro  Gly  Val  Gly  Val  Pro  Gly  Val  Gly  Val  Pro  Gly
               820                 825                 830
```

```
Val Gly Val Ala Ala Gly Tyr Gly Ala Gly Ala Gly Ser Gly Ala Gly
            835                 840                 845
Ala Gly Ser Gly Ala Gly Ala Gly Ser Gly Ala Gly Ala Gly Ser Gly
            850                 855                 860
Ala Gly Ala Gly Ser Gly Ala Gly Ala Gly Ser Gly Ala Gly Ala Gly
865                 870                 875                 880
Ser Gly Ala Gly Ala Gly Ser Gly Ala Gly Ala Gly Ser Gly Ala Ala
                885                 890                 895
Val Pro Gly Val Gly Val Pro Gly Val Gly Val Pro Gly Val Gly Val
            900                 905                 910
Pro Gly Val Gly Val Ala Ala Gly Tyr Gly Ala Gly Ala Gly Ser Gly
            915                 920                 925
Ala Gly Ala Gly Ser Gly Ala Gly Ala Gly Ser Gly Ala Gly Ala Gly
            930                 935                 940
Ser Gly Ala Gly Ala Gly Ser Gly Ala Gly Ala Gly Ser Gly Ala Gly
945                 950                 955                 960
Ala Gly Ser Gly Ala Gly Ala Gly Ser Gly Ala Gly Ala Gly Ser Gly
                965                 970                 975
Ala Ala Val Pro Gly Val Gly Val Pro Gly Val Gly Val Pro Gly Val
            980                 985                 990
Gly Val Pro Gly Val Gly Val Ala Ala Gly Tyr Gly Ala Gly Ala Gly
            995                1000                1005
Ser Gly Ala Gly Ala Gly Ser Gly Ala Gly Ala Gly Ser Gly Ala Gly
           1010                1015                1020
Ala Gly Ser Gly Ala Gly Ala Gly Ser Gly Ala Gly Ala Gly Ser Gly
1025                1030                1035                1040
Ala Gly Ala Gly Ser Gly Ala Gly Ala Gly Ser Gly Ala Gly Ala Gly
           1045                1050                1055
Ser Gly Ala Ala Val Pro Gly Val Gly Val Pro Gly Val Gly Val Pro
           1060                1065                1070
Gly Val Gly Val Pro Gly Val Gly Val Ala Ala Gly Tyr Gly Ala Gly
           1075                1080                1085
Ala Gly Ser Gly Ala Gly Ala Gly Ser Gly Ala Gly Ala Gly Ser Gly
           1090                1095                1100
Ala Gly Ala Gly Ser Gly Ala Gly Ala Gly Ser Gly Ala Gly Ala Gly
1105                1110                1115                1120
Ser Gly Ala Gly Ala Gly Ser Gly Ala Gly Ala Gly Ser Gly Ala Gly
           1125                1130                1135
Ala Gly Ser Gly Ala Ala Val Pro Gly Val Gly Val Pro Gly Val Gly
           1140                1145                1150
Val Pro Gly Val Gly Val Pro Gly Val Gly Val Ala Ala Gly Tyr Gly
           1155                1160                1165
Ala Gly Ala Gly Ser Gly Ala Gly Ala Gly Ser Gly Ala Gly Ala Gly
           1170                1175                1180
Ser Gly Ala Gly Ala Gly Ser Gly Ala Gly Ala Gly Ser Gly Ala Gly
1185                1190                1195                1200
Ala Gly Ser Gly Ala Gly Ala Gly Ser Gly Ala Gly Ala Gly Ser Gly
           1205                1210                1215
Ala Gly Ala Gly Ser Gly Ala Ala Val Pro Gly Val Gly Val Pro Gly
           1220                1225                1230
Val Gly Val Pro Gly Val Gly Val Pro Gly Val Gly Val Ala Ala Gly
           1235                1240                1245
Tyr Gly Ala Gly Ala Gly Ser Gly Ala Gly Ala Gly Ser Gly Ala Gly
```

-continued

```
            1250                    1255                    1260
Ala Gly Ser Gly Ala Gly Ala Gly Ser Gly Ala Gly Ala Gly Ser Gly
1265                    1270                    1275                    1280
Ala Gly Ala Gly Ser Gly Ala Gly Ala Gly Ser Gly Ala Gly Ala Gly
            1285                    1290                    1295
Ser Gly Ala Gly Ala Gly Ser Gly Ala Ala Val Pro Gly Val Gly Val
            1300                    1305                    1310
Pro Gly Val Gly Val Pro Gly Val Gly Val Pro Gly Val Gly Val Ala
            1315                    1320                    1325
Ala Gly Tyr Gly Ala Gly Ala Gly Ser Gly Ala Gly Ala Gly Ser Gly
            1330                    1335                    1340
Ala Gly Ala Gly Ser Gly Ala Gly Ala Gly Ser Gly Ala Gly Ala Gly
1345                    1350                    1355                    1360
Ser Gly Ala Gly Ala Gly Ser Gly Ala Gly Ala Gly Ser Gly Ala Gly
            1365                    1370                    1375
Ala Gly Ser Gly Ala Gly Ala Gly Ser Gly Ala Ala Val Pro Gly Val
            1380                    1385                    1390
Gly Val Pro Gly Val Gly Val Pro Gly Val Gly Val Pro Gly Val Gly
            1395                    1400                    1405
Val Ala Ala Gly Tyr Gly Ala Gly Ala Gly Ser Gly Ala Gly Ala Gly
            1410                    1415                    1420
Ser Gly Ala Gly Ala Gly Ser Gly Ala Gly Ala Gly Ser Gly Ala Gly
1425                    1430                    1435                    1440
Ala Gly Ser Gly Ala Gly Ala Gly Ser Gly Ala Gly Ala Gly Ser Gly
            1445                    1450                    1455
Ala Gly Ala Gly Ser Gly Ala Gly Ala Gly Ser Gly Ala Ala Val Pro
            1460                    1465                    1470
Gly Val Gly Val Pro Gly Val Gly Val Pro Gly Val Gly Val Pro Gly
            1475                    1480                    1485
Val Gly Val Ala Ala Gly Tyr Gly Ala Gly Ala Gly Ser Gly Ala Gly
            1490                    1495                    1500
Ala Gly Ser Gly Ala Gly Ala Gly Ser Gly Ala Gly Ala Gly Ser Gly
1505                    1510                    1515                    1520
Ala Gly Ala Gly Ser Gly Ala Gly Ala Gly Ser Gly Ala Gly Ala Gly
            1525                    1530                    1535
Ser Gly Ala Gly Ala Gly Ser Gly Ala Gly Ala Gly Ser Gly Ala Ala
            1540                    1545                    1550
Val Pro Gly Val Gly Val Pro Gly Val Gly Val Pro Gly Val Gly Val
            1555                    1560                    1565
Pro Gly Val Gly Val Ala Ala Gly Tyr Gly Ala Gly Ala Gly Ser Gly
            1570                    1575                    1580
Ala Gly Ala Gly Ser Gly Ala Gly Ala Gly Ser Gly Ala Gly Ala Gly
1585                    1590                    1595                    1600
Ser Gly Ala Gly Ala Gly Ser Gly Ala Gly Ala Gly Ser Gly Ala Gly
            1605                    1610                    1615
Ala Gly Ser Gly Ala Gly Ala Gly Ser Gly Ala Gly Ala Gly Ser Gly
            1620                    1625                    1630
Ala Ala Val Pro Gly Val Gly Val Pro Gly Val Gly Val Pro Gly Val
            1635                    1640                    1645
Gly Val Pro Gly Val Gly Val Ala Ala Gly Tyr Gly Ala Gly Ala Gly
            1650                    1655                    1660
Ser Gly Ala Gly Ala Gly Ser Gly Ala Gly Ala Gly Ser Gly Ala Gly
1665                    1670                    1675                    1680
```

```
Ala Gly Ser Gly Ala Gly Ala Gly Ser Gly Ala Gly Ala Gly Ser Gly
              1685                1690                1695
Ala Gly Ala Gly Ser Gly Ala Gly Ala Gly Ser Gly Ala Gly Ala Gly
         1700                1705                1710
Ser Gly Ala Ala Val Pro Gly Val Gly Val Pro Gly Val Gly Val Pro
     1715                1720                1725
Gly Val Gly Val Pro Gly Val Gly Val Ala Ala Gly Tyr Gly Ala Gly
         1730                1735                1740
Ala Gly Ser Gly Ala Gly Ala Gly Ser Gly Ala Gly Ala Gly Ser Gly
1745                1750                1755                1760
Ala Gly Ala Gly Ser Gly Ala Gly Ala Gly Ser Gly Ala Gly Ala Gly
              1765                1770                1775
Ser Gly Ala Gly Ala Gly Ser Gly Ala Gly Ala Gly Ser Gly Ala Gly
         1780                1785                1790
Ala Gly Ser Gly Ala Ala Val Pro Gly Val Gly Val Pro Gly Val Gly
     1795                1800                1805
Val Pro Gly Val Gly Val Pro Gly Val Gly Val Ala Ala Gly Tyr Gly
         1810                1815                1820
Ala Gly Ala Gly Ser Gly Ala Gly Ala Gly Ser Gly Ala Gly Ala Gly
1825                1830                1835                1840
Ser Gly Ala Gly Ala Gly Ser Gly Ala Gly Ala Gly Ser Gly Ala Gly
              1845                1850                1855
Ala Gly Ser Gly Ala Gly Ala Gly Ser Gly Ala Gly Ala Gly Ser Gly
              1860                1865                1870
Ala Gly Ala Gly Ser Gly Ala Ala Val Pro Gly Val Gly Val Pro Gly
         1875                1880                1885
Val Gly Val Pro Gly Val Gly Val Pro Gly Val Gly Val Ala Ala Gly
         1890                1895                1900
Tyr Gly Ala Gly Ala Gly Ser Gly Ala Gly Ala Gly Ser Gly Ala Gly
1905                1910                1915                1920
Ala Gly Ser Gly Ala Gly Ala Gly Ser Gly Ala Gly Ala Gly Ser Gly
              1925                1930                1935
Ala Gly Ala Gly Ser Gly Ala Gly Ala Gly Ser Gly Ala Gly Ala Gly
         1940                1945                1950
Ser Gly Ala Gly Ala Gly Ser Gly Ala Ala Val Pro Gly Val Gly Val
         1955                1960                1965
Pro Gly Val Gly Val Pro Gly Val Gly Val Pro Gly Val Gly Val Ala
     1970                1975                1980
Ala Gly Tyr Gly Ala Gly Ala Gly Ser Gly Ala Gly Ala Gly Ser Gly
1985                1990                1995                2000
Ala Gly Ala Gly Ser Gly Ala Gly Ala Gly Ser Gly Ala Gly Ala Gly
              2005                2010                2015
Ser Gly Ala Gly Ala Gly Ser Gly Ala Gly Ala Gly Ser Gly Ala Gly
         2020                2025                2030
Ala Gly Ser Gly Ala Gly Ala Gly Ser Gly Ala Ala Val Pro Gly Val
     2035                2040                2045
Gly Val Pro Gly Val Gly Val Pro Gly Val Gly Val Pro Gly Val Gly
     2050                2055                2060
Val Ala Ala Gly Tyr Gly Ala Gly Ala Gly Ser Gly Ala Gly Ala Gly
2065                2070                2075                2080
Ser Gly Ala Gly Ala Met Asp Pro Gly Arg Tyr Gln Leu Ser Ala Gly
              2085                2090                2095
Arg Thr His Tyr Gln Leu Val Trp Cys Gln Lys
              2100                2105
```

( 2 ) INFORMATION FOR SEQ ID NO:46:

( i ) SEQUENCE CHARACTERISTICS:
        ( A ) LENGTH: 2055 amino acids
        ( B ) TYPE: amino acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:46:

```
Met  Asp  Pro  Val  Val  Leu  Gln  Arg  Arg  Asp  Trp  Glu  Asn  Pro  Gly  Val
 1              5                        10                       15

Thr  Gln  Leu  Asn  Arg  Leu  Ala  Ala  His  Pro  Pro  Phe  Ala  Ser  Asp  Pro
              20                        25                       30

Met  Gly  Ala  Gly  Ser  Gly  Ala  Gly  Ala  Gly  Ser  Gly  Ala  Gly  Ala  Gly
              35                        40                       45

Ser  Gly  Val  Gly  Val  Pro  Gly  Val  Gly  Val  Pro  Gly  Val  Gly  Val  Pro
              50                        55                       60

Gly  Val  Gly  Val  Pro  Gly  Val  Gly  Val  Pro  Gly  Val  Gly  Val  Pro  Gly
 65                       70                        75                       80

Val  Gly  Val  Pro  Gly  Val  Gly  Val  Pro  Gly  Ala  Gly  Ala  Gly  Ser  Gly
              85                        90                       95

Ala  Gly  Ala  Gly  Ser  Gly  Ala  Gly  Ala  Gly  Ser  Gly  Ala  Gly  Ala  Gly
             100                       105                      110

Ser  Gly  Ala  Gly  Ala  Gly  Ser  Gly  Ala  Gly  Ala  Gly  Ser  Gly  Ala  Ala
             115                       120                      125

Gly  Tyr  Gly  Ala  Gly  Ala  Gly  Ser  Gly  Ala  Gly  Ala  Gly  Ser  Gly  Ala
             130                       135                      140

Gly  Ala  Gly  Ser  Gly  Ala  Gly  Ala  Gly  Ser  Gly  Ala  Gly  Ala  Gly  Ser
145                       150                      155                      160

Gly  Val  Gly  Val  Pro  Gly  Val  Gly  Val  Pro  Gly  Val  Gly  Val  Pro  Gly
             165                       170                      175

Val  Gly  Val  Pro  Gly  Val  Gly  Val  Pro  Gly  Val  Gly  Val  Pro  Gly  Val
             180                       185                      190

Gly  Val  Pro  Gly  Val  Gly  Val  Pro  Gly  Ala  Gly  Ala  Gly  Ser  Gly  Ala
             195                       200                      205

Gly  Ala  Gly  Ser  Gly  Ala  Gly  Ala  Gly  Ser  Gly  Ala  Gly  Ala  Gly  Ser
             210                       215                      220

Gly  Ala  Gly  Ala  Gly  Ser  Gly  Ala  Gly  Ala  Gly  Ser  Gly  Ala  Ala  Gly
225                       230                      235                      240

Tyr  Gly  Ala  Gly  Ala  Gly  Ser  Gly  Ala  Gly  Ala  Gly  Ser  Gly  Ala  Gly
             245                       250                      255

Ala  Gly  Ser  Gly  Ala  Gly  Ala  Gly  Ser  Gly  Ala  Gly  Ala  Gly  Ser  Gly
             260                       265                      270

Val  Gly  Val  Pro  Gly  Val  Gly  Val  Pro  Gly  Val  Gly  Val  Pro  Gly  Val
             275                       280                      285

Gly  Val  Pro  Gly  Val  Gly  Val  Pro  Gly  Val  Gly  Val  Pro  Gly  Val  Gly
             290                       295                      300

Val  Pro  Gly  Val  Gly  Val  Pro  Gly  Ala  Gly  Ala  Gly  Ser  Gly  Ala  Gly
305                       310                      315                      320

Ala  Gly  Ser  Gly  Ala  Gly  Ala  Gly  Ser  Gly  Ala  Gly  Ala  Gly  Ser  Gly
             325                       330                      335

Ala  Gly  Ala  Gly  Ser  Gly  Ala  Gly  Ala  Gly  Ser  Gly  Ala  Ala  Gly  Tyr
             340                       345                      350
```

```
Gly Ala Gly Ala Gly Ser Gly Ala Gly Ala Gly Ser Gly Ala Gly Ala
        355                 360                 365
Gly Ser Gly Ala Gly Ala Gly Ser Gly Ala Gly Ala Gly Ser Gly Val
        370                 375                 380
Gly Val Pro Gly Val Gly Val Pro Gly Val Gly Val Pro Gly Val Gly
385                     390                 395                 400
Val Pro Gly Val Gly Val Pro Gly Val Gly Val Pro Gly Val Gly Val
                405                 410                 415
Pro Gly Val Gly Val Pro Gly Ala Gly Ala Gly Ser Gly Ala Gly Ala
            420                 425                 430
Gly Ser Gly Ala Gly Ala Gly Ser Gly Ala Gly Ala Gly Ser Gly Ala
        435                 440                 445
Gly Ala Gly Ser Gly Ala Gly Ala Gly Ser Gly Ala Ala Gly Tyr Gly
        450                 455                 460
Ala Gly Ala Gly Ser Gly Ala Gly Ala Gly Ser Gly Ala Gly Ala Gly
465                     470                 475                 480
Ser Gly Ala Gly Ala Gly Ser Gly Ala Gly Ala Gly Ser Gly Val Gly
                485                 490                 495
Val Pro Gly Val Gly Val Pro Gly Val Gly Val Pro Gly Val Gly Val
            500                 505                 510
Pro Gly Val Gly Val Pro Gly Val Gly Val Pro Gly Val Gly Val Pro
        515                 520                 525
Gly Val Gly Val Pro Gly Ala Gly Ala Gly Ser Gly Ala Gly Ala Gly
530                     535                 540
Ser Gly Ala Gly Ala Gly Ser Gly Ala Gly Ala Gly Ser Gly Ala Gly
545                     550                 555                 560
Ala Gly Ser Gly Ala Gly Ala Gly Ser Gly Ala Ala Gly Tyr Gly Ala
                565                 570                 575
Gly Ala Gly Ser Gly Ala Gly Ala Gly Ser Gly Ala Gly Ala Gly Ser
            580                 585                 590
Gly Ala Gly Ala Gly Ser Gly Ala Gly Ala Gly Ser Gly Val Gly Val
        595                 600                 605
Pro Gly Val Gly Val Pro Gly Val Gly Val Pro Gly Val Gly Val Pro
    610                 615                 620
Gly Val Gly Val Pro Gly Val Gly Val Pro Gly Val Gly Val Pro Gly
625                 630                 635                 640
Val Gly Val Pro Gly Ala Gly Ala Gly Ser Gly Ala Gly Ala Gly Ser
                645                 650                 655
Gly Ala Gly Ala Gly Ser Gly Ala Gly Ala Gly Ser Gly Ala Gly Ala
            660                 665                 670
Gly Ser Gly Ala Gly Ala Gly Ser Gly Ala Ala Gly Tyr Gly Ala Gly
        675                 680                 685
Ala Gly Ser Gly Ala Gly Ala Gly Ser Gly Ala Gly Ala Gly Ser Gly
        690                 695                 700
Ala Gly Ala Gly Ser Gly Ala Gly Ala Gly Ser Gly Val Gly Val Pro
705                     710                 715                 720
Gly Val Gly Val Pro Gly Val Gly Val Pro Gly Val Gly Val Pro Gly
                725                 730                 735
Val Gly Val Pro Gly Val Gly Val Pro Gly Val Gly Val Pro Gly Val
            740                 745                 750
Gly Val Pro Gly Ala Gly Ala Gly Ser Gly Ala Gly Ala Gly Ser Gly
        755                 760                 765
Ala Gly Ala Gly Ser Gly Ala Gly Ala Gly Ser Gly Ala Gly Ala Gly
        770                 775                 780
```

```
Ser Gly Ala Gly Ala Gly Ser Gly Ala Ala Gly Tyr Gly Ala Gly Ala
785                 790                 795                 800
Gly Ser Gly Ala Gly Ala Gly Ser Gly Ala Gly Ala Gly Ser Gly Ala
                805                 810                 815
Gly Ala Gly Ser Gly Ala Gly Ala Gly Ser Gly Val Gly Val Pro Gly
                820                 825                 830
Val Gly Val Pro Gly Val Gly Val Pro Gly Val Gly Val Pro Gly Val
                835                 840                 845
Gly Val Pro Gly Val Gly Val Pro Gly Val Gly Val Pro Gly Val Gly
            850                 855                 860
Val Pro Gly Ala Gly Ala Gly Ser Gly Ala Gly Ala Gly Ser Gly Ala
865                 870                 875                 880
Gly Ala Gly Ser Gly Ala Gly Ala Gly Ser Gly Ala Gly Ala Gly Ser
                885                 890                 895
Gly Ala Gly Ala Gly Ser Gly Ala Ala Gly Tyr Gly Ala Gly Ala Gly
                900                 905                 910
Ser Gly Ala Gly Ala Gly Ser Gly Ala Gly Ala Gly Ser Gly Ala Gly
            915                 920                 925
Ala Gly Ser Gly Ala Gly Ala Gly Ser Gly Val Gly Val Pro Gly Val
            930                 935                 940
Gly Val Pro Gly Val Gly Val Pro Gly Val Gly Val Pro Gly Val Gly
945                 950                 955                 960
Val Pro Gly Val Gly Val Pro Gly Val Gly Val Pro Gly Val Gly Val
                965                 970                 975
Pro Gly Ala Gly Ala Gly Ser Gly Ala Gly Ala Gly Ser Gly Ala Gly
            980                 985                 990
Ala Gly Ser Gly Ala Gly Ala Gly Ser Gly Ala Gly Ala Gly Ser Gly
            995                 1000                1005
Ala Gly Ala Gly Ser Gly Ala Ala Gly Tyr Gly Ala Gly Ala Gly Ser
            1010                1015                1020
Gly Ala Gly Ala Gly Ser Gly Ala Gly Ala Gly Ser Gly Ala Gly Ala
1025                1030                1035                1040
Gly Ser Gly Ala Gly Ala Gly Ser Gly Val Gly Val Pro Gly Val Gly
                1045                1050                1055
Val Pro Gly Val Gly Val Pro Gly Val Gly Val Pro Gly Val Gly Val
                1060                1065                1070
Pro Gly Val Gly Val Pro Gly Val Gly Val Pro Gly Val Gly Val Pro
            1075                1080                1085
Gly Ala Gly Ala Gly Ser Gly Ala Gly Ala Gly Ser Gly Ala Gly Ala
            1090                1095                1100
Gly Ser Gly Ala Gly Ala Gly Ser Gly Ala Gly Ala Gly Ser Gly Ala
1105                1110                1115                1120
Gly Ala Gly Ser Gly Ala Ala Gly Tyr Gly Ala Gly Ala Gly Ser Gly
                1125                1130                1135
Ala Gly Ala Gly Ser Gly Ala Gly Ala Gly Ser Gly Ala Gly Ala Gly
                1140                1145                1150
Ser Gly Ala Gly Ala Gly Ser Gly Val Gly Val Pro Gly Val Gly Val
                1155                1160                1165
Pro Gly Val Gly Val Pro Gly Val Gly Val Pro Gly Val Gly Val Pro
            1170                1175                1180
Gly Val Gly Val Pro Gly Val Gly Val Pro Gly Val Gly Val Pro Gly
1185                1190                1195                1200
Ala Gly Ala Gly Ser Gly Ala Gly Ala Gly Ser Gly Ala Gly Ala Gly
```

|      | 1205 |      |      |      | 1210 |      |      |      | 1215 |      |      |      |      |
|------|------|------|------|------|------|------|------|------|------|------|------|------|------|

```
            1205                       1210                       1215
Ser Gly Ala Gly Ala Gly Ser Gly Ala Gly Ala Gly Ser Gly Ala Gly
                1220                       1225                       1230
Ala Gly Ser Gly Ala Ala Gly Tyr Gly Ala Gly Ala Gly Ser Gly Ala
                1235                       1240                       1245
Gly Ala Gly Ser Gly Ala Gly Ala Gly Ser Gly Ala Gly Ala Gly Ser
                1250                       1255                       1260
Gly Ala Gly Ala Gly Ser Gly Val Gly Val Pro Gly Val Gly Val Pro
1265                       1270                       1275                       1280
Gly Val Gly Val Pro Gly Val Gly Val Pro Gly Val Gly Val Pro Gly
                1285                       1290                       1295
Val Gly Val Pro Gly Val Gly Val Pro Gly Val Gly Val Pro Gly Ala
                1300                       1305                       1310
Gly Ala Gly Ser Gly Ala Gly Ala Gly Ser Gly Ala Gly Ala Gly Ser
                1315                       1320                       1325
Gly Ala Gly Ala Gly Ser Gly Ala Gly Ala Gly Ser Gly Ala Gly Ala
                1330                       1335                       1340
Gly Ser Gly Ala Ala Gly Tyr Gly Ala Gly Ala Gly Ser Gly Ala Gly
1345                       1350                       1355                       1360
Ala Gly Ser Gly Ala Gly Ala Gly Ser Gly Ala Gly Ala Gly Ser Gly
                1365                       1370                       1375
Ala Gly Ala Gly Ser Gly Val Gly Val Pro Gly Val Gly Val Pro Gly
                1380                       1385                       1390
Val Gly Val Pro Gly Val Gly Val Pro Gly Val Gly Val Pro Gly Val
                1395                       1400                       1405
Gly Val Pro Gly Val Gly Val Pro Gly Val Gly Val Pro Gly Ala Gly
                1410                       1415                       1420
Ala Gly Ser Gly Ala Gly Ala Gly Ser Gly Ala Gly Ala Gly Ser Gly
1425                       1430                       1435                       1440
Ala Gly Ala Gly Ser Gly Ala Gly Ala Gly Ser Gly Ala Gly Ala Gly
                1445                       1450                       1455
Ser Gly Ala Ala Gly Tyr Gly Ala Gly Ala Gly Ser Gly Ala Gly Ala
                1460                       1465                       1470
Gly Ser Gly Ala Gly Ala Gly Ser Gly Ala Gly Ala Gly Ser Gly Ala
                1475                       1480                       1485
Gly Ala Gly Ser Gly Val Gly Val Pro Gly Val Gly Val Pro Gly Val
                1490                       1495                       1500
Gly Val Pro Gly Val Gly Val Pro Gly Val Gly Val Pro Gly Val Gly
1505                       1510                       1515                       1520
Val Pro Gly Val Gly Val Pro Gly Val Gly Val Pro Gly Ala Gly Ala
                1525                       1530                       1535
Gly Ser Gly Ala Gly Ala Gly Ser Gly Ala Gly Ala Gly Ser Gly Ala
                1540                       1545                       1550
Gly Ala Gly Ser Gly Ala Gly Ala Gly Ser Gly Ala Gly Ala Gly Ser
                1555                       1560                       1565
Gly Ala Ala Gly Tyr Gly Ala Gly Ala Gly Ser Gly Ala Gly Ala Gly
                1570                       1575                       1580
Ser Gly Ala Gly Ala Gly Ser Gly Ala Gly Ala Gly Ser Gly Ala Gly
1585                       1590                       1595                       1600
Ala Gly Ser Gly Val Gly Val Pro Gly Val Gly Val Pro Gly Val Gly
                1605                       1610                       1615
Val Pro Gly Val Gly Val Pro Gly Val Gly Val Pro Gly Val Gly Val
                1620                       1625                       1630
```

```
Pro Gly Val Gly Val Pro Gly Val Gly Val Pro Gly Ala Gly Ala Gly
        1635                1640                1645

Ser Gly Ala Gly Ala Gly Ser Gly Ala Gly Ala Gly Ser Gly Ala Gly
        1650                1655                1660

Ala Gly Ser Gly Ala Gly Ala Gly Ser Gly Ala Gly Ala Gly Ser Gly
1665                1670                1675                1680

Ala Ala Gly Tyr Gly Ala Gly Ala Gly Ser Gly Ala Gly Ala Gly Ser
            1685                1690                1695

Gly Ala Gly Ala Gly Ser Gly Ala Gly Ala Gly Ser Gly Ala Gly Ala
        1700                1705                1710

Gly Ser Gly Val Gly Val Pro Gly Val Gly Val Pro Gly Val Gly Val
        1715                1720                1725

Pro Gly Val Gly Val Pro Gly Val Gly Val Pro Gly Val Gly Val Pro
        1730                1735                1740

Gly Val Gly Val Pro Gly Val Gly Val Pro Gly Ala Gly Ala Gly Ser
1745                1750                1755                1760

Gly Ala Gly Ala Gly Ser Gly Ala Gly Ala Gly Ser Gly Ala Gly Ala
            1765                1770                1775

Gly Ser Gly Ala Gly Ala Gly Ser Gly Ala Gly Ala Gly Ser Gly Ala
            1780                1785                1790

Ala Gly Tyr Gly Ala Gly Ala Gly Ser Gly Ala Gly Ala Gly Ser Gly
        1795                1800                1805

Ala Gly Ala Gly Ser Gly Ala Gly Ala Gly Ser Gly Ala Gly Ala Gly
        1810                1815                1820

Ser Gly Val Gly Val Pro Gly Val Gly Val Pro Gly Val Gly Val Pro
1825                1830                1835                1840

Gly Val Gly Val Pro Gly Val Gly Val Pro Gly Val Gly Val Pro Gly
            1845                1850                1855

Val Gly Val Pro Gly Val Gly Val Pro Gly Ala Gly Ala Gly Ser Gly
            1860                1865                1870

Ala Gly Ala Gly Ser Gly Ala Gly Ala Gly Ser Gly Ala Gly Ala Gly
            1875                1880                1885

Ser Gly Ala Gly Ala Gly Ser Gly Ala Gly Ala Gly Ser Gly Ala Ala
        1890                1895                1900

Gly Tyr Gly Ala Gly Ala Gly Ser Gly Ala Gly Ala Gly Ser Gly Ala
1905                1910                1915                1920

Gly Ala Gly Ser Gly Ala Gly Ala Gly Ser Gly Ala Gly Ala Gly Ser
            1925                1930                1935

Gly Val Gly Val Pro Gly Val Gly Val Pro Gly Val Gly Val Pro Gly
            1940                1945                1950

Val Gly Val Pro Gly Val Gly Val Pro Gly Val Gly Val Pro Gly Val
        1955                1960                1965

Gly Val Pro Gly Val Gly Val Pro Gly Ala Gly Ala Gly Ser Gly Ala
        1970                1975                1980

Gly Ala Gly Ser Gly Ala Gly Ala Gly Ser Gly Ala Gly Ala Gly Ser
1985                1990                1995                2000

Gly Ala Gly Ala Gly Ser Gly Ala Gly Ala Gly Ser Gly Ala Ala Gly
                2005                2010                2015

Tyr Gly Ala Gly Ala Gly Ser Gly Ala Gly Ala Gly Ser Gly Ala Gly
            2020                2025                2030

Ala Met Asp Pro Gly Arg Tyr Gln Leu Ser Ala Gly Arg Tyr His Tyr
            2035                2040                2045

Gln Leu Val Trp Cys Gln Lys
        2050                2055
```

( 2 ) INFORMATION FOR SEQ ID NO:47:

( i ) SEQUENCE CHARACTERISTICS:
        ( A ) LENGTH: 2257 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:47:

```
Met Asp Pro Val Val Leu Gln Arg Arg Asp Trp Glu Asn Pro Gly Val
 1               5                  10                  15

Thr Gln Leu Asn Arg Leu Ala Ala His Pro Pro Phe Ala Ser Asp Pro
                20                  25                  30

Met Gly Ala Gly Ser Gly Ala Gly Ala Gly Ser Gly Ala Gly Ala Gly
                35                  40                  45

Ser Gly Val Gly Val Pro Gly Val Gly Val Pro Gly Val Gly Val Pro
                50                  55                  60

Gly Val Gly Val Pro Gly Val Gly Val Pro Gly Val Gly Val Pro Gly
 65                  70                  75                  80

Val Gly Val Pro Gly Val Gly Val Pro Gly Ala Gly Ala Gly Ser Gly
                    85                  90                  95

Ala Gly Ala Gly Ser Gly Ala Gly Ala Gly Ser Gly Ala Gly Ala Gly
                100                 105                 110

Ser Gly Ala Gly Ala Gly Ser Gly Ala Gly Ala Gly Ser Gly Ala Gly
                115                 120                 125

Ala Gly Ser Gly Ala Gly Ala Gly Ser Gly Val Gly Val Pro Gly Val
                130                 135                 140

Gly Val Pro Gly Val Gly Val Pro Gly Val Gly Val Pro Gly Val Gly
145                 150                 155                 160

Val Pro Gly Val Gly Val Pro Gly Val Gly Val Pro Gly Val Gly Val
                165                 170                 175

Pro Gly Ala Gly Ala Gly Ser Gly Ala Gly Ala Gly Ser Gly Ala Gly
                180                 185                 190

Ala Gly Ser Gly Ala Gly Ala Gly Ser Gly Ala Gly Ala Gly Ser Gly
                195                 200                 205

Ala Gly Ala Gly Ser Gly Ala Gly Ala Gly Ser Gly Ala Gly Ala Gly
                210                 215                 220

Ser Gly Val Gly Val Pro Gly Val Gly Val Pro Gly Val Gly Val Pro
225                 230                 235                 240

Gly Val Gly Val Pro Gly Val Gly Val Pro Gly Val Gly Val Pro Gly
                245                 250                 255

Val Gly Val Pro Gly Val Gly Val Pro Gly Ala Gly Ala Gly Ser Gly
                260                 265                 270

Ala Gly Ala Gly Ser Gly Ala Gly Ala Gly Ser Gly Ala Gly Ala Gly
                275                 280                 285

Ser Gly Ala Gly Ala Gly Ser Gly Ala Gly Ala Gly Ser Gly Ala Gly
                290                 295                 300

Ala Gly Ser Gly Ala Gly Ala Gly Ser Gly Val Gly Val Pro Gly Val
305                 310                 315                 320

Gly Val Pro Gly Val Gly Val Pro Gly Val Gly Val Pro Gly Val Gly
                325                 330                 335

Val Pro Gly Val Gly Val Pro Gly Val Gly Val Pro Gly Val Gly Val
                340                 345                 350
```

-continued

```
Pro Gly Ala Gly Ala Gly Ser Gly Ala Gly Ala Gly Ser Gly Ala Gly
        355                 360                 365
Ala Gly Ser Gly Ala Gly Ala Gly Ser Gly Ala Gly Ala Gly Ser Gly
        370                 375                 380
Ala Gly Ala Gly Ser Gly Ala Gly Ala Gly Ser Gly Ala Gly Ala Gly
385                 390                 395                 400
Ser Gly Val Gly Val Pro Gly Val Gly Val Pro Gly Val Gly Val Pro
                405                 410                 415
Gly Val Gly Val Pro Gly Val Gly Val Pro Gly Val Gly Val Pro Gly
            420                 425                 430
Val Gly Val Pro Gly Val Gly Val Pro Gly Ala Gly Ala Gly Ser Gly
        435                 440                 445
Ala Gly Ala Gly Ser Gly Ala Gly Ala Gly Ser Gly Ala Gly Ala Gly
        450                 455                 460
Ser Gly Ala Gly Ala Gly Ser Gly Ala Gly Ala Gly Ser Gly Ala Gly
465                 470                 475                 480
Ala Gly Ser Gly Ala Gly Ala Gly Ser Gly Val Gly Val Pro Gly Val
                485                 490                 495
Gly Val Pro Gly Val Gly Val Pro Gly Val Gly Val Pro Gly Val Gly
            500                 505                 510
Val Pro Gly Val Gly Val Pro Gly Val Gly Val Pro Gly Val Gly Val
        515                 520                 525
Pro Gly Ala Gly Ala Gly Ser Gly Ala Gly Ala Gly Ser Gly Ala Gly
        530                 535                 540
Ala Gly Ser Gly Ala Gly Ala Gly Ser Gly Ala Gly Ala Gly Ser Gly
545                 550                 555                 560
Ala Gly Ala Gly Ser Gly Ala Gly Ala Gly Ser Gly Ala Gly Ala Gly
                565                 570                 575
Ser Gly Val Gly Val Pro Gly Val Gly Val Pro Gly Val Gly Val Pro
            580                 585                 590
Gly Val Gly Val Pro Gly Val Gly Val Pro Gly Val Gly Val Pro Gly
        595                 600                 605
Val Gly Val Pro Gly Val Gly Val Pro Gly Ala Gly Ala Gly Ser Gly
        610                 615                 620
Ala Gly Ala Gly Ser Gly Ala Gly Ala Gly Ser Gly Ala Gly Ala Gly
625                 630                 635                 640
Ser Gly Ala Gly Ala Gly Ser Gly Ala Gly Ala Gly Ser Gly Ala Gly
                645                 650                 655
Ala Gly Ser Gly Ala Gly Ala Gly Ser Gly Val Gly Val Pro Gly Val
            660                 665                 670
Gly Val Pro Gly Val Gly Val Pro Gly Val Gly Val Pro Gly Val Gly
        675                 680                 685
Val Pro Gly Val Gly Val Pro Gly Val Gly Val Pro Gly Val Gly Val
        690                 695                 700
Pro Gly Ala Gly Ala Gly Ser Gly Ala Gly Ala Gly Ser Gly Ala Gly
705                 710                 715                 720
Ala Gly Ser Gly Ala Gly Ala Gly Ser Gly Ala Gly Ala Gly Ser Gly
                725                 730                 735
Ala Gly Ala Gly Ser Gly Ala Gly Ala Gly Ser Gly Ala Gly Ala Gly
            740                 745                 750
Ser Gly Val Gly Val Pro Gly Val Gly Val Pro Gly Val Gly Val Pro
        755                 760                 765
Gly Val Gly Val Pro Gly Val Gly Val Pro Gly Val Gly Val Pro Gly
        770                 775                 780
```

| Val<br>785 | Gly | Val | Pro | Gly<br>790 | Val | Gly | Val | Pro<br>795 | Gly | Ala | Gly | Ala | Gly | Ser | Gly<br>800 |
|---|---|---|---|---|---|---|---|---|---|---|---|---|---|---|---|
| Ala | Gly | Ala | Gly | Ser<br>805 | Gly | Ala | Gly | Ala<br>810 | Gly | Ser | Gly | Ala | Gly | Ala<br>815 | Gly |
| Ser | Gly | Ala | Gly<br>820 | Ala | Gly | Ser | Gly | Ala<br>825 | Gly | Ala | Gly | Ser | Gly<br>830 | Ala | Gly |
| Ala | Gly | Ser<br>835 | Gly | Ala | Gly | Ala | Gly<br>840 | Ser | Gly | Val | Gly | Val<br>845 | Pro | Gly | Val |
| Gly | Val | Pro<br>850 | Gly | Val | Gly | Val<br>855 | Pro | Gly | Val | Gly | Val<br>860 | Pro | Gly | Val | Gly |
| Val<br>865 | Pro | Gly | Val | Gly | Val<br>870 | Pro | Gly | Val | Gly | Val<br>875 | Pro | Gly | Val | Gly | Val<br>880 |
| Pro | Gly | Ala | Gly | Ala<br>885 | Gly | Ser | Gly | Ala | Gly<br>890 | Ala | Gly | Ser | Gly | Ala<br>895 | Gly |
| Ala | Gly | Ser | Gly<br>900 | Ala | Gly | Ala | Gly | Ser<br>905 | Gly | Ala | Gly | Ala | Gly<br>910 | Ser | Gly |
| Ala | Gly | Ala | Gly | Ser<br>915 | Gly | Ala | Gly | Ala<br>920 | Gly | Ser | Gly | Ala | Gly | Ala<br>925 | Gly |
| Ser | Gly<br>930 | Val | Gly | Val | Pro | Gly<br>935 | Val | Gly | Val | Pro | Gly<br>940 | Val | Gly | Val | Pro |
| Gly<br>945 | Val | Gly | Val | Pro | Gly<br>950 | Val | Gly | Val | Pro | Gly<br>955 | Val | Gly | Val | Pro | Gly<br>960 |
| Val | Gly | Val | Pro | Gly<br>965 | Val | Gly | Val | Pro | Gly<br>970 | Ala | Gly | Ala | Gly | Ser<br>975 | Gly |
| Ala | Gly | Ala | Gly<br>980 | Ser | Gly | Ala | Gly | Ala<br>985 | Gly | Ser | Gly | Ala | Gly<br>990 | Ala | Gly |
| Ser | Gly | Ala<br>995 | Gly | Ala | Gly | Ser | Gly<br>1000 | Ala | Gly | Ala | Gly | Ser<br>1005 | Gly | Ala | Gly |
| Ala | Gly | Ser<br>1010 | Gly | Ala | Gly | Ala | Gly<br>1015 | Ser | Gly | Val | Gly | Val<br>1020 | Pro | Gly | Val |
| Gly<br>1025 | Val | Pro | Gly | Val | Gly<br>1030 | Val | Pro | Gly | Val | Gly<br>1035 | Val | Pro | Gly | Val | Gly<br>1040 |
| Val | Pro | Gly | Val | Gly<br>1045 | Val | Pro | Gly | Val | Gly<br>1050 | Val | Pro | Gly | Val | Gly<br>1055 | Val |
| Pro | Gly | Ala | Gly | Ala<br>1060 | Gly | Ser | Gly | Ala | Gly<br>1065 | Ala | Gly | Ser | Gly | Ala<br>1070 | Gly |
| Ala | Gly | Ser<br>1075 | Gly | Ala | Gly | Ala | Gly<br>1080 | Ser | Gly | Ala | Gly | Ala<br>1085 | Gly | Ser | Gly |
| Ala | Gly | Ala | Gly<br>1090 | Ser | Gly | Ala | Gly | Ala<br>1095 | Gly | Ser | Gly | Ala | Gly<br>1100 | Ala | Gly |
| Ser | Gly<br>1105 | Val | Gly | Val | Pro | Gly<br>1110 | Val | Gly | Val | Pro<br>1115 | Gly | Val | Gly | Val | Pro<br>1120 |
| Gly | Val | Gly | Val | Pro | Gly<br>1125 | Val | Gly | Val | Pro<br>1130 | Gly | Val | Gly | Val | Pro<br>1135 | Gly |
| Val | Gly | Val | Pro<br>1140 | Gly | Val | Gly | Val | Pro<br>1145 | Gly | Ala | Gly | Ala | Gly | Ser<br>1150 | Gly |
| Ala | Gly | Ala | Gly<br>1155 | Ser | Gly | Ala | Gly | Ala<br>1160 | Gly | Ser | Gly | Ala | Gly | Ala<br>1165 | Gly |
| Ser | Gly | Ala<br>1170 | Gly | Ala | Gly | Ser | Gly<br>1175 | Ala | Gly | Ala | Gly | Ser<br>1180 | Gly | Ala | Gly |
| Ala | Gly | Ser<br>1185 | Gly | Ala | Gly | Ala | Gly<br>1190 | Ser | Gly | Val | Gly | Val<br>1195 | Pro | Gly | Val<br>1200 |
| Gly | Val | Pro | Gly | Val | Gly | Val | Pro | Gly | Val | Gly | Val | Pro | Gly | Val | Gly |

```
                         1205                    1210                     1215
Val  Pro  Gly  Val  Gly  Val  Pro  Gly  Val  Gly  Val  Pro  Gly  Val  Gly  Val
                    1220                    1225                    1230
Pro  Gly  Ala  Gly  Ala  Gly  Ser  Gly  Ala  Gly  Ala  Gly  Ser  Gly  Ala  Gly
                    1235                    1240                    1245
Ala  Gly  Ser  Gly  Ala  Gly  Ala  Gly  Ser  Gly  Ala  Gly  Ala  Gly  Ser  Gly
                    1250                    1255                    1260
Ala  Gly  Ala  Gly  Ser  Gly  Ala  Gly  Ala  Gly  Ser  Gly  Ala  Gly  Ala  Gly
1265                     1270                    1275                    1280
Ser  Gly  Val  Gly  Val  Pro  Gly  Val  Gly  Val  Pro  Gly  Val  Gly  Val  Pro
                    1285                    1290                    1295
Gly  Val  Gly  Val  Pro  Gly  Val  Gly  Val  Pro  Gly  Val  Gly  Val  Pro  Gly
                    1300                    1305                    1310
Val  Gly  Val  Pro  Gly  Val  Gly  Val  Pro  Gly  Ala  Gly  Ala  Gly  Ser  Gly
                    1315                    1320                    1325
Ala  Gly  Ala  Gly  Ser  Gly  Ala  Gly  Ala  Gly  Ser  Gly  Ala  Gly  Ala  Gly
                    1330                    1335                    1340
Ser  Gly  Ala  Gly  Ala  Gly  Ser  Gly  Ala  Gly  Ala  Gly  Ser  Gly  Ala  Gly
1345                     1350                    1355                    1360
Ala  Gly  Ser  Gly  Ala  Gly  Ala  Gly  Ser  Gly  Val  Gly  Val  Pro  Gly  Val
                    1365                    1370                    1375
Gly  Val  Pro  Gly  Val  Gly  Val  Pro  Gly  Val  Gly  Val  Pro  Gly  Val  Gly
                    1380                    1385                    1390
Val  Pro  Gly  Val  Gly  Val  Pro  Gly  Val  Gly  Val  Pro  Gly  Val  Gly  Val
                    1395                    1400                    1405
Pro  Gly  Ala  Gly  Ala  Gly  Ser  Gly  Ala  Gly  Ala  Gly  Ser  Gly  Ala  Gly
                    1410                    1415                    1420
Ala  Gly  Ser  Gly  Ala  Gly  Ala  Gly  Ser  Gly  Ala  Gly  Ala  Gly  Ser  Gly
1425                     1430                    1435                    1440
Ala  Gly  Ala  Gly  Ser  Gly  Ala  Gly  Ala  Gly  Ser  Gly  Ala  Gly  Ala  Gly
                    1445                    1450                    1455
Ser  Gly  Val  Gly  Val  Pro  Gly  Val  Gly  Val  Pro  Gly  Val  Gly  Val  Pro
                    1460                    1465                    1470
Gly  Val  Gly  Val  Pro  Gly  Val  Gly  Val  Pro  Gly  Val  Gly  Val  Pro  Gly
                    1475                    1480                    1485
Val  Gly  Val  Pro  Gly  Val  Gly  Val  Pro  Gly  Ala  Gly  Ala  Gly  Ser  Gly
                    1490                    1495                    1500
Ala  Gly  Ala  Gly  Ser  Gly  Ala  Gly  Ala  Gly  Ser  Gly  Ala  Gly  Ala  Gly
1505                     1510                    1515                    1520
Ser  Gly  Ala  Gly  Ala  Gly  Ser  Gly  Ala  Gly  Ala  Gly  Ser  Gly  Ala  Gly
                    1525                    1530                    1535
Ala  Gly  Ser  Gly  Ala  Gly  Ala  Gly  Ser  Gly  Val  Gly  Val  Pro  Gly  Val
                    1540                    1545                    1550
Gly  Val  Pro  Gly  Val  Gly  Val  Pro  Gly  Val  Gly  Val  Pro  Gly  Val  Gly
                    1555                    1560                    1565
Val  Pro  Gly  Val  Gly  Val  Pro  Gly  Val  Gly  Val  Pro  Gly  Val  Gly  Val
                    1570                    1575                    1580
Pro  Gly  Ala  Gly  Ala  Gly  Ser  Gly  Ala  Gly  Ala  Gly  Ser  Gly  Ala  Gly
                    1585                    1590                    1595                    1600
Ala  Gly  Ser  Gly  Ala  Gly  Ala  Gly  Ser  Gly  Ala  Gly  Ala  Gly  Ser  Gly
                    1605                    1610                    1615
Ala  Gly  Ala  Gly  Ser  Gly  Ala  Gly  Ala  Gly  Ser  Gly  Ala  Gly  Ala  Gly
                    1620                    1625                    1630
```

-continued

```
Ser Gly Val Gly Val Pro Gly Val Gly Val Pro Gly Val Gly Val Pro
        1635                1640                1645
Gly Val Gly Val Pro Gly Val Gly Val Pro Gly Val Gly Val Pro Gly
    1650                1655                1660
Val Gly Val Pro Gly Val Gly Val Pro Gly Ala Gly Ala Gly Ser Gly
1665                1670                1675                1680
Ala Gly Ala Gly Ser Gly Ala Gly Ala Gly Ser Gly Ala Gly Ala Gly
            1685                1690                1695
Ser Gly Ala Gly Ala Gly Ser Gly Ala Gly Ala Gly Ser Gly Ala Gly
        1700                1705                1710
Ala Gly Ser Gly Ala Gly Ala Gly Ser Gly Val Gly Val Pro Gly Val
            1715                1720                1725
Gly Val Pro Gly Val Gly Val Pro Gly Val Gly Val Pro Gly Val Gly
        1730                1735                1740
Val Pro Gly Val Gly Val Pro Gly Val Gly Val Pro Gly Val Gly Val
1745                1750                1755                1760
Pro Gly Ala Gly Ala Gly Ser Gly Ala Gly Ala Gly Ser Gly Ala Gly
            1765                1770                1775
Ala Gly Ser Gly Ala Gly Ala Gly Ser Gly Ala Gly Ala Gly Ser Gly
            1780                1785                1790
Ala Gly Ala Gly Ser Gly Ala Gly Ala Gly Ser Gly Ala Gly Ala Gly
            1795                1800                1805
Ser Gly Val Gly Val Pro Gly Val Gly Val Pro Gly Val Gly Val Pro
        1810                1815                1820
Gly Val Gly Val Pro Gly Val Gly Val Pro Gly Val Gly Val Pro Gly
1825                1830                1835                1840
Val Gly Val Pro Gly Val Gly Val Pro Gly Ala Gly Ala Gly Ser Gly
            1845                1850                1855
Ala Gly Ala Gly Ser Gly Ala Gly Ala Gly Ser Gly Ala Gly Ala Gly
            1860                1865                1870
Ser Gly Ala Gly Ala Gly Ser Gly Ala Gly Ala Gly Ser Gly Ala Gly
        1875                1880                1885
Ala Gly Ser Gly Ala Gly Ala Gly Ser Gly Val Gly Val Pro Gly Val
            1890                1895                1900
Gly Val Pro Gly Val Gly Val Pro Gly Val Gly Val Pro Gly Val Gly
1905                1910                1915                1920
Val Pro Gly Val Gly Val Pro Gly Val Gly Val Pro Gly Val Gly Val
            1925                1930                1935
Pro Gly Ala Gly Ala Gly Ser Gly Ala Gly Ala Gly Ser Gly Ala Gly
            1940                1945                1950
Ala Gly Ser Gly Ala Gly Ala Gly Ser Gly Ala Gly Ala Gly Ser Gly
            1955                1960                1965
Ala Gly Ala Gly Ser Gly Ala Gly Ala Gly Ser Gly Ala Gly Ala Gly
            1970                1975                1980
Ser Gly Val Gly Val Pro Gly Val Gly Val Pro Gly Val Gly Val Pro
1985                1990                1995                2000
Gly Val Gly Val Pro Gly Val Gly Val Pro Gly Val Gly Val Pro Gly
            2005                2010                2015
Val Gly Val Pro Gly Val Gly Val Pro Gly Ala Gly Ala Gly Ser Gly
            2020                2025                2030
Ala Gly Ala Gly Ser Gly Ala Gly Ala Gly Ser Gly Ala Gly Ala Gly
            2035                2040                2045
Ser Gly Ala Gly Ala Gly Ser Gly Ala Gly Ala Gly Ser Gly Ala Gly
        2050                2055                2060
```

5,641,648

121

122

-continued

| | | | | | | | | | | | | | | | |
|---|---|---|---|---|---|---|---|---|---|---|---|---|---|---|---|
| Ala | Gly | Ser | Gly | Ala | Gly | Ala | Gly | Ser | Gly | Val | Gly | Val | Pro | Gly | Val |
| 2065 | | | | 2070 | | | | 2075 | | | | | | | 2080 |
| Gly | Val | Pro | Gly | Val | Gly | Val | Pro | Gly | Val | Gly | Val | Pro | Gly | Val | Gly |
| | | | | 2085 | | | | 2090 | | | | | | 2095 | |
| Val | Pro | Gly | Val | Gly | Val | Pro | Gly | Val | Gly | Val | Pro | Gly | Val | Gly | Val |
| | | | | 2100 | | | | 2105 | | | | 2110 | | | |
| Pro | Gly | Ala | Gly | Ala | Gly | Ser | Gly | Ala | Gly | Ala | Gly | Ser | Gly | Ala | Gly |
| | | 2115 | | | | | | 2120 | | | | 2125 | | | |
| Ala | Gly | Ser | Gly | Ala | Gly | Ala | Gly | Ser | Gly | Ala | Gly | Ala | Gly | Ser | Gly |
| | | 2130 | | | | 2135 | | | | | | 2140 | | | |
| Ala | Gly | Ala | Gly | Ser | Gly | Ala | Gly | Ala | Gly | Ser | Gly | Ala | Gly | Ala | Gly |
| 2145 | | | | 2150 | | | | | | 2155 | | | | | 2160 |
| Ser | Gly | Val | Gly | Val | Pro | Gly | Val | Gly | Val | Pro | Gly | Val | Gly | Val | Pro |
| | | | | 2165 | | | | 2170 | | | | | | 2175 | |
| Gly | Val | Gly | Val | Pro | Gly | Val | Gly | Val | Pro | Gly | Val | Gly | Val | Pro | Gly |
| | | | | 2180 | | | | 2185 | | | | | | 2190 | |
| Val | Gly | Val | Pro | Gly | Val | Gly | Val | Pro | Gly | Ala | Gly | Ala | Gly | Ser | Gly |
| | | 2195 | | | | | | 2200 | | | | 2205 | | | |
| Ala | Gly | Ala | Gly | Ser | Gly | Ala | Gly | Ala | Gly | Ser | Gly | Ala | Gly | Ala | Gly |
| | | 2210 | | | | | | 2215 | | | | 2220 | | | |
| Ser | Gly | Ala | Gly | Ala | Gly | Ser | Gly | Ala | Gly | Ala | Met | Asp | Pro | Gly | Arg |
| 2225 | | | | 2230 | | | | | | 2235 | | | | | 2240 |
| Tyr | Gln | Leu | Ser | Ala | Gly | Arg | Tyr | His | Tyr | Gln | Leu | Val | Trp | Cys | Gln |
| | | | | 2245 | | | | 2250 | | | | | | 2255 | |
| Lys | | | | | | | | | | | | | | | |

( 2 ) INFORMATION FOR SEQ ID NO:48:

( i ) SEQUENCE CHARACTERISTICS:
  ( A ) LENGTH: 1059 amino acids
  ( B ) TYPE: amino acid
  ( C ) STRANDEDNESS: single
  ( D ) TOPOLOGY: linear ( i i ) MOLECULE TYPE: peptide ( x i ) SEQUENCE DESCRIPTION: SEQ ID NO:48:

| | | | | | | | | | | | | | | | |
|---|---|---|---|---|---|---|---|---|---|---|---|---|---|---|---|
| Met | Asp | Pro | Val | Val | Leu | Gln | Arg | Arg | Asp | Trp | Glu | Asn | Pro | Gly | Val |
| 1 | | | | 5 | | | | | 10 | | | | | 15 | |
| Thr | Gln | Leu | Asn | Arg | Leu | Ala | Ala | His | Pro | Pro | Phe | Ala | Ser | Asp | Pro |
| | | | 20 | | | | | 25 | | | | | 30 | | |
| Met | Gly | Ala | Gly | Ser | Gly | Ala | Gly | Ala | Gly | Ser | Gly | Ala | Gly | Ala | Gly |
| | | 35 | | | | | | 40 | | | | 45 | | | |
| Ser | Gly | Ala | Gly | Ala | Gly | Ser | Gly | Ala | Gly | Ala | Gly | Ser | Gly | Ala | Gly |
| | 50 | | | | | 55 | | | | | | 60 | | | |
| Ala | Gly | Ser | Gly | Ala | Gly | Ala | Gly | Ser | Gly | Ala | Gly | Ala | Gly | Ser | Gly |
| 65 | | | | | | 70 | | | | | | 75 | | | 80 |
| Ala | Gly | Ala | Gly | Ser | Gly | Ala | Gly | Ala | Gly | Ser | Gly | Ala | Gly | Ala | Gly |
| | | | | 85 | | | | | | 90 | | | | | 95 |
| Ser | Gly | Ala | Gly | Ala | Gly | Ser | Gly | Ala | Gly | Ala | Gly | Ser | Gly | Ala | Gly |
| | | | | 100 | | | | 105 | | | | 110 | | | |
| Ala | Gly | Ser | Gly | Ala | Gly | Ala | Gly | Ser | Gly | Ala | Gly | Ala | Gly | Ser | Gly |
| | | | | 115 | | | | 120 | | | | 125 | | | |
| Ala | Gly | Ala | Gly | Ser | Gly | Ala | Gly | Ala | Gly | Ser | Gly | Ala | Gly | Ala | Gly |
| | | 130 | | | | | | 135 | | | | | | 140 | |
| Ser | Gly | Ala | Gly | Ala | Gly | Ser | Gly | Ala | Gly | Ala | Gly | Ser | Gly | Ala | Gly |

|  |  |  |  | 145 |  |  |  | 150 |  |  |  | 155 |  |  |  | 160 |
|---|---|---|---|---|---|---|---|---|---|---|---|---|---|---|---|---|---|

```
                      145                     150                     155                     160
Ala   Gly   Ser   Gly   Ala   Gly   Ser   Gly   Ala   Gly   Ala   Gly   Ser   Gly
                              165                     170                     175
Ala   Gly   Ala   Gly   Ser   Gly   Ala   Gly   Ala   Gly   Ser   Gly   Ala   Gly
                              180                     185                     190
Ser   Gly   Ala   Gly   Ala   Gly   Ser   Gly   Ala   Gly   Ala   Gly   Ser   Gly   Ala   Gly
                              195                     200                     205
Ala   Gly   Ser   Gly   Ala   Gly   Ala   Gly   Ser   Gly   Ala   Gly   Ala   Gly   Ser   Gly
      210                           215                           220
Ala   Gly   Ala   Gly   Ser   Gly   Ala   Gly   Ala   Gly   Ser   Gly   Ala   Gly   Ala   Gly
225                                 230                           235                           240
Ser   Gly   Ala   Gly   Ala   Gly   Ser   Gly   Ala   Gly   Ala   Gly   Ser   Gly   Ala   Gly
                              245                           250                           255
Ala   Gly   Ser   Gly   Ala   Gly   Ala   Gly   Ser   Gly   Ala   Gly   Ala   Gly   Ser   Gly
                              260                           265                           270
Ala   Gly   Ala   Gly   Ser   Gly   Ala   Gly   Ala   Gly   Ser   Gly   Ala   Gly   Ala   Gly
                              275                           280                           285
Ser   Gly   Ala   Gly   Ala   Gly   Ser   Gly   Ala   Gly   Ala   Gly   Ser   Gly   Ala   Gly
                              290                           295                           300
Ala   Gly   Ser   Gly   Ala   Gly   Ala   Gly   Ser   Gly   Ala   Gly   Ala   Gly   Ser   Gly
305                                 310                           315                           320
Ala   Gly   Ala   Gly   Ser   Gly   Ala   Gly   Ala   Gly   Ser   Gly   Ala   Gly   Ala   Gly
                              325                           330                           335
Ser   Gly   Ala   Gly   Ala   Gly   Ser   Gly   Ala   Gly   Ala   Gly   Ser   Gly   Ala   Gly
                              340                           345                           350
Ala   Gly   Ser   Gly   Ala   Gly   Ala   Gly   Ser   Gly   Ala   Gly   Ala   Gly   Ser   Gly
                              355                           360                           365
Ala   Gly   Ala   Gly   Ser   Gly   Ala   Gly   Ala   Gly   Ser   Gly   Ala   Gly   Ala   Gly
                              370                           375                           380
Ser   Gly   Ala   Gly   Ala   Gly   Ser   Gly   Ala   Gly   Ala   Gly   Ser   Gly   Ala   Gly
385                                 390                           395                           400
Ala   Gly   Ser   Gly   Ala   Gly   Ala   Gly   Ser   Gly   Ala   Gly   Ala   Gly   Ser   Gly
                              405                           410                           415
Ala   Gly   Ala   Gly   Ser   Gly   Ala   Gly   Ala   Gly   Ser   Gly   Ala   Gly   Ala   Gly
                              420                           425                           430
Ser   Gly   Ala   Gly   Ala   Gly   Ser   Gly   Ala   Gly   Ala   Gly   Ser   Gly   Ala   Gly
                              435                           440                           445
Ala   Gly   Ser   Gly   Ala   Gly   Ala   Gly   Ser   Gly   Ala   Gly   Ala   Gly   Ser   Gly
                              450                           455                           460
Ala   Gly   Ala   Gly   Ser   Gly   Ala   Gly   Ala   Gly   Ser   Gly   Ala   Gly   Ala   Gly
465                                 470                           475                           480
Ser   Gly   Ala   Gly   Ala   Gly   Ser   Gly   Ala   Gly   Ala   Gly   Ser   Gly   Ala   Gly
                              485                           490                           495
Ala   Gly   Ser   Gly   Ala   Gly   Ala   Gly   Ser   Gly   Ala   Gly   Ala   Gly   Ser   Gly
                              500                           505                           510
Ala   Gly   Ala   Gly   Ser   Gly   Ala   Gly   Ala   Gly   Ser   Gly   Ala   Gly   Ala   Gly
                              515                           520                           525
Ser   Gly   Ala   Gly   Ala   Gly   Ser   Gly   Ala   Gly   Ala   Gly   Ser   Gly   Ala   Gly
                              530                           535                           540
Ala   Gly   Ser   Gly   Ala   Gly   Ala   Gly   Ser   Gly   Ala   Gly   Ala   Gly   Ser   Gly
545                                 550                           555                           560
Ala   Gly   Ala   Gly   Ser   Gly   Ala   Gly   Ala   Gly   Ser   Gly   Ala   Gly   Ala   Gly
                              565                           570                           575
```

-continued

```
Ser  Gly  Ala  Gly  Ala  Gly  Ser  Gly  Ala  Gly  Ala  Gly  Ser  Gly  Ala  Gly
               580                     585                     590
Ala  Gly  Ser  Gly  Ala  Gly  Ala  Gly  Ser  Gly  Ala  Gly  Ala  Gly  Ser  Gly
          595                     600                     605
Ala  Gly  Ala  Gly  Ser  Gly  Ala  Gly  Ala  Gly  Ser  Gly  Ala  Gly  Ala  Gly
          610                     615                     620
Ser  Gly  Ala  Gly  Ala  Gly  Ser  Gly  Ala  Gly  Ala  Gly  Ser  Gly  Ala  Gly
625                     630                     635                          640
Ala  Gly  Ser  Gly  Ala  Gly  Ala  Gly  Ser  Gly  Ala  Gly  Ala  Gly  Ser  Gly
               645                     650                     655
Ala  Gly  Ala  Gly  Ser  Gly  Ala  Gly  Ala  Gly  Ser  Gly  Ala  Gly  Ala  Gly
               660                     665                     670
Ser  Gly  Ala  Gly  Ala  Gly  Ser  Gly  Ala  Gly  Ala  Gly  Ser  Gly  Ala  Gly
          675                     680                     685
Ala  Gly  Ser  Gly  Ala  Gly  Ala  Gly  Ser  Gly  Ala  Gly  Ala  Gly  Ser  Gly
          690                     695                     700
Ala  Gly  Ala  Gly  Ser  Gly  Ala  Gly  Ala  Gly  Ser  Gly  Ala  Gly  Ala  Gly
705                     710                     715                          720
Ser  Gly  Ala  Gly  Ala  Gly  Ser  Gly  Ala  Gly  Ala  Gly  Ser  Gly  Ala  Gly
               725                     730                     735
Ala  Gly  Ser  Gly  Ala  Gly  Ala  Gly  Ser  Gly  Ala  Gly  Ala  Gly  Ser  Gly
               740                     745                     750
Ala  Gly  Ala  Gly  Ser  Gly  Ala  Gly  Ala  Gly  Ser  Gly  Ala  Gly  Ala  Gly
          755                     760                     765
Ser  Gly  Ala  Gly  Ala  Gly  Ser  Gly  Ala  Gly  Ala  Gly  Ser  Gly  Ala  Gly
          770                     775                     780
Ala  Gly  Ser  Gly  Ala  Gly  Ala  Gly  Ser  Gly  Ala  Gly  Ala  Gly  Ser  Gly
785                     790                     795                          800
Ala  Gly  Ala  Gly  Ser  Gly  Ala  Gly  Ala  Gly  Ser  Gly  Ala  Gly  Ala  Gly
               805                     810                     815
Ser  Gly  Ala  Gly  Ala  Gly  Ser  Gly  Ala  Gly  Ala  Gly  Ser  Gly  Ala  Gly
               820                     825                     830
Ala  Gly  Ser  Gly  Ala  Gly  Ala  Gly  Ser  Gly  Ala  Gly  Ala  Gly  Ser  Gly
          835                     840                     845
Ala  Gly  Ala  Gly  Ser  Gly  Ala  Gly  Ala  Gly  Ser  Gly  Ala  Gly  Ala  Gly
          850                     855                     860
Ser  Gly  Ala  Gly  Ala  Gly  Ser  Gly  Ala  Gly  Ala  Gly  Ser  Gly  Ala  Gly
865                     870                     875                          880
Ala  Gly  Ser  Gly  Ala  Gly  Ala  Gly  Ser  Gly  Ala  Gly  Ala  Gly  Ser  Gly
               885                     890                     895
Ala  Gly  Ala  Gly  Ser  Gly  Ala  Gly  Ala  Gly  Ser  Gly  Ala  Gly  Ala  Gly
               900                     905                     910
Ser  Gly  Ala  Gly  Ala  Gly  Ser  Gly  Ala  Gly  Ala  Gly  Ser  Gly  Ala  Gly
          915                     920                     925
Ala  Gly  Ser  Gly  Ala  Gly  Ala  Gly  Ser  Gly  Ala  Gly  Ala  Gly  Ser  Gly
          930                     935                     940
Ala  Gly  Ala  Gly  Ser  Gly  Ala  Gly  Ala  Gly  Ser  Gly  Ala  Gly  Ala  Gly
945                     950                     955                          960
Ser  Gly  Ala  Gly  Ala  Gly  Ser  Gly  Ala  Gly  Ala  Gly  Ser  Gly  Ala  Gly
               965                     970                     975
Ala  Gly  Ser  Gly  Ala  Gly  Ala  Gly  Ser  Gly  Ala  Gly  Ala  Gly  Ser  Gly
               980                     985                     990
Ala  Gly  Ala  Gly  Ser  Gly  Ala  Gly  Ala  Gly  Ser  Gly  Ala  Gly  Ala  Gly
          995                     1000                    1005
```

```
            Ser   Gly   Ala   Gly   Ala   Gly   Ser   Gly   Ala   Gly   Ala   Gly   Ser   Gly   Ala   Gly
                       1010                    1015                    1020

Ala   Gly   Ser   Gly   Ala   Gly   Ala   Gly   Ser   Gly   Ala   Gly   Ala   Met   Asp   Pro
                  1025                    1030                    1035                          1040

Gly   Arg   Tyr   Gln   Leu   Ser   Ala   Gly   Arg   Tyr   His   Tyr   Gln   Leu   Val   Trp
                                    1045                          1050                    1055

Cys   Gln   Lys
```

( 2 ) INFORMATION FOR SEQ ID NO:49:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:49:

```
GTGACTGGCC   GTGGTGATAG   CCCGGCTAGC   GCTGCA                                        36
```

( 2 ) INFORMATION FOR SEQ ID NO:50:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:50:

```
GCGCTAGCCG   GGCTATCACC   ACGGCCAGTC   ACTGCA                                        36
```

( 2 ) INFORMATION FOR SEQ ID NO:51:

( i ) SEQUENCE CHARACTERISTICS:
        ( A ) LENGTH: 219 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:51:

```
GGTGCCGGCA   GCGGTGCAGG   AGCCGGTTCT   GGAGCTGGCG   CGGGCTCTGG   CGCGGGCGCA           60
GGATCCGGCG   CAGGCGCTGG   TTCTGGCGCA   GGGGCAGGCT   CTGGCGCAGG   AGCGGGGTCT          120
GGAGCTGCAG   TGACTGGCCG   TGGTGATAGC   CCGGCTAGCG   CTGCAGGCTA   TGGAGCTGGC          180
GCTGGCTCAG   GTGCTGGAGC   AGGAAGCGGA   GCGGGTGCC                                    219
```

( 2 ) INFORMATION FOR SEQ ID NO:52:

( i ) SEQUENCE CHARACTERISTICS:
        ( A ) LENGTH: 72 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:52:

```
            Gly   Ala   Gly   Ser   Gly   Ala   Gly   Ala   Gly   Ser   Gly   Ala   Gly   Ala   Gly   Ser
            1                       5                       10                      15

Gly   Ala   Gly   Ala   Gly   Ser   Gly   Ala   Gly   Ala   Gly   Ser   Gly   Ala   Gly   Ala
```

20                        25                            30

Gly  Ser  Gly  Ala  Gly  Ala  Gly  Ser  Gly  Ala  Ala  Val  Thr  Gly  Arg  Gly
              35                       40                       45

Asp  Ser  Pro  Ala  Ser  Ala  Ala  Gly  Tyr  Gly  Ala  Gly  Ala  Gly  Ser  Gly
         50                       55                       60

Ala  Gly  Ala  Gly  Ser  Gly  Ala  Gly
    65                       70

( 2 ) INFORMATION FOR SEQ ID NO:53:

( i ) SEQUENCE CHARACTERISTICS:
            ( A ) LENGTH: 766 amino acids
            ( B ) TYPE: amino acid
            ( C ) STRANDEDNESS: single
            ( D ) TOPOLOGY: linear ( i i ) MOLECULE TYPE: peptide ( x i ) SEQUENCE DESCRIPTION: SEQ ID NO:53:

Asp  Pro  Val  Val  Leu  Gln  Arg  Arg  Asp  Trp  Glu  Asn  Pro  Gly  Val  Thr
    1                   5                        10                       15

Gln  Leu  Asn  Arg  Leu  Ala  Ala  His  Pro  Pro  Phe  Ala  Ser  Asp  Pro  Met
                   20                       25                       30

Gly  Ala  Gly  Ser  Gly  Ala  Gly  Ala  Gly  Ser  Gly  Ala  Gly  Ala  Gly  Ser
                   35                       40                       45

Gly  Ala  Gly  Ala  Gly  Ser  Gly  Ala  Gly  Ala  Gly  Ser  Gly  Ala  Gly  Ala
              50                       55                       60

Gly  Ser  Gly  Ala  Gly  Ala  Gly  Ser  Gly  Ala  Ala  Val  Thr  Gly  Arg  Gly
    65                       70                       75                       80

Asp  Ser  Pro  Ala  Ser  Ala  Ala  Gly  Tyr  Gly  Ala  Gly  Ala  Gly  Ser  Gly
              85                       90                       95

Ala  Gly  Ala  Gly  Ser  Gly  Ala  Gly  Ala  Gly  Ser  Gly  Ala  Gly  Ala  Gly
                   100                      105                      110

Ser  Gly  Ala  Gly  Ala  Gly  Ser  Gly  Ala  Gly  Ala  Gly  Ser  Gly  Ala  Gly
              115                      120                      125

Ala  Gly  Ser  Gly  Ala  Gly  Ala  Gly  Ser  Gly  Ala  Gly  Ala  Gly  Ser  Gly
    130                      135                      140

Ala  Ala  Val  Thr  Gly  Arg  Gly  Asp  Ser  Pro  Ala  Ser  Ala  Ala  Gly  Tyr
    145                      150                      155                      160

Gly  Ala  Gly  Ala  Gly  Ser  Gly  Ala  Gly  Ala  Gly  Ser  Gly  Ala  Gly  Ala
                   165                      170                      175

Gly  Ser  Gly  Ala  Gly  Ala  Gly  Ser  Gly  Ala  Gly  Ala  Gly  Ser  Gly  Ala
              180                      185                      190

Gly  Ala  Gly  Ser  Gly  Ala  Gly  Ala  Gly  Ser  Gly  Ala  Gly  Ala  Gly  Ser
              195                      200                      205

Gly  Ala  Gly  Ala  Gly  Ser  Gly  Ala  Ala  Val  Thr  Gly  Arg  Gly  Asp  Ser
    210                      215                      220

Pro  Ala  Ser  Ala  Ala  Gly  Tyr  Gly  Ala  Gly  Ala  Gly  Ser  Gly  Ala  Gly
    225                      230                      235                      240

Ala  Gly  Ser  Gly  Ala  Gly  Ala  Gly  Ser  Gly  Ala  Gly  Ala  Gly  Ser  Gly
                   245                      250                      255

Ala  Gly  Ala  Gly  Ser  Gly  Ala  Gly  Ala  Gly  Ser  Gly  Ala  Gly  Ala  Gly
                   260                      265                      270

Ser  Gly  Ala  Gly  Ala  Gly  Ser  Gly  Ala  Gly  Ala  Gly  Ser  Gly  Ala  Ala
              275                      280                      285

Val  Thr  Gly  Arg  Gly  Asp  Ser  Pro  Ala  Ser  Ala  Ala  Gly  Tyr  Gly  Ala
    290                      295                      300

| Gly | Ala | Gly | Ser | Gly | Ala | Gly | Ala | Gly | Ser | Gly | Ala | Gly | Ala | Gly | Ser |
|-----|-----|-----|-----|-----|-----|-----|-----|-----|-----|-----|-----|-----|-----|-----|-----|
| 305 | | | | 310 | | | | 315 | | | | | | | 320 |
| Gly | Ala | Gly | Ala | Gly | Ser | Gly | Ala | Gly | Ala | Gly | Ser | Gly | Ala | Gly | Ala |
| | | | | 325 | | | | | 330 | | | | | | 335 |
| Gly | Ser | Gly | Ala | Gly | Ala | Gly | Ser | Gly | Ala | Gly | Ala | Gly | Ser | Gly | Ala |
| | | | 340 | | | | | 345 | | | | | 350 | | |
| Gly | Ala | Gly | Ser | Gly | Ala | Ala | Val | Thr | Gly | Arg | Gly | Asp | Ser | Pro | Ala |
| | | 355 | | | | | 360 | | | | 365 | | | | |
| Ser | Ala | Ala | Gly | Tyr | Gly | Ala | Gly | Ala | Gly | Ser | Gly | Ala | Gly | Ala | Gly |
| | 370 | | | | 375 | | | | 380 | | | | | | |
| Ser | Gly | Ala | Gly | Ala | Gly | Ser | Gly | Ala | Gly | Ala | Gly | Ser | Gly | Ala | Gly |
| 385 | | | | 390 | | | | 395 | | | | | | | 400 |
| Ala | Gly | Ser | Gly | Ala | Gly | Ala | Gly | Ser | Gly | Ala | Gly | Ala | Gly | Ser | Gly |
| | | | | 405 | | | | 410 | | | | | | 415 | |
| Ala | Gly | Ala | Gly | Ser | Gly | Ala | Gly | Ala | Gly | Ser | Gly | Ala | Ala | Val | Thr |
| | | | 420 | | | | | 425 | | | | | 430 | | |
| Gly | Arg | Gly | Asp | Ser | Pro | Ala | Ser | Ala | Ala | Gly | Tyr | Gly | Ala | Gly | Ala |
| | | 435 | | | | | 440 | | | | | 445 | | | |
| Gly | Ser | Gly | Ala | Gly | Ala | Gly | Ser | Gly | Ala | Gly | Ala | Gly | Ser | Gly | Ala |
| | 450 | | | | | 455 | | | | | 460 | | | | |
| Gly | Ala | Gly | Ser | Gly | Ala | Gly | Ala | Gly | Ser | Gly | Ala | Gly | Ala | Gly | Ser |
| 465 | | | | | 470 | | | | 475 | | | | | | 480 |
| Gly | Ala | Gly | Ala | Gly | Ser | Gly | Ala | Gly | Ala | Gly | Ser | Gly | Ala | Gly | Ala |
| | | | | 485 | | | | | 490 | | | | | | 495 |
| Gly | Ser | Gly | Ala | Ala | Val | Thr | Gly | Arg | Gly | Asp | Ser | Pro | Ala | Ser | Ala |
| | | | 500 | | | | | 505 | | | | | 510 | | |
| Ala | Gly | Tyr | Gly | Ala | Gly | Ala | Gly | Ser | Gly | Ala | Gly | Ala | Gly | Ser | Gly |
| | | 515 | | | | | 520 | | | | | 525 | | | |
| Ala | Gly | Ala | Gly | Ser | Gly | Ala | Gly | Ala | Gly | Ser | Gly | Ala | Gly | Ala | Gly |
| | 530 | | | | | 535 | | | | | 540 | | | | |
| Ser | Gly | Ala | Gly | Ala | Gly | Ser | Gly | Ala | Gly | Ala | Gly | Ser | Gly | Ala | Gly |
| 545 | | | | | 550 | | | | 555 | | | | | | 560 |
| Ala | Gly | Ser | Gly | Ala | Gly | Ala | Gly | Ser | Gly | Ala | Ala | Val | Thr | Gly | Arg |
| | | | | 565 | | | | | 570 | | | | | | 575 |
| Gly | Asp | Ser | Pro | Ala | Ser | Ala | Ala | Gly | Tyr | Gly | Ala | Gly | Ala | Gly | Ser |
| | | | 580 | | | | | 585 | | | | | 590 | | |
| Gly | Ala | Gly | Ala | Gly | Ser | Gly | Ala | Gly | Ala | Gly | Ser | Gly | Ala | Gly | Ala |
| | | 595 | | | | | 600 | | | | | 605 | | | |
| Gly | Ser | Gly | Ala | Gly | Ala | Gly | Ser | Gly | Ala | Gly | Ala | Gly | Ser | Gly | Ala |
| | 610 | | | | | 615 | | | | | 620 | | | | |
| Gly | Ala | Gly | Ser | Gly | Ala | Gly | Ala | Gly | Ser | Gly | Ala | Gly | Ala | Gly | Ser |
| 625 | | | | | 630 | | | | 635 | | | | | | 640 |
| Gly | Ala | Ala | Val | Thr | Gly | Arg | Gly | Asp | Ser | Pro | Ala | Ser | Ala | Ala | Gly |
| | | | | 645 | | | | | 650 | | | | | | 655 |
| Tyr | Gly | Ala | Gly | Ala | Gly | Ser | Gly | Ala | Gly | Ala | Gly | Ser | Gly | Ala | Gly |
| | | | 660 | | | | | 665 | | | | | 670 | | |
| Ala | Gly | Ser | Gly | Ala | Gly | Ala | Gly | Ser | Gly | Ala | Gly | Ala | Gly | Ser | Gly |
| | | 675 | | | | | 680 | | | | | 685 | | | |
| Ala | Gly | Ala | Gly | Ser | Gly | Ala | Gly | Ala | Gly | Ser | Gly | Ala | Gly | Ala | Gly |
| | 690 | | | | | 695 | | | | | 700 | | | | |
| Ser | Gly | Ala | Gly | Ala | Gly | Ser | Gly | Ala | Ala | Val | Thr | Gly | Arg | Gly | Asp |
| 705 | | | | | 710 | | | | 715 | | | | | | 720 |
| Ser | Pro | Ala | Ser | Ala | Ala | Gly | Tyr | Gly | Ala | Gly | Ala | Gly | Ser | Gly | Ala |

|  |  |  |  |  | 725 |  |  |  |  | 730 |  |  |  |  | 735 |  |
|---|---|---|---|---|---|---|---|---|---|---|---|---|---|---|---|---|
| Gly | Ala | Gly | Ser | Gly | Ala | Gly | Ala | Met | Asp | Pro | Gly | Arg | Tyr | Gln | Leu |
|  |  |  | 740 |  |  |  |  | 745 |  |  |  |  | 750 |  |  |
| Ser | Ala | Gly | Arg | Tyr | His | Tyr | Gln | Leu | Val | Trp | Cys | Gln | Lys |  |  |
|  |  |  | 755 |  |  |  |  | 760 |  |  |  |  | 765 |  |  |

( 2 ) INFORMATION FOR SEQ ID NO:54:

( i ) SEQUENCE CHARACTERISTICS:
        ( A ) LENGTH: 1050 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:54:

| Asp | Pro | Val | Val | Leu | Gln | Arg | Arg | Asp | Trp | Glu | Asn | Pro | Gly | Val | Thr |
|---|---|---|---|---|---|---|---|---|---|---|---|---|---|---|---|
| 1 |  |  |  | 5 |  |  |  |  | 10 |  |  |  |  | 15 |  |
| Gln | Leu | Asn | Arg | Leu | Ala | Ala | His | Pro | Pro | Phe | Ala | Ser | Asp | Pro | Met |
|  |  |  | 20 |  |  |  |  | 25 |  |  |  |  | 30 |  |  |
| Gly | Ala | Gly | Ser | Gly | Ala | Gly | Ala | Gly | Ser | Gly | Ala | Gly | Ala | Gly | Ser |
|  |  |  | 35 |  |  |  |  | 40 |  |  |  |  | 45 |  |  |
| Gly | Ala | Gly | Ala | Gly | Ser | Gly | Ala | Gly | Ala | Gly | Ser | Gly | Ala | Gly | Ala |
|  | 50 |  |  |  |  | 55 |  |  |  |  |  | 60 |  |  |  |
| Gly | Ser | Gly | Ala | Gly | Ala | Gly | Ser | Gly | Ala | Ala | Val | Thr | Gly | Arg | Gly |
| 65 |  |  |  |  | 70 |  |  |  |  | 75 |  |  |  |  | 80 |
| Asp | Ser | Pro | Ala | Ser | Ala | Ala | Gly | Tyr | Gly | Ala | Gly | Ala | Gly | Ser | Gly |
|  |  |  |  | 85 |  |  |  |  | 90 |  |  |  |  | 95 |  |
| Ala | Gly | Ala | Gly | Ser | Gly | Ala | Gly | Ala | Gly | Ser | Gly | Ala | Gly | Ala | Gly |
|  |  |  | 100 |  |  |  |  | 105 |  |  |  |  | 110 |  |  |
| Ser | Gly | Ala | Gly | Ala | Gly | Ser | Gly | Ala | Gly | Ala | Gly | Ser | Gly | Ala | Gly |
|  |  |  | 115 |  |  |  |  | 120 |  |  |  |  | 125 |  |  |
| Ala | Gly | Ser | Gly | Ala | Gly | Ala | Gly | Ser | Gly | Ala | Gly | Ala | Gly | Ser | Gly |
|  | 130 |  |  |  |  | 135 |  |  |  |  |  | 140 |  |  |  |
| Ala | Ala | Val | Thr | Gly | Arg | Gly | Asp | Ser | Pro | Ala | Ser | Ala | Ala | Gly | Tyr |
| 145 |  |  |  |  | 150 |  |  |  |  | 155 |  |  |  |  | 160 |
| Gly | Ala | Gly | Ala | Gly | Ser | Gly | Ala | Gly | Ala | Gly | Ser | Gly | Ala | Gly | Ala |
|  |  |  |  | 165 |  |  |  |  | 170 |  |  |  |  | 175 |  |
| Gly | Ser | Gly | Ala | Gly | Ala | Gly | Ser | Gly | Ala | Gly | Ala | Gly | Ser | Gly | Ala |
|  |  |  | 180 |  |  |  |  | 185 |  |  |  |  | 190 |  |  |
| Gly | Ala | Gly | Ser | Gly | Ala | Gly | Ala | Gly | Ser | Gly | Ala | Gly | Ala | Gly | Ser |
|  |  |  | 195 |  |  |  |  | 200 |  |  |  |  | 205 |  |  |
| Gly | Ala | Gly | Ala | Gly | Ser | Gly | Ala | Ala | Val | Thr | Gly | Arg | Gly | Asp | Ser |
|  | 210 |  |  |  |  | 215 |  |  |  |  |  | 220 |  |  |  |
| Pro | Ala | Ser | Ala | Ala | Gly | Tyr | Gly | Ala | Gly | Ala | Gly | Ser | Gly | Ala | Gly |
| 225 |  |  |  |  | 230 |  |  |  |  | 235 |  |  |  |  | 240 |
| Ala | Gly | Ser | Gly | Ala | Gly | Ala | Gly | Ser | Gly | Ala | Gly | Ala | Gly | Ser | Gly |
|  |  |  |  | 245 |  |  |  |  | 250 |  |  |  |  | 255 |  |
| Ala | Gly | Ala | Gly | Ser | Gly | Ala | Gly | Ala | Gly | Ser | Gly | Ala | Gly | Ala | Gly |
|  |  |  | 260 |  |  |  |  | 265 |  |  |  |  | 270 |  |  |
| Ser | Gly | Ala | Gly | Ala | Gly | Ser | Gly | Ala | Gly | Ala | Gly | Ser | Gly | Ala | Ala |
|  |  |  | 275 |  |  |  |  | 280 |  |  |  |  | 285 |  |  |
| Val | Thr | Gly | Arg | Gly | Asp | Ser | Pro | Ala | Ser | Ala | Ala | Gly | Tyr | Gly | Ala |
|  | 290 |  |  |  |  | 295 |  |  |  |  |  | 300 |  |  |  |
| Gly | Ala | Gly | Ser | Gly | Ala | Gly | Ala | Gly | Ser | Gly | Ala | Gly | Ala | Gly | Ser |
| 305 |  |  |  |  | 310 |  |  |  |  | 315 |  |  |  |  | 320 |

| | | | | | | | | | | | | | | | |
|---|---|---|---|---|---|---|---|---|---|---|---|---|---|---|---|
| Gly | Ala | Gly | Ala | Gly 325 | Ser | Gly | Ala | Gly 330 | Gly | Ser | Gly | Ala | Gly 335 | Ala | |
| Gly | Ser | Gly | Ala 340 | Gly | Ala | Gly | Ser 345 | Gly | Ala | Gly | Ala | Gly | Ser 350 | Gly | Ala |
| Gly | Ala | Gly | Ser 355 | Gly | Ala | Ala | Val 360 | Thr | Gly | Arg | Gly | Asp 365 | Ser | Pro | Ala |
| Ser | Ala 370 | Ala | Gly | Tyr | Gly 375 | Ala | Gly | Ala | Gly | Ser 380 | Gly | Ala | Gly | Ala | Gly |
| Ser 385 | Gly | Ala | Gly | Ala | Gly 390 | Ser | Gly | Ala | Gly | Ala 395 | Gly | Ser | Gly | Ala | Gly 400 |
| Ala | Gly | Ser | Gly | Ala 405 | Gly | Ala | Gly | Ser 410 | Gly | Ala | Gly | Ala | Gly 415 | Ser | Gly |
| Ala | Gly | Ala | Gly 420 | Ser | Gly | Ala | Gly | Ala 425 | Gly | Ser | Gly | Ala | Ala 430 | Val | Thr |
| Gly | Arg | Gly 435 | Asp | Ser | Pro | Ala | Ser 440 | Ala | Ala | Gly | Tyr | Gly 445 | Ala | Gly | Ala |
| Gly | Ser 450 | Gly | Ala | Gly | Ala | Gly 455 | Ser | Gly | Ala | Gly | Ala 460 | Gly | Ser | Gly | Ala |
| Gly 465 | Ala | Gly | Ser | Gly | Ala 470 | Gly | Ala | Gly | Ser 475 | Gly | Ala | Gly | Ala | Gly | Ser 480 |
| Gly | Ala | Gly | Ala | Gly 485 | Ser | Gly | Ala | Gly 490 | Ala | Gly | Ser | Gly | Ala | Gly 495 | Ala |
| Gly | Ser | Gly | Ala 500 | Ala | Val | Thr | Gly | Arg 505 | Gly | Asp | Ser | Pro | Ala 510 | Ser | Ala |
| Ala | Gly | Tyr 515 | Gly | Ala | Gly | Ala | Gly 520 | Ser | Gly | Ala | Gly | Ala 525 | Gly | Ser | Gly |
| Ala | Gly 530 | Ala | Gly | Ser | Gly | Ala 535 | Gly | Ala | Gly | Ser | Gly 540 | Ala | Gly | Ala | Gly |
| Ser 545 | Gly | Ala | Gly | Ala | Gly 550 | Ser | Gly | Ala | Gly | Ala 555 | Gly | Ser | Gly | Ala | Gly 560 |
| Ala | Gly | Ser | Gly | Ala 565 | Gly | Ala | Gly | Ser 570 | Gly | Ala | Ala | Val | Thr | Gly | Arg 575 |
| Gly | Asp | Ser | Pro 580 | Ala | Ser | Ala | Ala | Gly 585 | Tyr | Gly | Ala | Gly | Ala 590 | Gly | Ser |
| Gly | Ala | Gly 595 | Ala | Gly | Ser | Gly | Ala 600 | Gly | Ala | Gly | Ser | Gly 605 | Ala | Gly | Ala |
| Gly | Ser 610 | Gly | Ala | Gly | Ala | Gly 615 | Ser | Gly | Ala | Gly | Ala 620 | Gly | Ser | Gly | Ala |
| Gly 625 | Ala | Gly | Ser | Gly | Ala 630 | Gly | Ala | Gly | Ser 635 | Gly | Ala | Gly | Ala | Gly | Ser 640 |
| Gly | Ala | Ala | Val | Thr 645 | Gly | Arg | Gly | Asp | Ser 650 | Pro | Ala | Ser | Ala | Ala 655 | Gly |
| Tyr | Gly | Ala | Gly 660 | Ala | Gly | Ser | Gly | Ala 665 | Gly | Ala | Gly | Ser | Gly 670 | Ala | Gly |
| Ala | Gly | Ser 675 | Gly | Ala | Gly | Ala | Gly 680 | Ser | Gly | Ala | Gly | Ala 685 | Gly | Ser | Gly |
| Ala | Gly 690 | Ala | Gly | Ser | Gly | Ala 695 | Gly | Ala | Gly | Ser | Gly 700 | Ala | Gly | Ala | Gly |
| Ser 705 | Gly | Ala | Gly | Ala | Gly 710 | Ser | Gly | Ala | Ala | Val 715 | Thr | Gly | Arg | Gly | Asp 720 |
| Ser | Pro | Ala | Ser | Ala 725 | Ala | Gly | Tyr | Gly 730 | Ala | Gly | Ala | Gly | Ser 735 | Gly | Ala |
| Gly | Ala | Gly | Ser | Gly | Ala | Gly | Ala | Gly | Ser | Gly | Ala | Gly | Ala | Gly | Ser |

|     |     |     |     | 740 |     |     |     | 745 |     |     |     | 750 |     |
|-----|-----|-----|-----|-----|-----|-----|-----|-----|-----|-----|-----|-----|-----|

Gly Ala Gly Ala Gly Ser Gly Ala Gly Ala Gly Ser Gly Ala Gly Ala
                755                 760                 765

Gly Ser Gly Ala Gly Ala Gly Ser Gly Ala Gly Ala Gly Ser Gly Ala
        770                 775                 780

Ala Val Thr Gly Arg Gly Asp Ser Pro Ala Ser Ala Ala Gly Tyr Gly
785                 790                 795                 800

Ala Gly Ala Gly Ser Gly Ala Gly Ala Gly Ser Gly Ala Gly Ala Gly
                805                 810                 815

Ser Gly Ala Gly Ala Gly Ser Gly Ala Gly Ala Gly Ser Gly Ala Gly
            820                 825                 830

Ala Gly Ser Gly Ala Gly Ala Gly Ser Gly Ala Gly Ala Gly Ser Gly
            835                 840                 845

Ala Gly Ala Gly Ser Gly Ala Ala Val Thr Gly Arg Gly Asp Ser Pro
    850                 855                 860

Ala Ser Ala Ala Gly Tyr Gly Ala Gly Ala Gly Ser Gly Ala Gly Ala
865                 870                 875                 880

Gly Ser Gly Ala Gly Ala Gly Ser Gly Ala Gly Ala Gly Ser Gly Ala
                885                 890                 895

Gly Ala Gly Ser Gly Ala Gly Ala Gly Ser Gly Ala Gly Ala Gly Ser
            900                 905                 910

Gly Ala Gly Ala Gly Ser Gly Ala Gly Ala Gly Ser Gly Ala Ala Val
            915                 920                 925

Thr Gly Arg Gly Asp Ser Pro Ala Ser Ala Ala Gly Tyr Gly Ala Gly
    930                 935                 940

Ala Gly Ser Gly Ala Gly Ala Gly Ser Gly Ala Gly Ala Gly Ser Gly
945                 950                 955                 960

Ala Gly Ala Gly Ser Gly Ala Gly Ala Gly Ser Gly Ala Gly Ala Gly
                965                 970                 975

Ser Gly Ala Gly Ala Gly Ser Gly Ala Gly Ala Gly Ser Gly Ala Gly
            980                 985                 990

Ala Gly Ser Gly Ala Ala Val Thr Gly Arg Gly Asp Ser Pro Ala Ser
            995                 1000                1005

Ala Ala Gly Tyr Gly Ala Gly Ala Gly Ser Gly Ala Gly Ala Gly Ser
        1010                1015                1020

Gly Ala Gly Ala Met Asp Pro Gly Arg Tyr Gln Leu Ser Ala Gly Arg
1025                1030                1035                1040

Tyr His Tyr Gln Leu Val Trp Cys Gln Lys
                1045                1050

( 2 ) INFORMATION FOR SEQ ID NO:55:

( i ) SEQUENCE CHARACTERISTICS:
        ( A ) LENGTH: 51 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:55:

GTGCTGCGGA TGCTCGAGAT GGTGCATGCA TGTACATCCG AGTACTTCGA T      51

( 2 ) INFORMATION FOR SEQ ID NO:56:

( i ) SEQUENCE CHARACTERISTICS:
        ( A ) LENGTH: 47 base pairs
        ( B ) TYPE: nucleic acid (C) STRANDEDNESS: single
(D) TOPOLOGY: linear (i i) MOLECULE TYPE: cDNA (x i) SEQUENCE DESCRIPTION: SEQ ID NO:56:

ATCGAACTAC TCGGATCTAC ATGCATGCA CCATCTCGAGC ATCCGCA                47

(2) INFORMATION FOR SEQ ID NO:57:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (i i) MOLECULE TYPE: cDNA (x i) SEQUENCE DESCRIPTION: SEQ ID NO:57:

CTACATGTGT TACACATCCC GTGC                                         24

(2) INFORMATION FOR SEQ ID NO:58:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (i i) MOLECULE TYPE: cDNA (x i) SEQUENCE DESCRIPTION: SEQ ID NO:58:

GCACGGGATG TGTAACACAT GTAGAGCC                                     28

(2) INFORMATION FOR SEQ ID NO:59:

(i) SEQUENCE CHARACTERISTICS:
        (A) LENGTH: 1170 amino acids
        (B) TYPE: amino acid
        (C) STRANDEDNESS: single
        (D) TOPOLOGY: linear (i i) MOLECULE TYPE: peptide (x i) SEQUENCE DESCRIPTION: SEQ ID NO:59:

```
Met Asp Pro Val Val Leu Gln Arg Arg Asp Trp Glu Asn Pro Gly Val
 1               5                  10                  15
Thr Gln Leu Asn Arg Leu Ala Ala His Pro Pro Phe Ala Ser Asp Pro
            20                  25                  30
Met Gly Ala Gly Ser Gly Ala Gly Ala Gly Ser Gly Ala Gly Ala Gly
            35                  40                  45
Ser Gly Val Gly Val Pro Gly Val Gly Val Pro Gly Val Gly Val Pro
     50                 55                   60
Gly Val Gly Val Pro Gly Val Gly Val Pro Gly Val Gly Val Pro Gly
 65                  70                  75                  80
Val Gly Val Pro Gly Val Gly Val Pro Gly Ala Gly Ala Gly Ser Gly
                 85                  90                  95
Ala Gly Ala Gly Ser Gly Ala Gly Ala Gly Ser Gly Ala Gly Ala Gly
            100                 105                 110
Ser Gly Ala Gly Ala Gly Ser Gly Ala Gly Ala Gly Ser Gly Ala Gly
            115                 120                 125
Ala Gly Ser Gly Ala Gly Ala Gly Ser Gly Ala Gly Ala Gly Ser Gly
            130                 135                 140
Ala Gly Ala Gly Ser Gly Ala Gly Ala Gly Ser Gly Ala Gly Ala Gly
```

-continued

|     |     |     |     | 145 |     |     |     |     | 150 |     |     |     |     | 155 |     |     |     |     | 160 |
| --- | --- | --- | --- | --- | --- | --- | --- | --- | --- | --- | --- | --- | --- | --- | --- | --- | --- | --- | --- |
| Ser | Gly | Ala | Ala | Val | Thr | Gly | Arg | Gly | Asp | Ser | Pro | Ala | Ser | Ala | Ala |
|     |     |     |     |     | 165 |     |     |     |     | 170 |     |     |     |     | 175 |
| Gly | Tyr | Gly | Ala | Gly | Ala | Gly | Ser | Gly | Ala | Gly | Ala | Gly | Ser | Gly | Ala |
|     |     |     |     |     | 180 |     |     |     |     | 185 |     |     |     |     | 190 |
| Gly | Ala | Gly | Ser | Gly | Ala | Gly | Ala | Gly | Ser | Gly | Ala | Gly | Ala | Gly | Ser |
|     |     |     | 195 |     |     |     |     | 200 |     |     |     |     | 205 |     |     |
| Gly | Val | Gly | Val | Pro | Gly | Val | Gly | Val | Pro | Gly | Val | Gly | Val | Pro | Gly |
|     | 210 |     |     |     |     | 215 |     |     |     |     | 220 |     |     |     |     |
| Val | Gly | Val | Pro | Gly | Val | Gly | Val | Pro | Gly | Val | Gly | Val | Pro | Gly | Val |
| 225 |     |     |     |     | 230 |     |     |     |     | 235 |     |     |     |     | 240 |
| Gly | Val | Pro | Gly | Val | Gly | Val | Pro | Gly | Ala | Gly | Ala | Gly | Ser | Gly | Ala |
|     |     |     |     | 245 |     |     |     |     | 250 |     |     |     |     | 255 |     |
| Gly | Ala | Gly | Ser | Gly | Ala | Gly | Ala | Gly | Ser | Gly | Ala | Gly | Ala | Gly | Ser |
|     |     |     | 260 |     |     |     |     | 265 |     |     |     |     | 270 |     |     |
| Gly | Ala | Gly | Ala | Gly | Ser | Gly | Ala | Gly | Ala | Gly | Ser | Gly | Ala | Gly | Ala |
|     |     |     |     | 275 |     |     |     |     | 280 |     |     |     |     | 285 |     |
| Gly | Ser | Gly | Ala | Gly | Ala | Gly | Ser | Gly | Ala | Gly | Ala | Gly | Ser | Gly | Ala |
|     | 290 |     |     |     |     | 295 |     |     |     |     | 300 |     |     |     |     |
| Gly | Ala | Gly | Ser | Gly | Ala | Gly | Ala | Gly | Ser | Gly | Ala | Gly | Ala | Gly | Ser |
| 305 |     |     |     |     | 310 |     |     |     |     | 315 |     |     |     |     | 320 |
| Gly | Ala | Ala | Val | Thr | Gly | Arg | Gly | Asp | Ser | Pro | Ala | Ser | Ala | Ala | Gly |
|     |     |     |     | 325 |     |     |     |     | 330 |     |     |     |     | 335 |     |
| Tyr | Gly | Ala | Gly | Ala | Gly | Ser | Gly | Ala | Gly | Ala | Gly | Ser | Gly | Ala | Gly |
|     |     |     | 340 |     |     |     |     | 345 |     |     |     |     | 350 |     |     |
| Ala | Gly | Ser | Gly | Ala | Gly | Ala | Gly | Ser | Gly | Ala | Gly | Ala | Gly | Ser | Gly |
|     |     |     |     | 355 |     |     |     |     | 360 |     |     |     |     | 365 |     |
| Val | Gly | Val | Pro | Gly | Val | Gly | Val | Pro | Gly | Val | Gly | Val | Pro | Gly | Val |
|     | 370 |     |     |     |     | 375 |     |     |     |     | 380 |     |     |     |     |
| Gly | Val | Pro | Gly | Val | Gly | Val | Pro | Gly | Val | Gly | Val | Pro | Gly | Val | Gly |
| 385 |     |     |     |     | 390 |     |     |     |     | 395 |     |     |     |     | 400 |
| Val | Pro | Gly | Val | Gly | Val | Pro | Gly | Ala | Gly | Ala | Gly | Ser | Gly | Ala | Gly |
|     |     |     |     | 405 |     |     |     |     | 410 |     |     |     |     | 415 |     |
| Ala | Gly | Ser | Gly | Ala | Gly | Ala | Gly | Ser | Gly | Ala | Gly | Ala | Gly | Ser | Gly |
|     |     |     | 420 |     |     |     |     | 425 |     |     |     |     | 430 |     |     |
| Ala | Gly | Ala | Gly | Ser | Gly | Ala | Gly | Ala | Gly | Ser | Gly | Ala | Gly | Ala | Gly |
|     |     |     | 435 |     |     |     |     | 440 |     |     |     |     | 445 |     |     |
| Ser | Gly | Ala | Gly | Ala | Gly | Ser | Gly | Ala | Gly | Ala | Gly | Ser | Gly | Ala | Gly |
|     | 450 |     |     |     |     | 455 |     |     |     |     | 460 |     |     |     |     |
| Ala | Gly | Ser | Gly | Ala | Gly | Ala | Gly | Ser | Gly | Ala | Gly | Ala | Gly | Ser | Gly |
| 465 |     |     |     |     | 470 |     |     |     |     | 475 |     |     |     |     | 480 |
| Ala | Ala | Val | Thr | Gly | Arg | Gly | Asp | Ser | Pro | Ala | Ser | Ala | Ala | Gly | Tyr |
|     |     |     |     | 485 |     |     |     |     | 490 |     |     |     |     | 495 |     |
| Gly | Ala | Gly | Ala | Gly | Ser | Gly | Ala | Gly | Ala | Gly | Ser | Gly | Ala | Gly | Ala |
|     |     |     |     | 500 |     |     |     |     | 505 |     |     |     |     | 510 |     |
| Gly | Ser | Gly | Ala | Gly | Ala | Gly | Ser | Gly | Ala | Gly | Ala | Gly | Ser | Gly | Val |
|     |     |     | 515 |     |     |     |     | 520 |     |     |     |     | 525 |     |     |
| Gly | Val | Pro | Gly | Val | Gly | Val | Pro | Gly | Val | Gly | Val | Pro | Gly | Val | Gly |
|     |     | 530 |     |     |     |     | 535 |     |     |     |     | 540 |     |     |     |
| Val | Pro | Gly | Val | Gly | Val | Pro | Gly | Val | Gly | Val | Pro | Gly | Val | Gly | Val |
| 545 |     |     |     |     | 550 |     |     |     |     | 555 |     |     |     |     | 560 |
| Pro | Gly | Val | Gly | Val | Pro | Gly | Ala | Gly | Ala | Gly | Ser | Gly | Ala | Gly | Ala |
|     |     |     |     | 565 |     |     |     |     | 570 |     |     |     |     | 575 |     |

```
Gly  Ser  Gly  Ala  Gly  Ala  Gly  Ser  Gly  Ala  Gly  Ala  Gly  Ser  Gly  Ala
               580                      585                     590
Gly  Ala  Gly  Ser  Gly  Ala  Gly  Ala  Gly  Ser  Gly  Ala  Gly  Ala  Gly  Ser
               595                      600                     605
Gly  Ala  Gly  Ala  Gly  Ser  Gly  Ala  Gly  Ala  Gly  Ser  Gly  Ala  Gly  Ala
               610                      615                     620
Gly  Ser  Gly  Ala  Gly  Ala  Gly  Ser  Gly  Ala  Gly  Ala  Gly  Ser  Gly  Ala
625                          630                     635                     640
Ala  Val  Thr  Gly  Arg  Gly  Asp  Ser  Pro  Ala  Ser  Ala  Ala  Gly  Tyr  Gly
                    645                      650                     655
Ala  Gly  Ala  Gly  Ser  Gly  Ala  Gly  Ala  Gly  Ser  Gly  Ala  Gly  Ala  Gly
               660                      665                     670
Ser  Gly  Ala  Gly  Ala  Gly  Ser  Gly  Ala  Gly  Ala  Gly  Ser  Gly  Val  Gly
               675                      680                     685
Val  Pro  Gly  Val  Gly  Val  Pro  Gly  Val  Gly  Val  Pro  Gly  Val  Gly  Val
690                          695                     700
Pro  Gly  Val  Gly  Val  Pro  Gly  Val  Gly  Val  Pro  Gly  Val  Gly  Val  Pro
705                          710                     715                     720
Gly  Val  Gly  Val  Pro  Gly  Ala  Gly  Ala  Gly  Ser  Gly  Ala  Gly  Ala  Gly
                    725                      730                     735
Ser  Gly  Ala  Gly  Ala  Gly  Ser  Gly  Ala  Gly  Ala  Gly  Ser  Gly  Ala  Gly
               740                      745                     750
Ala  Gly  Ser  Gly  Ala  Gly  Ala  Gly  Ser  Gly  Ala  Gly  Ala  Gly  Ser  Gly
               755                      760                     765
Ala  Gly  Ala  Gly  Ser  Gly  Ala  Gly  Ala  Gly  Ser  Gly  Ala  Gly  Ala  Gly
               770                      775                     780
Ser  Gly  Ala  Gly  Ala  Gly  Ser  Gly  Ala  Gly  Ala  Gly  Ser  Gly  Ala  Ala
785                          790                     795                     800
Val  Thr  Gly  Arg  Gly  Asp  Ser  Pro  Ala  Ser  Ala  Ala  Gly  Tyr  Gly  Ala
                    805                      810                     815
Gly  Ala  Gly  Ser  Gly  Ala  Gly  Ala  Gly  Ser  Gly  Ala  Gly  Ala  Gly  Ser
               820                      825                     830
Gly  Ala  Gly  Ala  Gly  Ser  Gly  Ala  Gly  Ala  Gly  Ser  Gly  Val  Gly  Val
               835                      840                     845
Pro  Gly  Val  Gly  Val  Pro  Gly  Val  Gly  Val  Pro  Gly  Val  Gly  Val  Pro
850                          855                     860
Gly  Val  Gly  Val  Pro  Gly  Val  Gly  Val  Pro  Gly  Val  Gly  Val  Pro  Gly
865                          870                     875                     880
Val  Gly  Val  Pro  Gly  Ala  Gly  Ala  Gly  Ser  Gly  Ala  Gly  Ala  Gly  Ser
                    885                      890                     895
Gly  Ala  Gly  Ala  Gly  Ser  Gly  Ala  Gly  Ala  Gly  Ser  Gly  Ala  Gly  Ala
               900                      905                     910
Gly  Ser  Gly  Ala  Gly  Ala  Gly  Ser  Gly  Ala  Gly  Ala  Gly  Ser  Gly  Ala
               915                      920                     925
Gly  Ala  Gly  Ser  Gly  Ala  Gly  Ala  Gly  Ser  Gly  Ala  Gly  Ala  Gly  Ser
               930                      935                     940
Gly  Ala  Gly  Ala  Gly  Ser  Gly  Ala  Gly  Ala  Gly  Ser  Gly  Ala  Ala  Val
945                          950                     955                     960
Thr  Gly  Arg  Gly  Asp  Ser  Pro  Ala  Ser  Ala  Ala  Gly  Tyr  Gly  Ala  Gly
                    965                      970                     975
Ala  Gly  Ser  Gly  Ala  Gly  Ala  Gly  Ser  Gly  Ala  Gly  Ala  Gly  Ser  Gly
               980                      985                     990
Ala  Gly  Ala  Gly  Ser  Gly  Ala  Gly  Ala  Gly  Ser  Gly  Val  Gly  Val  Pro
               995                      1000                    1005
```

Gly Val Gly Val Pro Gly Val Gly Val Pro Gly Val Gly Val Pro Gly
                1010                1015                1020

Val Gly Val Pro Gly Val Gly Val Pro Gly Val Gly Val Pro Gly Val
1025                1030                1035                1040

Gly Val Pro Gly Ala Gly Ala Gly Ser Gly Ala Gly Ala Gly Ser Gly
                1045                1050                1055

Ala Gly Ala Gly Ser Gly Ala Gly Ala Gly Ser Gly Ala Gly Ala Gly
                1060                1065                1070

Ser Gly Ala Gly Ala Gly Ser Gly Ala Gly Ala Gly Ser Gly Ala Gly
                1075                1080                1085

Ala Gly Ser Gly Ala Gly Ala Gly Ser Gly Ala Gly Ala Gly Ser Gly
                1090                1095                1100

Ala Gly Ala Gly Ser Gly Ala Gly Ala Gly Ser Gly Ala Ala Val Thr
1105                1110                1115                1120

Gly Arg Gly Asp Ser Pro Ala Ser Ala Ala Gly Tyr Gly Ala Gly Ala
                1125                1130                1135

Gly Ser Gly Ala Gly Ala Gly Ser Gly Ala Gly Ala Met Asp Pro Gly
                1140                1145                1150

Arg Tyr Gln Leu Ser Ala Gly Arg Tyr His Tyr Gln Leu Val Trp Cys
                1155                1160                1165

Gln Lys
1170

( 2 ) INFORMATION FOR SEQ ID NO:60:

( i ) SEQUENCE CHARACTERISTICS:
        ( A ) LENGTH: 63 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:60:

GCTATGTTTA AACCACGTGT TCGCGATCCG GGTGCCGATC CAGGCCTGCG ATATCAGTAC    60

GTA    63

( 2 ) INFORMATION FOR SEQ ID NO:61:

( i ) SEQUENCE CHARACTERISTICS:
        ( A ) LENGTH: 63 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:61:

TACGTACTGA TATCGCAGGC CTGGATCGGC ACCCGGATCG CGAACACGTC CTTTAAACAT    60

AGC    63

( 2 ) INFORMATION FOR SEQ ID NO:62:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:62:

| Ala | Met | Phe | Lys | Pro | Arg | Val | Arg | Asp | Pro | Gly | Ala | Asp | Pro | Gly | Leu |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Arg | Tyr | Gln | Tyr | Val |
|-----|-----|-----|-----|-----|
|     |     |     | 20  |     |

( 2 ) INFORMATION FOR SEQ ID NO:63:

( i ) SEQUENCE CHARACTERISTICS:
        ( A ) LENGTH: 226 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:63:

```
ATGGCAGCGA AAGGGGACCG GTGCCCCGGG TACTCCTGGT CCACAAGGTC TGCCGGGAAG      60
CCCAGGGGCT CCGGGTACTC CAGGTCCGCA AGGCCTGCCG GGTTCACCGG GTGCTCCGGG     120
AACTCCTGGC CCGCAGGGCT TGCCGGGATC CCCAGGTGCA CCAGGAACGC CGGGACCTCA     180
GGGTCTTCCG GGTAGCCCTG GTGCCTTTCC GCTAAAGTCC TGCCGT                    226
```

( 2 ) INFORMATION FOR SEQ ID NO:64:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:64:

```
AAGAAGGAGA TATCATATGG CAGCGAAAGG GGACC                                 35
```

( 2 ) INFORMATION FOR SEQ ID NO:65:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:65:

```
AAAGCGATTT CAGGACGGCA TTAAATTTCT AGACGC                                36
```

( 2 ) INFORMATION FOR SEQ ID NO:66:

( i ) SEQUENCE CHARACTERISTICS:
        ( A ) LENGTH: 186 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:66:

```
GGTGCCCCGG GTACTCCTGG TCCACAAGGT CTGCCGGGAA GCCCAGGGGC TCCGGGTACT      60
CCAGGTCCGC AAGGCCTGCC GGGTTCACCG GGTGCTCCGG GAACTCCTGG CCCGCAGGGC     120
TTGCCGGGAT CCCCAGGTGC ACCAGGAACG CCGGGACCTC AGGGTCTTCC GGGTAGCCCT     180
GGTGCC                                                                186
```

( 2 ) INFORMATION FOR SEQ ID NO:67:

( i ) SEQUENCE CHARACTERISTICS:
        ( A ) LENGTH: 61 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..61
        ( D ) OTHER INFORMATION: /note= "X = G or A"

( x i ) SEQUENCE DESCRIPTION: SEQ ID NO:67:

```
Gly Ala Pro Gly Thr Pro Gly Pro Gln Gly Leu Pro Gly Ser Pro Gly
 1               5                  10                  15

Ala Pro Gly Thr Pro Gly Pro Gln Gly Leu Pro Gly Ser Pro Gly Ala
                20                  25                  30

Pro Gly Thr Pro Gly Pro Gln Gly Leu Pro Gly Ser Pro Gly Ala Pro
                35                  40                  45

Gly Thr Pro Gly Pro Gln Gly Leu Pro Gly Ser Pro Xaa
 50                  55                  60
```

( 2 ) INFORMATION FOR SEQ ID NO:68:

( i ) SEQUENCE CHARACTERISTICS:
        ( A ) LENGTH: 837 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:68:

```
Met Asp Pro Val Val Leu Gln Arg Arg Asp Trp Glu Asn Pro Gly Val
 1               5                  10                  15

Thr Gln Leu Asn Arg Leu Ala Ala His Pro Pro Phe Ala Ser Asp Pro
                20                  25                  30

Met Gly Ala Pro Gly Thr Pro Gly Pro Gln Gly Leu Pro Gly Ser Pro
                35                  40                  45

Gly Ala Pro Gly Thr Pro Gly Pro Gln Gly Leu Pro Gly Ser Pro Gly
         50                  55                  60

Ala Pro Gly Thr Pro Gly Pro Gln Gly Leu Pro Gly Ser Pro Gly Ala
 65                  70                  75                  80

Pro Gly Thr Pro Gly Pro Gln Gly Leu Pro Gly Ser Pro Gly Ala Pro
                85                  90                  95

Gly Thr Pro Gly Pro Gln Gly Leu Pro Gly Ser Pro Gly Ala Pro Gly
                100                 105                 110

Thr Pro Gly Pro Gln Gly Leu Pro Gly Ser Pro Gly Ala Pro Gly Thr
                115                 120                 125

Pro Gly Pro Gln Gly Leu Pro Gly Ser Pro Gly Ala Pro Gly Thr Pro
                130                 135                 140

Gly Pro Gln Gly Leu Pro Gly Ser Pro Gly Ala Pro Gly Thr Pro Gly
 145                 150                 155                 160

Pro Gln Gly Leu Pro Gly Ser Pro Gly Ala Pro Gly Thr Pro Gly Pro
                 165                 170                 175

Gln Gly Leu Pro Gly Ser Pro Gly Ala Pro Gly Thr Pro Gly Pro Gln
                 180                 185                 190

Gly Leu Pro Gly Ser Pro Gly Ala Pro Gly Thr Pro Gly Pro Gln Gly
                 195                 200                 205
```

| | | | | | | | | | | | | | | |
|---|---|---|---|---|---|---|---|---|---|---|---|---|---|---|
| Leu | Pro<br>210 | Gly | Ser | Pro | Gly<br>215 | Ala | Pro | Gly | Thr | Pro<br>220 | Gly | Pro | Gln | Gly | Leu |
| Pro<br>225 | Gly | Ser | Pro | Gly | Ala<br>230 | Pro | Gly | Thr | Pro | Gly<br>235 | Pro | Gln | Gly | Leu | Pro<br>240 |
| Gly | Ser | Pro | Gly | Ala<br>245 | Pro | Gly | Thr | Pro | Gly<br>250 | Pro | Gln | Gly | Leu | Pro<br>255 | Gly |
| Ser | Pro | Gly | Ala<br>260 | Pro | Gly | Thr | Pro | Gly<br>265 | Pro | Gln | Gly | Leu | Pro<br>270 | Gly | Ser |
| Pro | Gly | Ala<br>275 | Pro | Gly | Thr | Pro | Gly<br>280 | Pro | Gln | Gly | Leu | Pro<br>285 | Gly | Ser | Pro |
| Gly | Ala<br>290 | Pro | Gly | Thr | Pro | Gly<br>295 | Pro | Gln | Gly | Leu | Pro<br>300 | Gly | Ser | Pro | Gly |
| Ala<br>305 | Pro | Gly | Thr | Pro | Gly<br>310 | Pro | Gln | Gly | Leu | Pro<br>315 | Gly | Ser | Pro | Gly | Ala<br>320 |
| Pro | Gly | Thr | Pro | Gly<br>325 | Pro | Gln | Gly | Leu | Pro<br>330 | Gly | Ser | Pro | Gly | Ala<br>335 | Pro |
| Gly | Thr | Pro | Gly<br>340 | Pro | Gln | Gly | Leu | Pro<br>345 | Gly | Ser | Pro | Gly | Ala<br>350 | Pro | Gly |
| Thr | Pro | Gly<br>355 | Pro | Gln | Gly | Leu | Pro<br>360 | Gly | Ser | Pro | Gly | Ala<br>365 | Pro | Gly | Thr |
| Pro | Gly<br>370 | Pro | Gln | Gly | Leu | Pro<br>375 | Gly | Ser | Pro | Gly | Ala<br>380 | Pro | Gly | Thr | Pro |
| Gly<br>385 | Pro | Gln | Gly | Leu | Pro<br>390 | Gly | Ser | Pro | Gly | Ala<br>395 | Pro | Gly | Thr | Pro | Gly<br>400 |
| Pro | Gln | Gly | Leu | Pro<br>405 | Gly | Ser | Pro | Gly | Ala<br>410 | Pro | Gly | Thr | Pro | Gly<br>415 | Pro |
| Gln | Gly | Leu | Pro<br>420 | Gly | Ser | Pro | Gly | Ala<br>425 | Pro | Gly | Thr | Pro | Gly<br>430 | Pro | Gln |
| Gly | Leu | Pro<br>435 | Gly | Ser | Pro | Gly | Ala<br>440 | Pro | Gly | Thr | Pro | Gly<br>445 | Pro | Gln | Gly |
| Leu | Pro<br>450 | Gly | Ser | Pro | Gly | Ala<br>455 | Pro | Gly | Thr | Pro | Gly<br>460 | Pro | Gln | Gly | Leu |
| Pro<br>465 | Gly | Ser | Pro | Gly | Ala<br>470 | Pro | Gly | Thr | Pro | Gly<br>475 | Pro | Gln | Gly | Leu | Pro<br>480 |
| Gly | Ser | Pro | Gly | Ala<br>485 | Pro | Gly | Thr | Pro | Gly<br>490 | Pro | Gln | Gly | Leu | Pro<br>495 | Gly |
| Ser | Pro | Gly | Ala<br>500 | Pro | Gly | Thr | Pro | Gly<br>505 | Pro | Gln | Gly | Leu | Pro<br>510 | Gly | Ser |
| Pro | Gly | Ala<br>515 | Pro | Gly | Thr | Pro | Gly<br>520 | Pro | Gln | Gly | Leu | Pro<br>525 | Gly | Ser | Pro |
| Gly | Ala<br>530 | Pro | Gly | Thr | Pro | Gly<br>535 | Pro | Gln | Gly | Leu | Pro<br>540 | Gly | Ser | Pro | Gly |
| Ala<br>545 | Pro | Gly | Thr | Pro | Gly<br>550 | Pro | Gln | Gly | Leu | Pro<br>555 | Gly | Ser | Pro | Gly | Ala<br>560 |
| Pro | Gly | Thr | Pro | Gly<br>565 | Pro | Gln | Gly | Leu | Pro<br>570 | Gly | Ser | Pro | Gly | Ala<br>575 | Pro |
| Gly | Thr | Pro | Gly<br>580 | Pro | Gln | Gly | Leu | Pro<br>585 | Gly | Ser | Pro | Gly | Ala<br>590 | Pro | Gly |
| Thr | Pro | Gly<br>595 | Pro | Gln | Gly | Leu | Pro<br>600 | Gly | Ser | Pro | Gly | Ala<br>605 | Pro | Gly | Thr |
| Pro | Gly<br>610 | Pro | Gln | Gly | Leu | Pro<br>615 | Gly | Ser | Pro | Gly | Ala<br>620 | Pro | Gly | Thr | Pro |
| Gly | Pro | Gln | Gly | Leu | Pro | Gly | Ser | Pro | Gly | Ala | Pro | Gly | Thr | Pro | Gly |

```
          625                    630                      635                    640
    Pro Gln Gly Leu Pro Gly Ser Pro Gly Ala Pro Gly Thr Pro Gly Pro
                    645                 650                 655
    Gln Gly Leu Pro Gly Ser Pro Gly Ala Pro Gly Thr Pro Gly Pro Gln
                660                 665                 670
    Gly Leu Pro Gly Ser Pro Gly Ala Pro Gly Thr Pro Gly Pro Gln Gly
            675                 680                 685
    Leu Pro Gly Ser Pro Gly Ala Pro Gly Thr Pro Gly Pro Gln Gly Leu
        690                 695                 700
    Pro Gly Ser Pro Gly Ala Pro Gly Thr Pro Gly Pro Gln Gly Leu Pro
    705                 710                 715                 720
    Gly Ser Pro Gly Ala Pro Gly Thr Pro Gly Pro Gln Gly Leu Pro Gly
                    725                 730                 735
    Ser Pro Gly Ala Pro Gly Thr Pro Gly Pro Gln Gly Leu Pro Gly Ser
                740                 745                 750
    Pro Gly Ala Pro Gly Thr Pro Gly Pro Gln Gly Leu Pro Gly Ser Pro
            755                 760                 765
    Gly Ala Pro Gly Thr Pro Gly Pro Gln Gly Leu Pro Gly Ser Pro Gly
        770                 775                 780
    Ala Pro Gly Thr Pro Gly Pro Gln Gly Leu Pro Gly Ser Pro Gly Ala
    785                 790                 795                 800
    Pro Gly Thr Pro Gly Pro Gln Gly Leu Pro Gly Ser Pro Gly Ala Met
                    805                 810                 815
    Asp Pro Gly Arg Tyr Gln Leu Ser Ala Gly Arg Tyr His Tyr Gln Leu
                820                 825                 830
    Val Trp Cys Gln Lys
                835
```

(2) INFORMATION FOR SEQ ID NO:69:

(i) SEQUENCE CHARACTERISTICS:
 (A) LENGTH: 417 amino acids
 (B) TYPE: amino acid
 (C) STRANDEDNESS: single
 (D) TOPOLOGY: linear (ii) MOLECULE TYPE: peptide (xi) SEQUENCE DESCRIPTION: SEQ ID NO:69:

```
    Met Asp Pro Val Val Leu Gln Arg Arg Asp Trp Glu Asn Pro Gly Val
    1               5                   10                  15
    Thr Gln Leu Asn Arg Leu Ala Ala His Pro Pro Phe Ala Ser Asp Pro
                20                  25                  30
    Met Gly Ala Pro Gly Thr Pro Gly Pro Gln Gly Leu Pro Gly Ser Pro
                35                  40                  45
    Gly Ala Pro Gly Thr Pro Gly Pro Gln Gly Leu Pro Gly Ser Pro Gly
            50                  55                  60
    Ala Pro Gly Thr Pro Gly Pro Gln Gly Leu Pro Gly Ser Pro Gly Ala
    65                  70                  75                  80
    Pro Gly Thr Pro Gly Pro Gln Gly Leu Pro Gly Ser Pro Gly Ala Pro
                    85                  90                  95
    Gly Thr Pro Gly Pro Gln Gly Leu Pro Gly Ser Pro Gly Ala Pro Gly
                100                 105                 110
    Thr Pro Gly Pro Gln Gly Leu Pro Gly Ser Pro Gly Ala Pro Gly Thr
            115                 120                 125
    Pro Gly Pro Gln Gly Leu Pro Gly Ser Pro Gly Ala Pro Gly Thr Pro
    130                 135                 140
```

Gly Pro Gln Gly Leu Pro Gly Ser Pro Gly Ala Pro Gly Thr Pro Gly
145             150             155             160

Pro Gln Gly Leu Pro Gly Ser Pro Gly Ala Pro Gly Thr Pro Gly Pro
            165             170             175

Gln Gly Leu Pro Gly Ser Pro Gly Ala Pro Gly Thr Pro Gly Pro Gln
        180             185             190

Gly Leu Pro Gly Ser Pro Gly Ala Pro Gly Thr Pro Gly Pro Gln Gly
    195             200             205

Leu Pro Gly Ser Pro Gly Ala Pro Gly Thr Pro Gly Pro Gln Gly Leu
210             215             220

Pro Gly Ser Pro Gly Ala Pro Gly Thr Pro Gly Pro Gln Gly Leu Pro
225             230             235             240

Gly Ser Pro Gly Ala Pro Gly Thr Pro Gly Pro Gln Gly Leu Pro Gly
            245             250             255

Ser Pro Gly Ala Pro Gly Thr Pro Gly Pro Gln Gly Leu Pro Gly Ser
        260             265             270

Pro Gly Ala Pro Gly Thr Pro Gly Pro Gln Gly Leu Pro Gly Ser Pro
    275             280             285

Gly Ala Pro Gly Thr Pro Gly Pro Gln Gly Leu Pro Gly Ser Pro Gly
290             295             300

Ala Pro Gly Thr Pro Gly Pro Gln Gly Leu Pro Gly Ser Pro Gly Ala
305             310             315             320

Pro Gly Thr Pro Gly Pro Gln Gly Leu Pro Gly Ser Pro Gly Ala Pro
            325             330             335

Gly Thr Pro Gly Pro Gln Gly Leu Pro Gly Ser Pro Gly Ala Pro Gly
        340             345             350

Thr Pro Gly Pro Gln Gly Leu Pro Gly Ser Pro Gly Ala Pro Gly Thr
    355             360             365

Pro Gly Pro Gln Gly Leu Pro Gly Ser Pro Gly Ala Pro Gly Thr Pro
370             375             380

Gly Pro Gln Gly Leu Pro Gly Ser Pro Gly Ala Met Asp Pro Gly Arg
385             390             395             400

Tyr Gln Leu Ser Ala Gly Arg Tyr His Tyr Gln Leu Val Trp Cys Gln
            405             410             415

Lys